(12) United States Patent
Turner et al.

(10) Patent No.: US 10,583,156 B2
(45) Date of Patent: Mar. 10, 2020

(54) NANOPARTICLE FORMULATIONS

(71) Applicant: Taiga Biotechnologies, Inc., Aurora, CO (US)

(72) Inventors: Brian Curtis Turner, Denver, CO (US); Yosef Refaeli, Denver, CO (US); Gregory Alan Bird, Littleton, CO (US)

(73) Assignee: TAIGA BIOTECHNOLOGIES, INC., Aurora, CO (US)

( * ) Notice: Subject to any disclaimer, the term of this patent is extended or adjusted under 35 U.S.C. 154(b) by 27 days.

(21) Appl. No.: 15/828,971

(22) Filed: Dec. 1, 2017

(65) Prior Publication Data

US 2018/0153939 A1   Jun. 7, 2018

Related U.S. Application Data

(60) Provisional application No. 62/429,466, filed on Dec. 2, 2016.

(51) Int. Cl.

| | |
|---|---|
| *C07K 19/00* | (2006.01) |
| *A61K 39/39* | (2006.01) |
| *A61K 35/17* | (2015.01) |
| *C07K 14/82* | (2006.01) |
| *A61K 39/395* | (2006.01) |
| *C07K 14/47* | (2006.01) |
| *C07K 14/725* | (2006.01) |
| *C07K 14/73* | (2006.01) |
| *C07K 14/705* | (2006.01) |
| *C12N 5/0783* | (2010.01) |
| *A61K 38/00* | (2006.01) |

(52) U.S. Cl.
CPC ........ *A61K 35/17* (2013.01); *A61K 39/39566* (2013.01); *C07K 14/4702* (2013.01); *C07K 14/7051* (2013.01); *C07K 14/70514* (2013.01); *C07K 14/70517* (2013.01); *C07K 14/82* (2013.01); *C12N 5/0636* (2013.01); *A61K 38/00* (2013.01); *C07K 2319/10* (2013.01); *C07K 2319/41* (2013.01); *C12N 2501/606* (2013.01)

(58) Field of Classification Search
CPC ... C07K 19/00; A61K 39/39; C12N 2501/606
See application file for complete search history.

(56) References Cited

U.S. PATENT DOCUMENTS

| | | |
|---|---|---|
| 5,652,122 A | 7/1997 | Frankel et al. |
| 5,670,617 A | 9/1997 | Frankel et al. |
| 5,674,980 A | 10/1997 | Frankel et al. |
| 5,747,641 A | 5/1998 | Frankel et al. |
| 5,804,604 A | 9/1998 | Frankel et al. |
| 2014/0109246 A1* | 4/2014 | Jimeno ............. A61K 49/0008 800/10 |
| 2014/0356392 A1 | 12/2014 | Refaeli et al. |
| 2015/0164950 A1 | 6/2015 | Turner et al. |

FOREIGN PATENT DOCUMENTS

| | | |
|---|---|---|
| EP | 0 367 76 A2 | 9/1981 |
| WO | WO-2016/105542 | 6/2016 |

OTHER PUBLICATIONS

Watt et al. 1983; Nucleotide sequence of cloned cDNA of human c-myc oncogene. Nature. 303:725-728.*
Bird et al., "Expansion of Human and Murine Hematopoietic Stem and progenitor Cells Ex Vivo without Genetic Modification Using MYC and Bcl-2 Fusion Proteins," PLoS One, Aug. 29, 2014, vol. 9, No. 8, pp. 1-20.
International Search Report and Written Opinion for PCT/US2017/064206, dated Mar. 19, 2018.
Patel et al., "The c-MYC oncoprotein is a substrate of the acetyltransferases hGCN5/PCAF and TIP60," Molecular and Cellular Biology, Dec. 1, 2004, vol. 24, No. 24, pp. 10826-10834.
Stein et al., "TAT-MYC Recombinant Fusion Protein Enhances Hematopoietic Stem Cell Graft Performance and Immune Cell Reconstitution after Transplantation," Blood, Dec. 7, 2017, vol. 130, Suppl. 1, p. 3175.
Chang, et al., "Phenotypic expression in *E. coli* of a DNA sequence coding for mouse dihydrofolate reductase," Nature, vol. 275, Oct. 19, 1978, pp. 617-624.
Chi, et al., "Physical Stability of Proteins in Aqueous Solution: Mechanism and Driving Forces in Nonnative Protein Aggregation," Pharm. Res., vol. 20, No. 9, Sep. 2003, pp. 1325-1336.
Cleland, et al., "The development of stable protein formulations: a close look at protein aggregation, deamidation, and oxidation," Crit. Rev. Ther. Drug Carrier Syst., vol. 70, No. 4, Jan. 1, 1993, pp. 307-377.
Deboer, et al., "The tac promoter: A functional hybrid derived from the trp and lac promoters," Proc. Natl. Acad. Sci. vol. 80, Jan. 1983, pp. 21-25.
Derossi, et al., "Trojan peptides: the penetratin system for intracellular delivery," Cell Biology, vol. 8, Feb. 1998, pp. 84-87.
Elliot, et al., "Intercellular Trafficking and Protein Delivery by a Herpesvirus Structural Protein," Cell, vol. 88, Jan. 24, 1997, pp. 223-233.
Goeddel, et al., "Direct expression in *Escherichia coli* of a DNA sequence coding for human growth hormone," Nature, vol. 281, Oct. 18, 1979, p. 544.
Goeddel, et al., "Synthesis of human fibroblast interferon by *E. coli*," Nucleic Acids Research, vol. 8, Aug. 12, 1980, p. 4057.
Heinkoff, et al., "Amino acid substitution matrices from protein blocks," Proc. Natl Acad. Sci. USA, vol. 89, Nov. 1992, pp. 10915-10919.
Huang, et al., "Negative Control of the Myc Protein by the Stress-Responsive Kinase Pak2," Molecular and Cellular Biology, vol. 24, No. 4, Feb. 2001, pp. 1582-1594.

(Continued)

*Primary Examiner* — Karen Cochrane Carlson
(74) *Attorney, Agent, or Firm* — Foley & Lardner LLP

(57) ABSTRACT

This present disclosure relates to methods and compositions comprising biologically active nanoparticle formulations of MYC protein. Provided are methods of making the nanoparticle formulations and methods of using the nanoparticle formulations for treatment.

13 Claims, 27 Drawing Sheets

Specification includes a Sequence Listing.

(56) References Cited

OTHER PUBLICATIONS

Kaptein, et al., "Anti-IgM-mediated Regulation of c-myc and Its Possible Relationship to Apoptosis," JBC, vol. 271, No. 31, Aug. 2, 1996, pp. 18875-18884.

Schwarze, et al., "In vivo protein transduction: intracellular delivery of biologically active proteins, compounds and DNA," Trends Pharmacol Sci, vol. 21, Feb. 2000, pp. 45-48.

Siebenlist, et al., "*E. coli* RNA Polymerase Interacts Homologously with Two Different Promoters," Cell, vol. 20, Jun. 1980, pp. 269-281.

Wang, "Instability, stabilization, and formulation of liquid protein pharmaceuticals," Int. J. Pharm., vol. 185, Issue 2, Aug. 20, 1999, pp. 129-188.

Wang, "Lyophilization and development of solid protein pharmaceuticals," Int. J. Pharm., vol. 203, Issues 1-2, Aug. 2000, pp. 1-60.

\* cited by examiner

Zoom – full region

Full Chromatogram

Zoom around main peak

SEQUENCE LISTING

<160> NUMBER OF SEQ ID NOS: 44

<210> SEQ ID NO 1
<211> LENGTH: 476
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Arg Lys Lys Arg Arg Gln Arg Arg Pro Leu Asn Val Ser Phe
1               5                   10                  15

Thr Asn Arg Asn Tyr Asp Leu Asp Tyr Asp Ser Val Gln Pro Tyr Phe
                20                  25                  30

Tyr Cys Asp Glu Glu Glu Asn Phe Tyr Gln Gln Gln Gln Ser Glu
                35                  40                  45

Leu Gln Pro Pro Ala Pro Ser Glu Asp Ile Trp Lys Lys Phe Glu Leu
50                  55                  60

Leu Pro Thr Pro Pro Leu Ser Pro Ser Arg Arg Ser Gly Leu Cys Ser
65                  70                  75                  80

Pro Ser Tyr Val Ala Val Thr Pro Phe Ser Leu Arg Gly Asp Asn Asp
                85                  90                  95

Gly Gly Gly Gly Ser Phe Ser Thr Ala Asp Gln Leu Glu Met Val Thr
                100                 105                 110

Glu Leu Leu Gly Gly Asp Met Val Asn Gln Ser Phe Ile Cys Asp Pro
                115                 120                 125

Asp Asp Glu Thr Phe Ile Lys Asn Ile Ile Ile Gln Asp Cys Met Trp
                130                 135                 140

Ser Gly Phe Ser Ala Ala Ala Lys Leu Val Ser Glu Lys Leu Ala Ser
145                 150                 155                 160

Tyr Gln Ala Ala Arg Lys Asp Ser Gly Ser Pro Asn Pro Ala Arg Gly
                165                 170                 175

His Ser Val Cys Ser Thr Ser Ser Leu Tyr Leu Gln Asp Leu Ser Ala
                180                 185                 190

Ala Ala Ser Glu Cys Ile Asp Pro Ser Val Val Phe Pro Tyr Pro Leu
                195                 200                 205

Asn Asp Ser Ser Ser Pro Lys Ser Cys Ala Ser Gln Asp Ser Ser Ala
                210                 215                 220

Phe Ser Pro Ser Ser Asp Ser Leu Leu Ser Ser Thr Glu Ser Ser Pro
225                 230                 235                 240

Gln Gly Ser Pro Glu Pro Leu Val Leu His Glu Glu Thr Pro Pro Thr
                245                 250                 255

Thr Ser Ser Asp Ser Glu Glu Glu Gln Glu Asp Glu Glu Glu Ile Asp
                260                 265                 270

Val Val Ser Val Glu Lys Arg Gln Ala Pro Gly Lys Arg Ser Glu Ser
                275                 280                 285

Gly Ser Pro Ser Ala Gly Gly His Ser Lys Pro Pro His Ser Pro Leu
290                 295                 300

Val Leu Lys Arg Cys His Val Ser Thr His Gln His Asn Tyr Ala Ala
305                 310                 315                 320

Pro Pro Ser Thr Arg Lys Asp Tyr Pro Ala Ala Lys Arg Val Lys Leu
                325                 330                 335

Asp Ser Val Arg Val Leu Arg Gln Ile Ser Asn Asn Arg Lys Cys Thr
                340                 345                 350

-continued

```
Ser Pro Arg Ser Ser Asp Thr Glu Glu Asn Val Lys Arg Thr His
            355                 360                 365

Asn Val Leu Glu Arg Gln Arg Asn Glu Leu Lys Arg Ser Phe Phe
370                 375                 380

Ala Leu Arg Asp Gln Ile Pro Glu Leu Glu Asn Asn Glu Lys Ala Pro
385                 390                 395                 400

Lys Val Val Ile Leu Lys Lys Ala Thr Ala Tyr Ile Leu Ser Val Gln
                405                 410                 415

Ala Glu Glu Gln Lys Leu Ile Ser Glu Asp Leu Leu Arg Lys Arg
                420                 425                 430

Arg Glu Gln Leu Lys His Lys Leu Glu Gln Leu Arg Lys Gly Glu Leu
            435                 440                 445

Asn Ser Lys Leu Glu Gly Lys Pro Ile Pro Asn Pro Leu Leu Gly Leu
450                 455                 460

Asp Ser Thr Arg Thr Gly His His His His His
465                 470                 475

<210> SEQ ID NO 2
<211> LENGTH: 454
<212> TYPE: PRT
<213> ORGANISM: Homo sapiens

<400> SEQUENCE: 2

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
                20                  25                  30

Ser Val Gln Pro Tyr Phe Tyr Cys Asp Glu Glu Glu Asn Phe Tyr Gln
            35                  40                  45

Gln Gln Gln Gln Ser Glu Leu Gln Pro Pro Ala Pro Ser Glu Asp Ile
        50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
                100                 105                 110

Gln Leu Glu Met Val Thr Glu Leu Leu Gly Gly Asp Met Val Asn Gln
            115                 120                 125

Ser Phe Ile Cys Asp Pro Asp Asp Glu Thr Phe Ile Lys Asn Ile Ile
        130                 135                 140

Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205

Val Phe Pro Tyr Pro Leu Asn Asp Ser Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255
```

```
Glu Glu Thr Pro Pro Thr Thr Ser Ser Asp Ser Glu Glu Gln Glu
            260                 265                 270

Asp Glu Glu Ile Asp Val Val Ser Val Glu Lys Arg Gln Ala Pro
            275                 280                 285

Gly Lys Arg Ser Glu Ser Gly Ser Pro Ser Ala Gly Gly His Ser Lys
        290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
            355                 360                 365

Val Lys Arg Arg Thr His Asn Val Leu Glu Arg Gln Arg Arg Asn Glu
        370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
            435                 440                 445

Leu Arg Asn Ser Cys Ala
        450

<210> SEQ ID NO 3
<211> LENGTH: 459
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30

Ser Val Gln Pro Tyr Phe Tyr Cys Asp Glu Glu Glu Asn Phe Tyr Gln
        35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
            100                 105                 110

Gln Leu Glu Met Val Thr Glu Leu Leu Gly Gly Asp Met Val Asn Gln
        115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Ala Lys Leu Val
```

```
                145                 150                 155                 160
Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ala Ser Glu Cys Ile Asp Pro Ser Val
        195                 200                 205

Val Phe Pro Tyr Pro Leu Asn Asp Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
            260                 265                 270

Asp Glu Glu Glu Ile Asp Val Val Ser Val Glu Lys Arg Gln Ala Pro
        275                 280                 285

Gly Lys Arg Ser Glu Ser Gly Ser Pro Ser Ala Gly Gly His Ser Lys
    290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
        355                 360                 365

Val Lys Arg Arg Thr His Asn Val Leu Glu Arg Gln Arg Arg Asn Glu
    370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Glu Gln Leu Lys His Lys Leu Glu Gln
        435                 440                 445

Leu Arg Lys Gly Glu Leu Asn Ser Lys Leu Glu
    450                 455

<210> SEQ ID NO 4
<211> LENGTH: 434
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Pro Leu Asn Val Ser Phe Thr Asn Arg Asn Tyr Asp Leu Asp Tyr Asp
1               5                   10                  15

Ser Val Gln Pro Tyr Phe Tyr Cys Asp Glu Glu Glu Asn Phe Tyr Gln
            20                  25                  30

Gln Gln Gln Gln Ser Glu Leu Gln Pro Pro Ala Pro Ser Glu Asp Ile
        35                  40                  45
```

```
            Trp Lys Lys Phe Glu Leu Leu Pro Thr Pro Pro Leu Ser Pro Ser Arg
                 50                  55                  60

Arg Ser Gly Leu Cys Ser Pro Ser Tyr Val Ala Val Thr Pro Phe Ser
             65                  70                  75                  80

Leu Arg Gly Asp Asn Asp Gly Gly Gly Ser Phe Ser Thr Ala Asp
                             85                  90                  95

Gln Leu Glu Met Val Thr Glu Leu Leu Gly Gly Asp Met Val Asn Gln
                            100                 105                 110

Ser Phe Ile Cys Asp Pro Asp Glu Thr Phe Ile Lys Asn Ile Ile
                        115                 120                 125

Ile Gln Asp Cys Met Trp Ser Gly Phe Ser Ala Ala Ala Lys Leu Val
                    130                 135                 140

Ser Glu Lys Leu Ala Ser Tyr Gln Ala Ala Arg Lys Asp Ser Gly Ser
            145                 150                 155                 160

Pro Asn Pro Ala Arg Gly His Ser Val Cys Ser Thr Ser Ser Leu Tyr
                                165                 170                 175

Leu Gln Asp Leu Ser Ala Ala Ser Glu Cys Ile Asp Pro Ser Val
                        180                 185                 190

Val Phe Pro Tyr Pro Leu Asn Asp Ser Ser Pro Lys Ser Cys Ala
                    195                 200                 205

Ser Gln Asp Ser Ser Ala Phe Ser Pro Ser Ser Asp Ser Leu Leu Ser
                    210                 215                 220

Ser Thr Glu Ser Ser Pro Gln Gly Ser Pro Glu Pro Leu Val Leu His
            225                 230                 235                 240

Glu Glu Thr Pro Pro Thr Thr Ser Ser Asp Ser Glu Glu Gln Glu
                                245                 250                 255

Asp Glu Glu Glu Ile Asp Val Val Ser Val Glu Lys Arg Gln Ala Pro
                            260                 265                 270

Gly Lys Arg Ser Glu Ser Gly Ser Pro Ser Ala Gly Gly His Ser Lys
                        275                 280                 285

Pro Pro His Ser Pro Leu Val Leu Lys Arg Cys His Val Ser Thr His
                    290                 295                 300

Gln His Asn Tyr Ala Ala Pro Pro Ser Thr Arg Lys Asp Tyr Pro Ala
            305                 310                 315                 320

Ala Lys Arg Val Lys Leu Asp Ser Val Arg Val Leu Arg Gln Ile Ser
                                325                 330                 335

Asn Asn Arg Lys Cys Thr Ser Pro Arg Ser Ser Asp Thr Glu Glu Asn
                            340                 345                 350

Val Lys Arg Arg Thr His Asn Val Leu Glu Arg Gln Arg Arg Asn Glu
                        355                 360                 365

Leu Lys Arg Ser Phe Phe Ala Leu Arg Asp Gln Ile Pro Glu Leu Glu
                    370                 375                 380

Asn Asn Glu Lys Ala Pro Lys Val Val Ile Leu Lys Lys Ala Thr Ala
            385                 390                 395                 400

Tyr Ile Leu Ser Val Gln Ala Glu Glu Gln Lys Leu Ile Ser Glu Glu
                                405                 410                 415

Asp Leu Leu Arg Lys Arg Arg Glu Gln Leu Lys His Lys Leu Glu Gln
                            420                 425                 430

Leu Arg

<210> SEQ ID NO 5
<211> LENGTH: 67
<212> TYPE: PRT
<213> ORGANISM: Homo sapiens
```

<400> SEQUENCE: 5

```
Glu Leu Lys Arg Ser Phe Phe Ala Leu Arg Asp Gln Ile Pro Glu Leu
1               5                   10                  15

Glu Asn Asn Glu Lys Ala Pro Lys Val Val Ile Leu Lys Lys Ala Thr
            20                  25                  30

Ala Tyr Ile Leu Ser Val Gln Ala Glu Glu Gln Lys Leu Ile Ser Glu
        35                  40                  45

Glu Asp Leu Leu Arg Lys Arg Glu Gln Leu Lys His Lys Leu Glu
    50                  55                  60

Gln Leu Arg
65
```

<210> SEQ ID NO 6
<211> LENGTH: 14
<212> TYPE: PRT
<213> ORGANISM: Unknown
<220> FEATURE:
<223> OTHER INFORMATION: Description of Unknown: E-box DNA binding
      domain sequence

<400> SEQUENCE: 6

```
Lys Arg Arg Thr His Asn Val Leu Glu Arg Gln Arg Arg Asn
1               5                   10
```

<210> SEQ ID NO 7
<211> LENGTH: 10
<212> TYPE: PRT
<213> ORGANISM: Human immunodeficiency virus 1

<400> SEQUENCE: 7

```
Met Arg Lys Lys Arg Arg Gln Arg Arg Arg
1               5                   10
```

<210> SEQ ID NO 8
<211> LENGTH: 439
<212> TYPE: PRT
<213> ORGANISM: Chlorocebus sabaeus

<400> SEQUENCE: 8

```
Met Pro Leu Asn Val Ser Phe Thr Asn Arg Asn Tyr Asp Leu Asp Tyr
1               5                   10                  15

Asp Ser Val Gln Pro Tyr Phe Tyr Cys Asp Glu Glu Glu Asn Phe Tyr
            20                  25                  30

Gln Gln Gln Gln Gln Ser Glu Leu Gln Pro Pro Ala Pro Ser Glu Asp
        35                  40                  45

Ile Trp Lys Lys Phe Glu Leu Leu Pro Thr Pro Pro Leu Ser Pro Ser
    50                  55                  60

Arg Arg Ser Gly Leu Cys Ser Pro Ser Tyr Val Ala Val Thr Pro Phe
65                  70                  75                  80

Ser Pro Arg Gly Asp Asn Asp Gly Gly Gly Gly Ser Phe Ser Thr Ala
                85                  90                  95

Asp Gln Leu Glu Met Val Thr Glu Leu Leu Gly Gly Asp Met Val Asn
            100                 105                 110

Gln Ser Phe Ile Cys Asp Pro Asp Asp Glu Thr Phe Ile Lys Asn Ile
        115                 120                 125

Ile Ile Gln Asp Cys Met Trp Ser Gly Phe Ser Ala Ala Ala Lys Leu
    130                 135                 140

Val Ser Glu Lys Leu Ala Ser Tyr Gln Ala Ala Arg Lys Asp Ser Gly
```

```
            145                 150                 155                 160
       Ser Pro Asn Pro Ala Arg Gly His Ser Val Cys Ser Thr Ser Ser Leu
                       165                 170                 175

Tyr Leu Gln Asp Leu Ser Ala Ala Ser Glu Cys Ile Asp Pro Ser
                       180                 185                 190

Val Val Phe Pro Tyr Pro Leu Asn Asp Ser Ser Pro Lys Ser Cys
                   195                 200                 205

Ala Ser Pro Asp Ser Ser Ala Phe Ser Pro Ser Asp Ser Leu Leu
               210                 215                 220

Ser Ser Thr Glu Ser Ser Pro Gln Ala Ser Pro Glu Pro Leu Val Leu
       225                 230                 235                 240

His Glu Glu Thr Pro Pro Thr Thr Ser Ser Asp Ser Glu Glu Glu Gln
                       245                 250                 255

Glu Asp Glu Glu Glu Ile Asp Val Val Ser Val Glu Lys Arg Gln Ala
                   260                 265                 270

Pro Gly Lys Arg Ser Glu Ser Gly Ser Pro Ser Ala Gly Gly His Ser
                   275                 280                 285

Lys Pro Pro His Ser Pro Leu Val Leu Lys Arg Cys His Val Ser Thr
       290                 295                 300

His Gln His Asn Tyr Ala Ala Pro Pro Ser Thr Arg Lys Asp Tyr Pro
       305                 310                 315                 320

Ala Ala Lys Arg Val Lys Leu Asp Ser Val Arg Val Leu Arg Gln Ile
                       325                 330                 335

Ser Asn Asn Arg Lys Cys Thr Ser Pro Arg Ser Ser Asp Thr Glu Glu
                       340                 345                 350

Asn Val Lys Arg Arg Thr His Asn Val Leu Glu Arg Gln Arg Arg Asn
                       355                 360                 365

Glu Leu Lys Arg Ser Phe Phe Ala Leu Arg Asp Gln Ile Pro Glu Leu
                       370                 375                 380

Glu Asn Asn Glu Lys Ala Pro Lys Val Val Ile Leu Lys Lys Ala Thr
       385                 390                 395                 400

Ala Tyr Ile Leu Ser Val Gln Ala Glu Glu Gln Lys Leu Ile Ser Glu
                       405                 410                 415

Lys Asp Leu Leu Arg Lys Arg Arg Glu Gln Leu Lys His Lys Leu Glu
                       420                 425                 430

Gln Leu Arg Asn Ser Cys Ala
                       435

<210> SEQ ID NO 9
<211> LENGTH: 434
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Pro Leu Asn Val Ser Phe Thr Asn Arg Asn Tyr Asp Leu Asp Tyr Asp
1               5                   10                  15

Ser Val Gln Pro Tyr Phe Tyr Cys Asp Glu Glu Glu Asn Phe Tyr Gln
                20                  25                  30

Gln Gln Gln Gln Ser Glu Leu Gln Pro Pro Ala Pro Ser Glu Asp Ile
            35                  40                  45

Trp Lys Lys Phe Glu Leu Leu Pro Thr Pro Pro Leu Ser Pro Ser Arg
        50                  55                  60
```

```
Arg Ser Gly Leu Cys Ser Pro Ser Tyr Val Ala Val Thr Pro Phe Ser
 65                  70                  75                  80

Leu Arg Gly Asp Asn Asp Gly Gly Gly Ser Phe Ser Thr Ala Asp
             85                  90                  95

Gln Leu Glu Met Val Thr Glu Leu Leu Gly Gly Asp Met Val Asn Gln
            100                 105                 110

Ser Phe Ile Cys Asp Pro Asp Glu Thr Phe Ile Lys Asn Ile Ile
            115                 120                 125

Ile Gln Asp Cys Met Trp Ser Gly Phe Ser Ala Ala Lys Leu Val
        130                 135                 140

Ser Glu Lys Leu Ala Ser Tyr Gln Ala Ala Arg Lys Asp Ser Gly Ser
145                 150                 155                 160

Pro Asn Pro Ala Arg Gly His Ser Val Cys Ser Thr Ser Ser Leu Tyr
                165                 170                 175

Leu Gln Asp Leu Ser Ala Ala Ala Ser Glu Cys Ile Asp Pro Ser Val
            180                 185                 190

Val Phe Pro Tyr Pro Leu Asn Asp Ser Ser Ser Pro Lys Ser Cys Ala
        195                 200                 205

Ser Gln Asp Ser Ser Ala Phe Ser Pro Ser Ser Asp Ser Leu Leu Ser
210                 215                 220

Ser Thr Glu Ser Ser Pro Gln Ala Ser Pro Glu Pro Leu Val Leu His
225                 230                 235                 240

Glu Glu Thr Pro Pro Thr Thr Ser Ser Asp Ser Glu Glu Glu Gln Glu
                245                 250                 255

Asp Glu Glu Glu Ile Asp Val Val Ser Val Glu Lys Arg Gln Ala Pro
            260                 265                 270

Gly Lys Arg Ser Glu Ser Gly Ser Pro Ser Ala Gly Gly His Ser Lys
        275                 280                 285

Pro Pro His Ser Pro Leu Val Leu Lys Arg Cys His Val Ser Thr His
        290                 295                 300

Gln His Asn Tyr Ala Ala Pro Pro Ser Thr Arg Lys Asp Tyr Pro Ala
305                 310                 315                 320

Ala Lys Arg Val Lys Leu Asp Ser Val Arg Val Leu Arg Gln Ile Ser
                325                 330                 335

Asn Asn Arg Lys Cys Thr Ser Pro Arg Ser Ser Asp Thr Glu Glu Asn
            340                 345                 350

Val Lys Arg Arg Thr His Asn Val Leu Glu Arg Gln Arg Arg Asn Glu
        355                 360                 365

Leu Lys Arg Ser Phe Phe Ala Leu Arg Asp Gln Ile Pro Glu Leu Glu
        370                 375                 380

Asn Asn Glu Lys Ala Pro Lys Val Val Ile Leu Lys Lys Ala Thr Ala
385                 390                 395                 400

Tyr Ile Leu Ser Val Gln Ala Glu Glu Gln Lys Leu Ile Ser Glu Lys
                405                 410                 415

Asp Leu Leu Arg Lys Arg Arg Glu Gln Leu Lys His Lys Leu Glu Gln
            420                 425                 430

Leu Arg

<210> SEQ ID NO 10
<211> LENGTH: 476
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 10

Met Arg Lys Lys Arg Gln Arg Arg Pro Leu Asn Val Ser Phe
1               5                   10                  15

Thr Asn Arg Asn Tyr Asp Leu Asp Tyr Asp Ser Val Gln Pro Tyr Phe
            20                  25                  30

Tyr Cys Asp Glu Glu Asn Phe Tyr Gln Gln Gln Gln Ser Glu
        35                  40                  45

Leu Gln Pro Pro Ala Pro Ser Glu Asp Ile Trp Lys Lys Phe Glu Leu
    50                  55                  60

Leu Pro Thr Pro Pro Leu Ser Pro Ser Arg Arg Ser Gly Leu Cys Ser
65                  70                  75                  80

Pro Ser Tyr Val Ala Val Thr Pro Phe Ser Leu Arg Gly Asp Asn Asp
                85                  90                  95

Gly Gly Gly Gly Ser Phe Ser Thr Ala Asp Gln Leu Glu Met Val Thr
                100                 105                 110

Glu Leu Leu Gly Gly Asp Met Val Asn Gln Ser Phe Ile Cys Asp Pro
            115                 120                 125

Asp Asp Glu Thr Phe Ile Lys Asn Ile Ile Gln Asp Cys Met Trp
130                 135                 140

Ser Gly Phe Ser Ala Ala Ala Lys Leu Val Ser Glu Lys Leu Ala Ser
145                 150                 155                 160

Tyr Gln Ala Ala Arg Lys Asp Ser Gly Ser Pro Asn Pro Ala Arg Gly
                165                 170                 175

His Ser Val Cys Ser Thr Ser Ser Leu Tyr Leu Gln Asp Leu Ser Ala
            180                 185                 190

Ala Ala Ser Glu Cys Ile Asp Pro Ser Val Val Phe Pro Tyr Pro Leu
            195                 200                 205

Asn Asp Ser Ser Ser Pro Lys Ser Cys Ala Ser Gln Asp Ser Ser Ala
210                 215                 220

Phe Ser Pro Ser Ser Asp Ser Leu Leu Ser Ser Thr Glu Ser Ser Pro
225                 230                 235                 240

Gln Ala Ser Pro Glu Pro Leu Val Leu His Glu Glu Thr Pro Pro Thr
                245                 250                 255

Thr Ser Ser Asp Ser Glu Glu Glu Gln Glu Asp Glu Glu Ile Asp
            260                 265                 270

Val Val Ser Val Glu Lys Arg Gln Ala Pro Gly Lys Arg Ser Glu Ser
            275                 280                 285

Gly Ser Pro Ser Ala Gly Gly His Ser Lys Pro Pro His Ser Pro Leu
290                 295                 300

Val Leu Lys Arg Cys His Val Ser Thr His Gln His Asn Tyr Ala Ala
305                 310                 315                 320

Pro Pro Ser Thr Arg Lys Asp Tyr Pro Ala Ala Lys Arg Val Lys Leu
                325                 330                 335

Asp Ser Val Arg Val Leu Arg Gln Ile Ser Asn Asn Arg Lys Cys Thr
            340                 345                 350

Ser Pro Arg Ser Ser Asp Thr Glu Glu Asn Val Lys Arg Arg Thr His
            355                 360                 365

Asn Val Leu Glu Arg Gln Arg Arg Asn Glu Leu Lys Arg Ser Phe Phe
            370                 375                 380

Ala Leu Arg Asp Gln Ile Pro Glu Leu Glu Asn Asn Glu Lys Ala Pro
385                 390                 395                 400

Lys Val Val Ile Leu Lys Lys Ala Thr Ala Tyr Ile Leu Ser Val Gln
```

```
                        405                 410                 415

Ala Glu Glu Gln Lys Leu Ile Ser Glu Lys Asp Leu Leu Arg Lys Arg
            420                 425                 430

Arg Glu Gln Leu Lys His Lys Leu Glu Gln Leu Arg Lys Gly Glu Leu
        435                 440                 445

Asn Ser Lys Leu Glu Gly Lys Pro Ile Pro Asn Leu Leu Gly Leu
    450                 455                 460

Asp Ser Thr Arg Thr Gly His His His His His His
465                 470                 475

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Gly Glu Leu Asn Ser Lys Leu Glu
1               5

<210> SEQ ID NO 12
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Met Arg Lys Lys Arg Arg Gln Arg Arg Arg Pro Leu Asn Val Ser Phe
1               5                   10                  15

Thr Asn Arg Asn Tyr Asp
            20

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Asp Leu Asp
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Asp Tyr Asp
1

<210> SEQ ID NO 15
<211> LENGTH: 11
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 15

Tyr Asp Ser Val Gln Pro Tyr Phe Tyr Cys Asp
1               5                   10

<210> SEQ ID NO 16
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Asp Glu Glu Glu Asn Phe Tyr Gln Gln Gln Gln Ser Glu Leu
1               5                   10                  15

Gln Pro Pro Ala Pro Ser Glu Asp
            20

<210> SEQ ID NO 17
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Asp Ile Trp Lys Lys Phe Glu Leu Leu Pro Thr Pro Pro Leu Ser
1               5                   10                  15

Pro Ser Arg Arg Ser Gly Leu Cys Ser Pro Ser Tyr Val Ala Val Thr
            20                  25                  30

Pro Phe Ser Leu Arg Gly Asp
            35

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Asp Asn Asp
1

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Asp Gly Gly Gly Gly Ser Phe Ser Thr Ala Asp
1               5                   10

<210> SEQ ID NO 20
<211> LENGTH: 14
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 20

Ala Asp Gln Leu Glu Met Val Thr Glu Leu Leu Gly Gly Asp
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Asp Met Val Asn Gln Ser Phe Ile Cys Asp
1               5                   10

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Cys Asp Pro Asp
1

<210> SEQ ID NO 23
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Pro Asp Asp
1

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Asp Glu Thr Phe Ile Lys Asn Ile Ile Ile Gln Asp
1               5                   10

<210> SEQ ID NO 25
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Asp Cys Met Trp Ser Gly Phe Ser Ala Ala Ala Lys Leu Val Ser
1               5                   10                  15

Glu Lys Leu Ala Ser Tyr Gln Ala Ala Arg Lys Asp
```

```
                20                  25

<210> SEQ ID NO 26
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Asp Ser Gly Ser Pro Asn Pro Ala Arg Gly His Ser Val Cys Ser
1               5                   10                  15

Thr Ser Ser Leu Tyr Leu Gln Asp
            20

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Asp Leu Ser Ala Ala Ala Ser Glu Cys Ile Asp
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ile Asp Pro Ser Val Val Phe Pro Tyr Pro Leu Asn Asp
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Asn Asp Ser Ser Ser Pro Lys Ser Cys Ala Ser Gln Asp
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Asp Ser Ser Ala Phe Ser Pro Ser Ser Asp
1               5                   10

<210> SEQ ID NO 31
<211> LENGTH: 32
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 31

Ser Asp Ser Leu Leu Ser Ser Thr Glu Ser Pro Gln Gly Ser Pro
1               5                   10                  15

Glu Pro Leu Val Leu His Glu Glu Thr Pro Pro Thr Thr Ser Ser Asp
            20                  25                  30

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Asp Ser Glu Glu Gln Glu Asp
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Glu Asp Glu Glu Glu Ile Asp
1               5

<210> SEQ ID NO 34
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ile Asp Val Val Ser Val Glu Lys Arg Gln Ala Pro Gly Lys Arg Ser
1               5                   10                  15

Glu Ser Gly Ser Pro Ser Ala Gly Gly His Ser Lys Pro Pro His Ser
            20                  25                  30

Pro Leu Val Leu Lys Arg Cys His Val Ser Thr His Gln His Asn Tyr
            35                  40                  45

Ala Ala Pro Pro Ser Thr Arg Lys Asp
        50                  55

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Asp Tyr Pro Ala Ala Lys Arg Val Lys Leu Asp
1               5                   10

```
<210> SEQ ID NO 36
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Leu Asp Ser Val Arg Val Leu Arg Gln Ile Ser Asn Asn Arg Lys Cys
1               5                   10                  15

Thr Ser Pro Arg Ser Ser Asp
            20

<210> SEQ ID NO 37
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ser Asp Thr Glu Glu Asn Val Lys Arg Arg Thr His Asn Val Leu Glu
1               5                   10                  15

Arg Gln Arg Arg Asn Glu Leu Lys Arg Ser Phe Phe Ala Leu Arg Asp
            20                  25                  30

<210> SEQ ID NO 38
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Arg Asp Gln Ile Pro Glu Leu Glu Asn Asn Glu Lys Ala Pro Lys Val
1               5                   10                  15

Val Ile Leu Lys Lys Ala Thr Ala Tyr Ile Leu Ser Val Gln Ala Glu
            20                  25                  30

Glu Gln Lys Leu Ile Ser Glu Glu Asp
        35                  40

<210> SEQ ID NO 39
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Asp Leu Leu Arg Lys Arg Arg Glu Gln Leu Lys His Lys Leu Glu
1               5                   10                  15

Gln Leu Arg Lys Gly Glu Leu Asn Ser Lys Leu Glu Gly Lys Pro Ile
            20                  25                  30

Pro Asn Pro Leu Leu Gly Leu Asp
        35                  40

<210> SEQ ID NO 40
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 40

Leu Asp Ser Thr Arg Thr Gly His His His His His His
1               5                   10

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 41

His His His His His His
1               5

<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Lys Pro Ile Pro Asn Pro Leu Leu Gly Leu Asp Ser Thr
1               5                   10

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ile Pro Asn Pro Leu Leu Gly Leu Asp
1               5

<210> SEQ ID NO 44
<211> LENGTH: 9
<212> TYPE: PRT
<213> ORGANISM: Human immunodeficiency virus 1

<400> SEQUENCE: 44

Arg Lys Lys Arg Arg Gln Arg Arg Arg
1               5
```

NANOPARTICLE FORMULATIONS

PRIORITY

This application claims priority to U.S. Provisional Application Ser. No. 62/429,466, filed Dec. 2, 2016, the content of which is incorporated by reference in its entirety.

SEQUENCE LISTING

The instant application contains a Sequence Listing which has been submitted electronically in ASCII format and is hereby incorporated by reference in its entirety. Said ASCII copy, created on Jan. 16, 2018, is named 106417-0286_SL.txt and is 39,189 bytes in size.

BACKGROUND

The quaternary structure of polypeptides can greatly influence their physicochemical and biological character. Protein aggregation, or non-native aggregation, refers to the process by which protein molecules assemble into stable complexes composed of two or more proteins, with the individual proteins denoted as the monomer. Aggregates are often held together by strong non-covalent contacts, and require some degree of conformational distortion (unfolding or misfolding) in order to present key stretches of amino acids that form the strong contacts between monomers. While aggregation tends to increase the stability of protein, it often does so at the cost of biological activity of the protein, decreased uniformity of the composition, and can, in some cases, increase the immunogenicity of the protein. These properties adversely affect the ability to use such proteins as a biologic for treatment.

SUMMARY

The present technology relates to the controlled assembly of MYC-containing polypeptides into populations of biologically active particles of defined size range. Methods are provided herein for the production of stable preparations of MYC-containing nanoparticles that retain biologic activity. Also provided are methods using the biologically active particles for treatment, including in vitro and in vivo methods of treating cells.

Disclosed herein are compositions comprising MYC-containing polypeptides formulated as biologically active, stable nanoparticles. In some embodiments, the MYC-containing polypeptides comprise a fusion peptide, wherein the fusion peptide comprises: (i) a protein transduction domain; (ii) a MYC polypeptide sequence, and wherein the nanoparticles exhibit the biological activity of MYC. In some embodiments, the fusion peptide comprises SEQ ID NO: 1. In some embodiments, the fusion peptide comprises SEQ ID NO: 10.

Provided herein, in certain embodiments, are compositions comprising a population of biologically active nanoparticles comprising one or more MYC-containing polypeptides. In some embodiments, the number average diameter of the biologically active nanoparticles is between about 80 nm and about 150 nm. In some embodiments, pH of the formulation is at least about pH 6.0, but is no greater than about pH 8. In some embodiments, contacting an anti-CD3 or anti-CD28 activated T-cell with the MYC-containing polypeptide nanoparticle composition under conditions suitable for T-cell proliferation, augments one or more of the activation, survival, or proliferation of the T-cell compared with an anti-CD3 or anti-CD28 activated T-cell that is not contacted with the MYC polypeptide-containing composition. In some embodiments, the MYC polypeptide is acetylated. In some embodiments, the MYC-containing polypeptide comprises a MYC fusion peptide, comprising a protein transduction domain linked to a MYC polypeptide. In some embodiments, the MYC fusion peptide further comprises one or more molecules that link the protein transduction domain and the MYC polypeptide. In some embodiments, the MYC-containing polypeptide comprises a MYC fusion peptide with the following general structure: protein transduction domain-X-MYC sequence, wherein -X- is molecule that links the protein transduction domain and the MYC sequence. In some embodiments, the protein transduction domain sequence is a TAT protein transduction domain sequence. In some embodiments, the TAT protein transduction domain sequence is selected from the group consisting of TAT[48-57] and TAT[57-48]. In some embodiments, the MYC polypeptide is a MYC fusion peptide comprising SEQ ID NO: 1. In some embodiments, the MYC polypeptide is a MYC fusion peptide comprising SEQ ID NO: 10. In some embodiments, the nanoparticles have a number average diameter of between about 80 nm and about 150 nm. In some embodiments, the nanoparticles have a number average diameter of between about 100 nm and about 110 nm. In some embodiments, the composition further comprises, a pharmaceutically acceptable excipient. In some embodiments, the composition is formulated for topical administration, oral administration, parenteral administration, intranasal administration, buccal administration, rectal administration, or transdermal administration.

Also provided herein, in certain embodiments, are methods of increasing one or more of activation, survival, or proliferation of one or more immune cells or increasing an immune response in a subject in need thereof by administering a therapeutically effective amount of a composition provided herein comprising a population of biologically active nanoparticles comprising one or more MYC-containing polypeptides. In some embodiments, the one or more immune cells comprise one or more anergic immune cells. In some embodiments, the one or more immune cells are T cells. In some embodiments, the T cells are selected from the group consisting of naive T cells, CD4+ T cells, CD8+ T cells, memory T cells, activated T cells, anergic T cells, tolerant T cells, chimeric B cells, and antigen-specific T cells. In some embodiments, the one or more immune cells are B cells. In some embodiments, the B cells are selected from the group consisting of naive B cells, plasma B cells, activated B cells, memory B cells, anergic B cells, tolerant B cells, chimeric B cells, and antigen-specific B cells. Also provided herein, in certain embodiments, are methods of priming hematopoietic stem cells to enhance engraftment, following hematopoietic stem cell transplantation (HSCT) comprising, contacting one or more hematopoietic stem cells, in vitro, with the composition provided herein comprising a population of biologically active nanoparticles comprising one or more MYC-containing polypeptides prior to transplantation of the hematopoietic stem cells.

Also provided herein, in certain embodiments, are methods for the preparation of a population of biologically active nanoparticles comprising one or more MYC-containing polypeptides, the method comprising: (a) solubilizing MYC-containing polypeptides in a solubilization solution comprising a concentration of a denaturing agent to provide solubilized MYC-containing polypeptides; (b) performing a first refolding step on the solubilized MYC-containing polypeptides with a first refold buffer comprising about 0.35 to about 0.65 the concentration of the denaturing agent of step (a) and about 100 mM to about 1M alkali metal salt and/or alkaline metal salt for at least about 30 to 180 minutes to provide a first polypeptide mixture; (c) performing a second refolding step on the first polypeptide mixture with a second refold buffer comprising about 0.10 to about 0.30 the concentration of the denaturing agent of step (b) and about 100 mM to 1M alkali metal salt and/or alkaline metal salt at least about 30 to 180 minutes to provide a second polypeptide mixture; (e) performing a third refolding step on the second polypeptide mixture with a third refold buffer comprising about 100 mM to 1M alkali metal salt and/or alkaline metal salt for at least about 30 to 180 minutes; and (f) maintaining the MYC-containing polypeptides in the third refold buffer for a period of time sufficient to produce biologically active nanoparticles having a number average diameter of between about 80 nm and about 150 nm, wherein contacting an anti-CD3 or anti-CD28 activated T-cell with the biologically active nanoparticles under conditions suitable for T-cell proliferation, augments one or more of the activation, survival, or proliferation of the T-cell compared with an anti-CD3 or anti-CD28 activated T-cell that is not contacted with the biologically active nanoparticles. In some embodiments, the first refolding step, second refolding step, and/or third refolding step comprise performing the step by buffer exchange. In some embodiments, buffer exchange is performed using tangential flow filtration. In some embodiments, the alkali metal salt comprises one more of a sodium salt, a lithium salt, and a potassium salt. In some embodiments, the alkali metal salt comprises one or more of sodium chloride (NaCl), sodium bromide, sodium bisulfate, sodium sulfate, sodium bicarbonate, sodium carbonate, lithium chloride, lithium bromide, lithium bisulfate, lithium sulfate, lithium bicarbonate, lithium carbonate, potassium chloride, potassium bromide, potassium bisulfate, potassium sulfate, potassium bicarbonate, and potassium carbonate. In some embodiments, the alkaline salt comprises one more of a magnesium salt and a calcium salt. In some embodiments, the alkaline metal salt comprises one or more of magnesium chloride, magnesium bromide, magnesium bisulfate, magnesium sulfate, magnesium bicarbonate, magnesium carbonate, calcium chloride, calcium bromide, calcium bisulfate, calcium sulfate, calcium bicarbonate, and calcium carbonate. In some embodiments, the alkali metal salt comprises sodium chloride (NaCl). In some embodiments, the first, second, and/or third refold buffers comprise about 500 mM NaCl. In some embodiments, the concentration of denaturing agent in step (a) is from about 1 M to about 10 M. In some embodiments, the denaturing agent comprises one or more of guanidine, guanidine hydrochloride, guanidine chloride, guanidine thiocyanate, urea, thiourea, lithium perchlorate, magnesium chloride, phenol, betain, sarcosine, carbamoyl sarcosine, taurine, dimethylsulfoxide (DMSO); alcohols such as propanol, butanol and ethanol; detergents, such as sodium dodecyl sulfate (SDS), N-lauroyl sarcosine, Zwittergents, non-detergent sulfobetains (NDSB), TRITON X-100, NONIDET™ P-40, the TWEEN™ series and BRIJ™ series; hydroxides such as sodium and potassium hydroxide. In some embodiments, the first refold buffer, the second refold buffer, and/or third refold buffer each independently comprise a buffering agent. In some embodiments, the buffering agent comprises one or more of TRIS (Tris[hydroxymethyl]aminomethane), HEPPS (N-[2-Hydroxyethyl]piperazine-N'-[3-propane-sulfonic acid]), CAPSO (3-[Cyclohexylamino]-2-hydroxy-1-propanesulfonic acid), AMP (2-Amino-2-methyl-1propanol), CAPS (3-[Cyclohexylamino]-1-propanesulfonic acid), CHES (2[N-Cyclohexylamino]ethanesulfonic acid), arginine, lysine, and sodium borate. In some embodiments, the buffering agent is independently present at a concentration from about 1 mM to about 1M. In some embodiments, the first refold buffer, second refold buffer, and/or third refold buffer each independently comprise an oxidizing agent and a reducing agent, wherein a mole ratio of oxidizing reagent to reducing agent is from about 2:1 to about 20:1. In some embodiments, the oxidizing agent comprises cysteine, glutathione disulfide ("oxidized glutathione"), or both. In some embodiments, the oxidizing agent is included in a concentration from about 0.1 mM to about 10 mM. In some embodiments, the reducing agent comprises one or more of beta-mercaptoethanol (BME), dithiothreitol (DTT), dithioerythritol (DTE), tris(2-carboxyethyl)phosphine, (TCEP), cystine, cysteamine, thioglycolate, glutathione, and sodium borohydride. In some embodiments, the reducing agent is included in a concentration from about 0.02 mM to about 2 mM. In some embodiments, the denaturing agent comprises urea. In some embodiments, the denaturing agent comprises 6-8M urea. In some embodiments, the first, second, and/or third refold buffers comprise glutathione and/or oxidized glutathione. In some embodiments, the first, second, and/or third refold buffers comprise 5 mM glutathione and/or 1 mM oxidized glutathione. In some embodiments, the first, second, and/or third refold buffers comprise glycerol. In some embodiments, the step (f) is performed for at least 5 hours. In some embodiments, the step (f) is performed for at least 10 hours. In some embodiments, the step (f) is performed for 10-12 hours. In some embodiments, the step (f) further comprises stirring the MYC-containing polypeptides in the third refold buffer at less than 1000 rpm.

In some embodiments, the methods provided herein further comprise isolating a recombinant MYC-containing polypeptide from a microbial host cell. In some embodiments, the microbial host cell is *E. coli*. In some embodiments, isolating a recombinant MYC-containing polypeptide from a microbial host cell comprises expressing the MYC-containing polypeptide from an inducible promoter. In some embodiments, isolating a recombinant MYC-containing polypeptide from a microbial host cell comprises purifying the MYC-containing polypeptide using affinity chromatography and/or anion exchange chromatography. In some embodiments, the MYC-containing polypeptide is acetylated.

In some embodiments, the MYC-containing polypeptides of the nanoparticle compositions and methods for the production thereof provided herein are recombinant polypeptides. In some embodiments, the MYC-containing polypeptide of the nanoparticle compositions provided herein comprises a MYC fusion peptide, comprising a protein transduction domain linked to a MYC polypeptide. In some embodiments, the MYC fusion peptide further comprises one or more molecules that link the protein transduction domain and the MYC polypeptide. In some embodiments, the MYC-containing polypeptide comprises a MYC fusion peptide with the following general structure: protein transduction domain-X-MYC sequence, wherein -X- is molecule that links the protein transduction domain and the MYC sequence. In some embodiments, protein transduction domain sequence is a TAT protein transduction domain sequence. In some embodiments, TAT protein transduction domain sequence is selected from the group consisting of TAT[48-57] and TAT[57-48]. In some embodiments, the MYC-containing polypeptide is a MYC fusion peptide comprising SEQ ID NO: 1. In some embodiments, the MYC-containing polypeptide is a MYC fusion peptide comprising SEQ ID NO: 10. In some embodiments, the nanoparticles have a number average diameter from about 80 nm and about 150 nm. In some embodiments, the nanoparticles have a number average diameter from about 100 nm and about 110 nm.

In an exemplary embodiment, provided herein is a method for the preparation of a population of biologically active nanoparticles comprising one or more MYC-containing polypeptides, the method comprising: (a) denaturing MYC-containing polypeptides in a buffered solubilization solution comprising 6-8M Urea to provide denatured MYC-containing polypeptides; (b) performing a first refolding step on the denatured MYC-containing polypeptides with a first refold buffer comprising about 3M Urea and about 500 mM NaCl for at least about 120 minutes to provide a first polypeptide mixture; (c) performing a second refolding step on the first polypeptide mixture by buffer exchange with a second refold buffer comprising about 1.5M Urea and about 500 mM NaCl at least about 120 minutes to provide a second polypeptide mixture; (d) performing a third refolding step on the second polypeptide mixture by buffer exchange with a third refold buffer comprising about 500 mM NaCl for at least about 120 minutes; and (f) maintaining the MYC-containing polypeptides in the third refold buffer for a period of time sufficient to produce biologically active nanoparticles having a number average diameter of between about 80 nm and about 150 nm, wherein contacting an anti-CD3 or anti-CD28 activated T-cell with the biologically active nanoparticles under conditions suitable for T-cell proliferation, augments one or more of the activation, survival, or proliferation of the T-cell compared with an anti-CD3 or anti-CD28 activated T-cell that is not contacted with the biologically active nanoparticles.

BRIEF DESCRIPTION OF THE DRAWINGS

FIG. 1A shows the proliferation of T-cells in the buffer control sample. FIG. 1B shows flow the proliferation of T-cells incubated for 24 h with MYC-containing nanoparticle formulation C2A.

FIG. 2A and 2B show the chromatograms obtained from the analysis of Formulation F01 and Formulation F02, respectively. Trace t1 and t2 were obtained from samples stored at 25° C. Trace t2* and t4* were obtained from samples stored at 5° C. Time (t) was measured in weeks and is shown in the numerical value that follows the t (i.e., t1=one week, t2=two weeks etc.).

FIG. 4A shows retention volume (ml) as a function of refractive index (left ordinate, RV×RI) or molecular size (right ordinate, RV×MW). FIG. 4B shows chromatograms showing fractionation of biologically active MYC-containing nanoparticle formulations and a biologically inactive formulation.

FIG. 5A depicts size distribution of MYC-containing nanoparticle formulation C2A by DLS. FIG. 5B depicts size distribution of non-biologically active MYC-containing nanoparticle formulation R149 tested at a concentration of 0.5 mg/ml. FIG. 5C depicts the nanoparticle size distribution of biologically active MYC-containing nanoparticle formulation C12 tested at a concentration of 0.5 mg/ml. FIG. 5D shows the nanoparticle size distribution of biologically active MYC-containing nanoparticle formulation C13 tested at a concentration of 0.5 mg/ml.

FIG. 6A shows the tracings observed from triplicate determination of nanoparticle formulation C2A. FIG. 6B shows the consensus tracing of the triplicate determinations derived from the analysis of C2A nanoparticle formulation shown in FIG. 6A.

FIG. 10A shows the full chromatogram. FIG. 10B and FIG. 10C show two different zoom views of full chromatogram in FIG. 10A.

FIG. 16B shows the chromatogram for TAT-MYC. TAT-MYC protein complex elutes between minutes 6 and 7. Smaller protein multimers and excipient elute between minutes 8 and 15. FIG. 16B shows the chromatograms for TAT-3AMYC compared to the functional TAT-MYC protein preparations. The bulk of the non-functional TAT-3AMYC protein preparation is comprised of smaller protein multimers and excipient peaks can be seen eluting between minute 8 and 17.

DETAILED DESCRIPTION

Figure 1B:
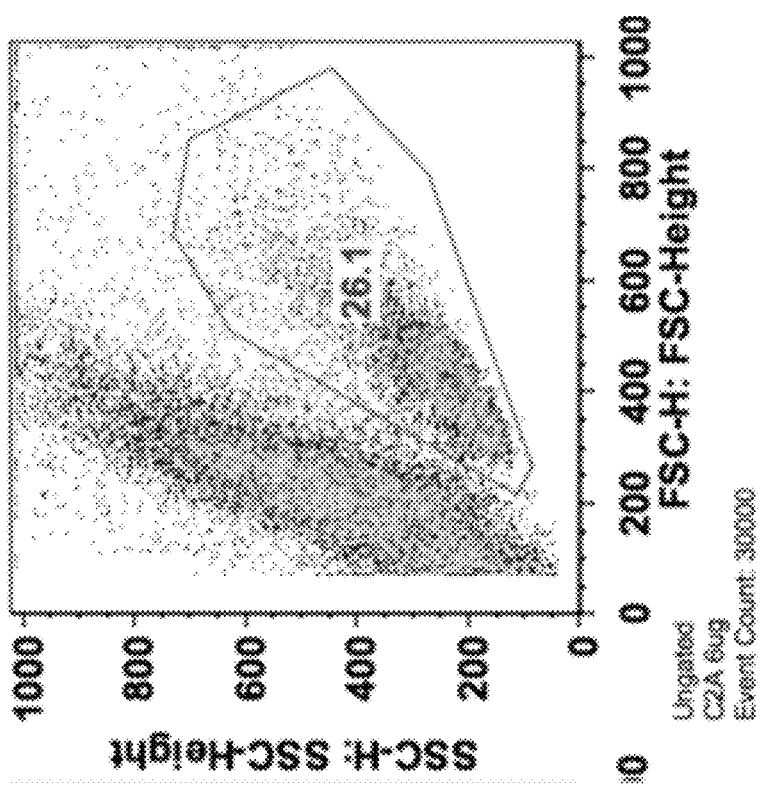
FIG. 1A and FIG. 1B show the effect of MYC-containing nanoparticle formulation C2A on proliferation of anti-CD3 and anti-CD28 activated T-cells using flow cytometry techniques.

The present disclosure is not to be limited in terms of the particular embodiments described in this application, which are intended as single illustrations of individual aspects of the disclosure. All the various embodiments of the present disclosure will not be described herein. Many modifications and variations of the disclosure can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled.

It is to be understood that the present disclosure is not limited to particular uses, methods, reagents, compounds, compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Unless defined otherwise, all technical and scientific terms used herein have the same meaning as commonly understood by one of ordinary skill in the art to which this disclosure belongs.

I. Definitions

The terminology used herein is for the purpose of describing particular embodiments only and is not intended to be limiting of the disclosure. As used herein, the singular forms "a", "an" and "the" are intended to include the plural forms as well, unless the context clearly indicates otherwise.

As used herein, the term "about" means that a value may vary +/−20%, +/−15%, +/−10% or +/−5% and remain within the scope of the present disclosure. For example, "a concentration of about 200 IU/mL" encompasses a concentration between 160 IU/mL and 240 IU/mL.

As used herein, the term "administration" of an agent to a subject includes any route of introducing or delivering the agent to a subject to perform its intended function. Administration can be carried out by any suitable route, including intravenously, intramuscularly, intraperitoneally, or subcutaneously. Administration includes self-administration and the administration by another.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refers to agents that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. In some embodiments, amino acids forming a polypeptide are in the D form. In some embodiments, the amino acids forming a polypeptide are in the L form. In some embodiments, a first plurality of amino acids forming a polypeptide are in the D form and a second plurality are in the L form.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The terms "polypeptide," "peptide," and "protein" are used interchangeably herein to refer to a polymer of amino acid residues. The terms apply to naturally occurring amino acid polymers as well as amino acid polymers in which one or more amino acid residues is a non-naturally occurring amino acid, e.g., an amino acid analog. The terms encompass amino acid chains of any length, including full length proteins, wherein the amino acid residues are linked by covalent peptide bonds.

As used herein, a "control" is an alternative sample used in an experiment for comparison purpose. A control can be "positive" or "negative." For example, where the purpose of the experiment is to determine a correlation of the efficacy of a therapeutic agent for the treatment for a particular type of disease, a positive control (a composition known to exhibit the desired therapeutic effect) and a negative control (a subject or a sample that does not receive the therapy or receives a placebo) are typically employed.

As used herein, the term "effective amount" or "therapeutically effective amount" refers to a quantity of an agent sufficient to achieve a desired therapeutic effect. In the context of therapeutic applications, the amount of a therapeutic peptide administered to the subject may depend on the type and severity of the infection and on the characteristics of the individual, such as general health, age, sex, body weight and tolerance to drugs. It may also depend on the degree, severity and type of disease. The skilled artisan will be able to determine appropriate dosages depending on these and other factors.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample. In one aspect, the expression level of a gene from one sample may be directly compared to the expression level of that gene from a control or reference sample. In another aspect, the expression level of a gene from one sample may be directly compared to the expression level of that gene from the same sample following administration of the compositions disclosed herein. The term "expression" also refers to one or more of the following events: (1) production of an RNA template from a DNA sequence (e.g., by transcription) within a cell; (2) processing of an RNA transcript (e.g., by splicing, editing, 5' cap formation, and/or 3' end formation) within a cell; (3) translation of an RNA sequence into a polypeptide or protein within a cell; (4) post-translational modification of a polypeptide or protein within a cell; (5) presentation of a polypeptide or protein on the cell surface; and (6) secretion or presentation or release of a polypeptide or protein from a cell.

The term "linker" refers to synthetic sequences (e.g., amino acid sequences) that connect or link two sequences, e.g., that link two polypeptide domains. In some embodiments, the linker contains 1, 2, 3, 4, 5, 6, 7, 8, 9, or 10 of amino acid sequences.

The terms "lyophilized," "lyophilization" and the like as used herein refer to a process by which the material (e.g., nanoparticles) to be dried is first frozen and then the ice or frozen solvent is removed by sublimation in a vacuum environment. An excipient may be included in pre-lyophilized formulations to enhance stability of the lyophilized product upon storage. The lyophilized sample may further contain additional excipients.

As used herein the term immune cell refers to any cell that plays a role in the immune response. Immune cells are of hematopoietic origin, and include lymphocytes, such as B cells and T cells; natural killer cells; myeloid cells, such as monocytes, macrophages, dendritic cells, eosinophils, neutrophils, mast cells, basophils, and granulocytes.

The term "lymphocyte" refers to all immature, mature, undifferentiated and differentiated white lymphocyte populations including tissue specific and specialized varieties. It encompasses, by way of non-limiting example, B cells, T cells, NKT cells, and NK cells. In some embodiments, lymphocytes include all B cell lineages including pre-B cells, progenitor B cells, early pro-B cells, late pro-B cells, large pre-B cells, small pre-B cells, immature B cells, mature B cells, plasma B cells, memory B cells, B-1 cells, B-2 cells and anergic AN1/T3 cell populations.

As used herein, the term T-cell includes naïve T cells, CD4+ T cells, CD8+ T cells, memory T cells, activated T cells, anergic T cells, tolerant T cells, chimeric B cells, and antigen-specific T cells.

The term "B cell" or "B cells" refers to, by way of non-limiting example, a pre-B cell, progenitor B cell, early pro-B cell, late pro-B cell, large pre-B cell, small pre-B cell, immature B cell, mature B cell, naïve B cells, plasma B cells, activated B cells, anergic B cells, tolerant B cells, chimeric B cells, antigen-specific B cells, memory B cell, B-1 cell, B-2 cells and anergic AN1/T3 cell populations. In some embodiments, the term B cell includes a B cell that expresses an immunoglobulin heavy chain and/or light chain on its cells surface. In some embodiments, the term B cell includes a B cell that expresses and secretes an immunoglobulin heavy chain and/or light chain. In some embodiments, the term B cell includes a cell that binds an antigen on its cell-surface. In some embodiments disclosed herein, B cells or AN1/T3 cells are utilized in the processes described. In certain embodiments, such cells are optionally substituted with any animal cell suitable for expressing, capable of expressing (e.g., inducible expression), or capable of being differentiated into a cell suitable for expressing an antibody including, e.g., a hematopoietic stem cell, a naive B cell, a B cell, a pre-B cell, a progenitor B cell, an early Pro-B cell, a late pro-B cell, a large pre-B cell, a small pre-B cell, an immature B cell, a mature B cell, a plasma B cell, a memory B cell, a B-1 cell, a B-2 cell, an anergic B cell, or an anergic AN1/T3 cell.

The terms "MYC" and "MYC gene" are synonyms. They refer to a nucleic acid sequence that encodes a MYC polypeptide. A MYC gene comprises a nucleotide sequence of at least 120 nucleotides that is at least 60% to 100% identical or homologous, e.g., at least 60, 65%, 70%, 75%, 80%, 85%, 86%, 87%, 88%, 90%, 91%, 92%, 94%, 95%, 96%, 97%, 98%, or any other percent from about 70% to about 100% identical to sequences of NCBI Accession Number NM_002467.5. In some embodiments, the MYC gene is a proto-oncogene. In certain instances, a MYC gene is found on chromosome 8, at 8q24.21. In certain instances, a MYC gene begins at 128,816,862 bp from pter and ends at 128,822,856 bp from pter. In certain instances, a MYC gene is about 6 kb. In certain instances, a MYC gene encodes at least eight separate mRNA sequences—5 alternatively spliced variants and 3 unspliced variants.

The terms "MYC protein," "MYC polypeptide," and "MYC sequence" are synonyms and refer to the polymer of amino acid residues disclosed in NCBI Accession Number NP_002458.2 (provided below) or UniProtKB/Swiss-Prot: P01106.1, which is human myc isoform 2, and functional homologs, variants, analogs or fragments thereof. This sequence is shown below.

(SEQ ID NO: 2)
MDFFRVVENQQPPATMPLNVSFTNRNYDLDYDSVQPYFYCDEEENFYQQQ

QQSELQPPAPSEDIWKKFELLPTPPLSPSRRSGLCSPSYVAVTPFSLRGD

NDGGGGSFSTADQLEMVTELLGGDMVNQSFICDPDDETFIKNIIIQDCMW

SGFSAAAKLVSEKLASYQAARKDSGSPNPARGHSVCSTSSLYLQDLSAAA

SECIDPSVVFPYPLNDSSSPKSCASQDSSAFSPSSDSLLSSTESSPQGSP

EPLVLHEETPPTTSSDSEEEQEDEEEIDVVSVEKRQAPGKRSESGSPSAG

GHSKPPHSPLVLKRCHVSTHQHNYAAPPSTRKDYPAAKRVKLDSVRVLRQ

-continued
ISNNRKCTSPRSSDTEENVKRRTHNVLERQRRNELKRSFFALRDQIPELE

NNEKAPKVVILKKATAYILSVQAEEQKLISEEDLLRKRREQLKHKLEQLR

NSCA

In some embodiments, the MYC polypeptide is a complete MYC polypeptide sequence. In some embodiments, the MYC polypeptide is a partial MYC polypeptide sequence. In some embodiments, the MYC polypeptide is c-MYC. In some embodiments, the MYC polypeptide sequence comprises the sequence shown below:

(SEQ ID NO: 3)
MDFFRVVENQQPPATMPLNVSFTNRNYDLDYDSVQPYFYCDEEENFYQQQ

QQSELQPPAPSEDIWKKFELLPTPPLSPSRRSGLCSPSYVAVTPFSLRGD

NDGGGGSFSTADQLEMVTELLGGDMVNQSFICDPDDETFIKNIIIQDCMW

SGFSAAAKLVSEKLASYQAARKDSGSPNPARGHSVCSTSSLYLQDLSAAA

SECIDPSVVFPYPLNDSSSPKSCASQDSSAFSPSSDSLLSSTESSPQGSP

EPLVLHEETPPTTSSDSEEEQEDEEEIDVVSVEKRQAPGKRSESGSPSAG

GHSKPPHSPLVLKRCHVSTHQHNYAAPPSTRKDYPAAKRVKLDSVRVLRQ

ISNNRKCTSPRSSDTEENVKRRTHNVLERQRRNELKRSFFALRDQIPELE

NNEKAPKVVILKKATAYILSVQAEEQKLISEEDLLRKRREQLKHKLEQLR

KGELNSKLE.

In some embodiments, the MYC polypeptide sequence comprises the sequence shown below:

(SEQ ID NO: 4)
PLNVSFTNRNYDLDYDSVQPYFYCDEEENFYQQQQQSELQPPAPSEDIWK

KFELLPTPPLSPSRRSGLCSPSYVAVTPFSLRGDNDGGGGSFSTADQLEM

VTELLGGDMVNQSFICDPDDETFIKNIIIQDCMWSGESAAAKLVSEKLAS

YQAARKDSGSPNPARGHSVCSTSSLYLQDLSAAASECIDPSVVFPYPLND

SSSPKSCASQDSSAFSPSSDSLLSSTESSPQGSPEPLVLHEETPPTTSSD

SEEEQEDEEEIDVVSVEKRQAPGKRSESGSPSAGGHSKPPHSPLVLKRCH

VSTHQHNYAAPPSTRKDYPAAKRVKLDSVRVLRQISNNRKCTSPRSSDTE

ENVKRRTHNVLERQRRNELKRSFFALRDQIPELENNEKAPKVVILKKATA

YILSVQAEEQKLISEEDLLRKRREQLKHKLEQLR.

In some embodiments, the MYC polypeptide sequence comprises a MYC polypeptide sequence from a non-human species. In some embodiments, the non-human species is selected from the group consisting of ape, monkey, mouse, rat, hamster, guinea pig, rabbit, cat, dog, pig, sheep, goat, cow, and horse species. In some embodiments, the MYC polypeptide sequence comprises the sequence shown below, which is from *Chlorocebus sabaeus* (green monkey) (XP_007999715.1):

MPLNVSFTNRNYDLDYDSVQPYFYCDEEENFYQQQQQSELQPPAPSEDIW

KKFELLPTPPLSPSRRSGLCSPSYVAVTPFSPRGDNDGGGGSFSTADQLE

MVTELLGGDMVNQSFICDPDDETFIKNIIIQDCMWSGESAAAKLVSEKLA

SYQAARKDSGSPNPARGHSVCSTSSLYLQDLSAAASECIDPSVVFPYPLN

-continued
DSSSPKSCASPDSSAFSPSSDSLLSSTESSPQASPEPLVLHEETPPTTSS

DSEEEQEDEEEIDVVSVEKRQAPGKRSESGSPSAGGHSKPPHSPLVLKRC

HVSTHQHNYAAPPSTRKDYPAAKRVKLDSVRVLRQISNNRKCTSPRSSDT

EENVKRRTHNVLERQRRNELKRSFFALRDQIPELENNEKAPKVVILKKAT

AYILSVQAEEQKLISEKDLLRKRREQLKHKLEQLRNSCA

In some embodiments, the MYC polypeptide sequence comprises the sequence shown below:

(SEQ ID NO: 9)
PLNVSFTNRNYDLDYDSVQPYFYCDEEENFYQQQQQSELQPPAPSEDIWK

KFELLPTPPLSPSRRSGLCSPSYVAVTPFSLRGDNDGGGGSFSTADQLEM

VTELLGGDMVNQSFICDPDDETFIKNIIIQDCMWSGFSAAAKLVSEKLAS

YQAARKDSGSPNPARGHSVCSTSSLYLQDLSAAASECIDPSVVFPYPLND

SSSPKSCASQDSSAFSPSSDSLLSSTESSPQASPEPLVLHEETPPTTSSD

SEEEQEDEEEIDVVSVEKRQAPGKRSESGSPSAGGHSKPPHSPLVLKRCH

VSTHQHNYAAPPSTRKDYPAAKRVKLDSVRVLRQISNNRKCTSPRSSDTE

ENVKRRTHNVLERQRRNELKRSFFALRDQIPELENNEKAPKVVILKKATA

YILSVQAEEQKLISEKDLLRKRREQLKHKLEQLR.

In some embodiments, a MYC polypeptide comprises an amino acid sequence that is at least 40% to 100% identical, e.g., at least 40%, 45%, 50%, 55%, 60%, 65%, 70%, 75%, 80%, 81%, 82%, 83%, 84%, 85%, 86%, 87%, 88%, 90%, 91%, 92%, 94%, 95%, 96%, 97%, 98%, 99%, or any other percent from about 40% to about 100% identical to the sequence of NCBI Accession Number NP002458.2 (SEQ ID NO: 2). In some embodiments, a MYC polypeptide refers to a polymer of 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454 consecutive amino acids of NP002458.2 (SEQ ID NO: 2). In some embodiments, a MYC polypeptide refers to a polymer of 435 amino acids of NP002458.2 (SEQ ID NO: 2) that has not undergone any post-translational modifications. In some embodiments, a MYC polypeptide refers to a polymer of 435 amino acids of NP002458.2 (SEQ ID NO: 2) that has undergone post-translational modifications. In some embodiments, the MYC polypeptide is 48,804 kDa. In some embodiments, the MYC polypeptide contains a basic Helix-Loop-Helix Leucine Zipper (bHLH/LZ) domain. In some embodiments, the bHLH/LZ domain comprises the sequence of ELKRSFFALRDQIPELENNEKAPKVVILK-KATAYILSVQAEEQKLISEEDLLRKRREQLKH KLEQLR (SEQ ID NO: 5). In some embodiments, the MYC polypeptide is a transcription factor (e.g., Transcription Factor 64). In some embodiments, the MYC polypeptide contains a E-box DNA binding domain. In some embodiments, the MYC polypeptide binds to a sequence comprising CACGTG. In some embodiments, the MYC polypeptide promotes one or more of cell survival and/or proliferation. In some embodiments, a MYC polypeptide includes one or more of those described above, and includes one or more post-translational modifications (e.g., acetylation). In some embodiments, the MYC polypeptides comprise one or more additional amino acid residues at the N-terminus or C-terminus of the polypeptide. In some embodiments, the MYC polypeptides are fusion proteins. In some embodiments, the MYC polypeptides are linked to one or more additional peptides at the N-terminus or C-terminus of the polypeptide.

Proteins suitable for use in the methods described herein also includes functional variants, including proteins having between 1 to 15 amino acid changes, e.g., 1, 2, 3, 4, 5, 6, 7, 8, 9, 10, 11, 12, 13, 14, or 15 amino acid substitutions, deletions, or additions, compared to the amino acid sequence of any protein described herein. In other embodiments, the altered amino acid sequence is at least 75% identical, e.g., 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the amino acid sequence of any protein inhibitor described herein. Such sequence-variant proteins are suitable for the methods described herein as long as the altered amino acid sequence retains sufficient biological activity to be functional in the compositions and methods described herein. Where amino acid substitutions are made, the substitutions may be conservative amino acid substitutions. Among the common, naturally occurring amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff et al., (1992), *Proc. Natl Acad. Sci. USA*, 89:10915-10919). Accordingly, the BLOSUM62 substitution frequencies are used to define conservative amino acid substitutions that, in some embodiments, are introduced into the amino acid sequences described or disclosed herein. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3).

The phrases "E-box sequence" and "enhancer box sequence" are used interchangeably herein and mean the nucleotide sequence CANNTG, wherein N is any nucleotide. In certain instances, the E-box sequence comprises CACGTG. In certain instances, the basic helix-loop-helix domain of a transcription factor encoded by MYC binds to the E-box sequence. In certain instances the E-box sequence is located upstream of a gene (e.g., p21, Bcl-2, or ornithine decarboxylase). In certain instances, the MYC polypeptide contains an E-box DNA binding domain. In certain instances, the E-box DNA binding domain comprises the sequence of KRRTHNVLERQRRN (SEQ ID NO: 6). In certain instances, the binding of the transcription factor encoded by MYC to the E-box sequence, allows RNA polymerase to transcribe the gene downstream of the E-box sequence.

The term "MYC activity" or "MYC biological activity" or "biologically active MYC" includes one or more of enhancing or inducing cell survival, cell proliferation, and/or antibody production. By way of example and not by way of limitation, MYC activity includes enhancement of expansion of anti-CD3 and anti-CD28 activated T-cells and/or increased proliferation of long-term self-renewing hematopoietic stem cells. MYC activity also includes entry into the nucleus of a cell, binding to a nucleic acid sequence (e.g., binding an E-box sequence), and/or inducing expression of MYC target genes.

The terms "patient," "subject," "individual," and the like are used interchangeably herein, and refer to an animal, typically a mammal. In a preferred embodiment, the patient, subject, or individual is a mammal. In a particularly preferred embodiment, the patient, subject or individual is a human.

The terms "protein transduction domain (PTD)" or "transporter peptide sequence" (also known as cell permeable proteins (CPP) or membrane translocating sequences (MTS)) are used interchangeably herein to refer to small peptides that are able to ferry much larger molecules into cells independent of classical endocytosis. In some embodiments, a nuclear localization signal can be found within the protein transduction domain, which mediates further translocation of the molecules into the cell nucleus.

The terms "treating" or "treatment" as used herein covers the treatment of a disease in a subject, such as a human, and includes: (i) inhibiting a disease, i.e., arresting its development; (ii) relieving a disease, i.e., causing regression of the disease; (iii) slowing progression of the disease; and/or (iv) inhibiting, relieving, or slowing progression of one or more symptoms of the disease.

It is also to be appreciated that the various modes of treatment or prevention of medical diseases and conditions as described are intended to mean "substantial," which includes total but also less than total treatment or prevention, and wherein some biologically or medically relevant result is achieved. The treatment may be a continuous prolonged treatment for a chronic disease or a single, or few time administrations for the treatment of an acute condition.

The term "therapeutic" as used herein means a treatment and/or prophylaxis. A therapeutic effect is obtained by suppression, remission, or eradication of a disease state.

II. Compositions Comprising Nanoparticulate MYC Peptides

Disclosed herein are compositions comprising MYC-containing polypeptides formulated as biologically active, stable nanoparticles, and methods of making and using the compositions. In some embodiments, the MYC-containing polypeptide is a fusion of a MYC polypeptide and a protein transduction domain, e.g., HIV TAT. In some embodiments, the MYC fusion polypeptide also includes one or more tag sequences. In some embodiments, the MYC fusion polypeptide comprises SEQ ID NO: 1. In some embodiments, the MYC fusion polypeptide comprises SEQ ID NO: 10.

As discussed in more detail below and as illustrated in the Examples, biologically active MYC-containing polypeptide compositions of the present technology include, in some embodiments, nanoparticles of about 90-140 nm with molecular mass of about $10^4$-$10^6$ daltons. In some embodiments, the particles include about 200 molecules of MYC-containing polypeptide.

In some embodiments, the biologically active nanoparticulate compositions include post-translationally modified MYC protein. By way of example, but not by way of limitation, in some embodiments, the protein includes at least one acetyl group.

A. Expression and Purification of MYC-Containing Polypeptides

Provided herein are methods for the production of MYC-containing polypeptides for use in nanoparticle compositions provided. In the methods of the invention, MYC-containing polypeptide is recombinantly produced by microbial fermentation. In some embodiments microbial fermentation is performed in a fermentation volume of from about 1 to about 10,000 liters, for example, a fermentation volume of about 10 to about 1000 liters. The fermentation can utilize any suitable microbial host cell and culture medium. In exemplary embodiments, E. coli is utilized as the microbial host cell. In alternative embodiments, other microorganisms can be used, e.g., *S. cerevisiae, P. pastoris, Lactobacilli, Bacilli* and *Aspergilli*. In an exemplary embodiment the microbial host cell is BL-21 Star™ *E. coli* strain (Invitrogen). In an exemplary embodiment the microbial host cell is BLR DE3 *E. coli*. strain In some embodiments the host cells are modified to provide tRNAs for rare codons, which are employed to overcome host microbial cell codon bias to improve translation of the expressed proteins. In exemplary embodiments, the host cells (e.g., *E. coli*) transformed with a plasmid, such as pRARE (CamR), which express tRNAs for AGG, AGA, AUA, CUA, CCC, GGA codons. Additional, suitable plasmids or constructs for providing tRNAs for particular codons are known in the art and can be employed in the methods provided.

Integrative or self-replicative vectors may be used for the purpose of introducing the MYC-containing polypeptide expression cassette into a host cell of choice. In an expression cassette, the coding sequence for the MYC-containing polypeptide is operably linked to promoter, such as an inducible promoter. Inducible promoters are promoters that initiate increased levels of transcription from DNA under their control in response to some change in culture conditions, e.g., the presence or absence of a nutrient or a change in temperature. In some embodiments, the nucleic acid encoding the MYC-containing polypeptide is codon optimized for bacterial expression.

Exemplary promoters that are recognized by a variety of potential host cells are well known. These promoters can be operably linked to MYC-containing polypeptide-encoding DNA by removing the promoter from the source DNA, if present, by restriction enzyme digestion and inserting the isolated promoter sequence into the vector. Promoters suitable for use with microbial hosts include, but are not limited to, the β-lactamase and lactose promoter systems (Chang et al., (1978) *Nature*, 275:617-624; Goeddel et al., (1979) *Nature*, 281: 544), alkaline phosphatase, a tryptophan (trp) promoter system (Goeddel (1980) *Nucleic Acids Res.* 8: 4057; EP 36,776), and hybrid promoters such as the tac promoter (deBoer et al., (1983) *Proc. Natl. Acad. Sci. USA* 80: 21-25). Any promoter for suitable for expression by the selected host cell can be used. Nucleotide sequences for suitable are published, thereby enabling a skilled worker operably to ligate them to DNA encoding MYC-containing polypeptide (see, e.g., Siebenlist et al., (1980) *Cell* 20: 269) using linkers or adaptors to supply any required restriction sites. In exemplary embodiments, promoters for use in bacterial systems can contain a Shine-Dalgarno (S.D.) sequence operably linked to the coding sequence. In some embodiments, the inducible promoter is the lacZ promoter, which is induced with Isopropyl β-D-1-thiogalactopyranoside (IPTG), as is well-known in the art. Promoters and expression cassettes can also be synthesized de novo using well known techniques for synthesizing DNA sequences of interest. In an exemplary embodiment, the expression vector for expression of the MYC-containing polypeptides herein is pET101/D-Topo (Invitrogen).

For expression of the MYC-containing polypeptides, the microbial host containing the expression vector encoding the MYC-containing polypeptide is typically grown to high density in a fermentation reactor. In some embodiments, the reactor has controlled feeds for glucose. In some embodiments, a fermenter inoculum is first cultured in medium supplemented with antibiotics (e.g., overnight culture). The fermenter inoculum is then used to inoculate the fermenter culture for expression of the protein. At an OD600 of at least about 15, usually at least about 20, at least 25, at least about 30 or higher, of the fermenter culture, expression of the recombinant protein is induced. In exemplary embodiments, where the inducible promoter is the lacZ promoter, IPTG is added to the fermentation medium to induce expression of the MYC-containing polypeptide. Generally, the IPTG is added to the fermenter culture at an OD600 which represents logarithmic growth phase.

In certain embodiments of the methods provided, induced protein expression is maintained for around about 2 to around about 5 hours post induction, and can be from around about 2 to around about 3 hours post-induction. Longer periods of induction may be undesirable due to degradation of the recombinant protein. The temperature of the reaction mixture during induction is preferably from about 28° C. to about 37° C., usually from about 30° C. to about 37° C. In particular embodiments, induction is at about 37° C.

The MYC-containing polypeptide is typically expressed as cytosolic inclusion bodies in microbial cells. To harvest inclusion bodies, a cell pellet is collected by centrifugation of the fermentation culture following induction, frozen at −70° C. or below, thawed and resuspended in disruption buffer. The cells are lysed by conventional methods, e.g., sonication, homogenization, etc. The lysate is then resuspended in solubilization buffer, usually in the presence of urea at a concentration effective to solubilize proteins, e.g., from around about 5M, 6M, 7M, 8M, 9M or greater. Resuspension may require mechanically breaking apart the pellet and stirring to achieve homogeneity. In some embodiments, the cell pellet is directly resuspended in urea buffer and mixed until homogenous. In some embodiments, the resuspension/solubilization buffer is 8M Urea, 50 mM Phosphate pH 7.5 and the suspension is passed through a homogenizer.

In some embodiments, the homogenized suspension is sulfonylated. For example, in some embodiments, the homogenized suspension is adjusted to include 200 mM Sodium Sulfite and 10 mM Sodium Tetrathionate. The solution is then mixed at room temperature until homogeneous. The mixed lysate is then mixed for an additional period of time to complete the sulfonylation (e.g., at 2-8° C. for ≥12 hours). The sulfonylated lysate was then centrifuged for an hour. The supernatant containing the sulfonylated MYC-containing polypeptides is then collected by centrifugation and the cell pellet discarded. The supernatant is then passed through a filter, e.g., 0.22 µm membrane filter to clarify the lysate.

The solubilized protein is then purified. Purification methods may include affinity chromatography, reverse phase chromatography, gel exclusion chromatography, and the like. In some embodiments, affinity chromatography is used. For example, the protein is provided with an epitope tag or histidine 6 tag for convenient purification. In the present methods, exemplary myc-containing polypeptide comprise histidine 6 tag for purification using Ni affinity chromatography using Ni— resin.

In exemplary embodiments, the Ni— resin column is equilibrated in a buffer containing urea. In some embodiments, the equilibration buffer is 6M Urea, 50 mM Phosphate, 500 mM NaCl, and 10% Glycerol solution. The sulfonylated and clarified supernatant comprising the MYC-containing polypeptide is then loaded onto the Ni— resin column. The column is then washed with a wash buffer, e.g., 6M Urea, 50 mM Phosphate, 10% Glycerol, 500 mM NaCl, pH 7.5. The column was then washed with sequential wash buffers with decreasing salt concentration. For example, exemplary subsequent washed can include 6M Urea, 50 mM Phosphate, 10% Glycerol, and 2M NaCl, pH 7.5, followed another wash of 6M Urea, 50 mM Phosphate, 10% Glycerol, 50 mM NaCl, and 30 mM Imidazole, pH 7.5.

Following sequential application of the wash buffers the MYC-containing polypeptide is eluted from the column by addition of elution buffer, e.g., 6M Urea, 50 mM Phosphate, 10% Glycerol, and 50 mM NaCl, pH 7.5 with a gradient from 100 to 300 mM Imidazole, and collecting fractions. The protein containing fractions to be pooled are then filtered through a 0.22 µm membrane. Assessment of protein yield can be measured using any suitable method, e.g., spectrophotometry at UV wavelength 280.

In some embodiments, one or more additional purification methods can be employed to further purify the isolated MYC-containing polypeptides. In exemplary embodiments, the pooled fractions from the Ni-Sepharose chromatography step are further purified by anion exchange chromatography using a Q-Sepharose resin. In some embodiments, the pool is prepared for loading onto the Q-Sepharose column by diluting the samples to the conductivity of the Q sepharose buffer (17.52 +/−1 mS/cm) with the second wash buffer (e.g., 6M Urea, 50 mM Phosphate, 10% Glycerol, 2M NaCl, pH 7.5) from the Ni Sepharose chromatography step. The diluted pool is then loaded onto the Q-Sepharose column, followed by two chase steps using a chase buffer (e.g., 6M Urea, 50 mM Phosphate, 300 mM NaCl, and 10% Glycerol), with further sequential applications of the chase buffer until the UV trace reaches baseline, indicating that the protein has eluted from the column.

B. Refolding of MYC-Containing Polypeptides into Nanoparticles

Compositions of the present technology can be prepared from isolated MYC-containing polypeptide according to the following methods.

In some embodiments, the MYC-containing polypeptides are refolded to produce a biologically active nanoparticle. In some embodiments, the method comprises Tangential Flow Filtration (TFF), or Cross Flow Filtration. TFF is a process which uses a pump to circulate a sample across the surface of membranes (i.e. "tangential" to the membrane surface) housed in a multilevel structure (cassette). The applied transmembrane pressure acts as the driving force to transport solute and small molecules through the membrane. The cross flow of liquid over the membrane surface sweeps retaining molecules from the surface, keeping them in the circulation stream.

In some embodiments, the MYC-containing polypeptides are denatured with a denaturing agent, such as urea. The MYC-containing polypeptides are then refolded using multiple TFF steps across a ultrafiltration/diafiltration (UFDF) membrane and sequential additions of refold buffers having decreasing concentrations of the denaturing agent, e.g., urea. In some embodiments, the urea concentration of the sequential refold buffers decreases from about 3M Urea to <0.001M or no urea. In some embodiments, the sequential refold buffers comprise Phosphate, NaCl, Glycerol, GSH, (Reduced Glutathione) and GSSG (Oxidized Glutathione)). In some embodiments, the refold buffers comprise about 50 mM Phosphate. In some embodiments, the refold buffers comprise an alkali earth metal salt. In some embodiments, alkali earth metal salt is a salt of sodium (Na), lithium (Li) or potassium (K). In some embodiments, the refold buffers comprise a sodium salt, such as NaCl. In some embodiments, the refold buffers comprise between about 100 mM to 2M concentration of an alkali earth metal salt. In some embodiments, the refold buffers comprise between about 200 mM to 1M concentration of an alkali earth metal salt. In some embodiments, the refold buffers comprise between about 500 mM to 1M concentration of an alkali earth metal salt. In some embodiments, the refold buffers comprise between about 100 mM to 2M concentration of NaCl. In some embodiments, the refold buffers comprise between about 200 mM to 1M concentration of NaCl. In some embodiments, the refold buffers comprise between about 200 mM to 800 mM concentration of NaCl. In particular embodiments, the refold buffers comprise about 200-500 mM NaCl. In some embodiments, the refold buffers comprise about 500 mM NaCl. In some embodiments, the refold buffers have an osmolarity between about 300 mOsm and 1000 mOsm. In some embodiments, the refold buffers comprise about 1 to 20% Glycerol. In some embodiments, the refold buffers comprise about 10% Glycerol. In some embodiments, the refold buffers comprise about 0.1 to 50 mM GSH, (Reduced Glutathione). In some embodiments, the refold buffers comprise about 5 mM GSH, (Reduced Glutathione). In some embodiments, the refold buffers comprise about 0.1 to 50 mM GSSG (Oxidized Glutathione)). In some embodiments, the refold buffers comprise about 1 mM GSSG (Oxidized Glutathione)). In exemplary embodiments, the refold buffers comprise 50 mM Phosphate, 500 mM NaCl, 10% Glycerol, 5 mM GSH, (Reduced Glutathione), and 1 mM GSSG (Oxidized Glutathione)). In some embodiments, the refold buffers have a pH value of between about 5.0 and 8.0. In some embodiments, the refold buffers have a pH value of 7.5.

In an exemplary embodiment, the MYC-containing polypeptides are refolded using three TTF steps across a ultra-filtration/diafiltration (UFDF) membrane. In an exemplary embodiment, the first refold step involves an exchange of a refold buffer 1 (e.g., 3M Urea, 50 mM Phosphate, 500 mM NaCl, 10% Glycerol, 5 mM GSH, (Reduced Glutathione) 1 mM GSSG (Oxidized Glutathione)) over the course of about 120 minutes. In some embodiments, the second refold step involves the exchange of refold buffer 2 (1.5M Urea, 50 mM Phosphate, 500 mM NaCl, 10% Glycerol, 5 mM GSH, (Reduced Glutathione) 1 mM GSSG (Oxidized Glutathione)) over the course of approximately 120 minutes, followed by ~120 minutes of recirculation. In some embodiments, the third refold step involves the exchange of refold buffer 3 (50 mM Phosphate, 500 mM NaCl, 10% Glycerol, 5 mM GSH, (Reduced Glutathione) 1 mM GSSG (Oxidized Glutathione)) over the course of approximately 120 minutes, followed by 12 hours of recirculation.

After the final refolding step is complete, the final refold solution can be filtered through a 0.2 µm membrane and protein concentration adjusted.

Following refolding, the nanoparticle formulation contains nanoparticles having a wide range of sizes and stabilities. Thus, in some embodiments, an incubation step, or equilibration step, is performed after the third refold step. For example, in some embodiments, the refolded MYC-containing polypeptides are maintained in the third refold buffer for a period of time sufficient to produce biologically active nanoparticles having a number average diameter of between about 80 nm and about 150 nm. Without being bound by theory, it is believed that the equilibration step allows nanoparticle formulation to equilibrate into stable nanoparticles having narrower size range and more stability. In some embodiments, the number average diameter of these stable nanoparticles is between about 80 nm and about 150 nm. In some embodiments, the equilibration step is performed for a length of time of at least 5, 6, 7, 8, 9, 10, 11, or 12 hours or more. In exemplary embodiments, the equilibration is step is performed for at least or about 10-12 hours. In exemplary embodiments, the equilibration is step involves gently stirring the nanoparticle formulation of refolded MYC-containing polypeptides in the third refold buffer. In exemplary embodiments, the equilibration is step involves stirring the formulation the MYC-containing polypeptides in the third refold buffer at less than 1000 rpm.

In some embodiments, an additional exchange of final refold buffer 3 is performed to exchange the refold buffer with a formulation buffer suitable for administration, such as a buffer suitable for injection. In exemplary embodiments, refolded TAT-MYC in refold buffer 3 is dialyzed against a suitable formulation buffer. In exemplary embodiments, the refolded TAT-MYC in refold buffer 3 is dialyzed using TFF across a ultrafiltration/diafiltration (UFDF) membrane. In exemplary embodiments, the formulation buffer comprises a buffering agent. In exemplary embodiments, the buffering agent is selected from among sodium phosphate, potassium phosphate, histidine, and citrate.

In exemplary embodiments, refolded TAT-MYC is stable in a formulation having a pH value of between 5.5 and 8.0. In exemplary embodiments, refolded TAT-MYC is stable in a formulation having a pH value of between 6.0 and 8.0. In exemplary embodiments, refolded TAT-MYC is stable in a formulation having a pH value of about 6.0, about 6.5, about 7.0, about 7.5, or about 8.0. In exemplary embodiments, refolded TAT-MYC is stable in a formulation having a pH value of about pH 7.5. In exemplary embodiments, refolded TAT-MYC is stable in a formulation of about pH 7.5+/−pH 0.3.

In exemplary embodiments, the refolded TAT-MYC is stable in a formulation having an osmolality greater than 300 mOsm. In exemplary embodiments, the refolded TAT-MYC is stable in a formulation having an osmolality greater than 400 mOsm. In exemplary embodiments, the refolded TAT-MYC is stable in a formulation having an osmolality between 300 mOsm and 1000 mOsm, such as between 400 mOsm and 800 mOsm.

In exemplary embodiments, the refolded TAT-MYC is stable in a formulation comprising greater than 100 mM NaCl. In exemplary embodiments, the refolded TAT-MYC is stable in a formulation comprising greater than 150 mM NaCl. In exemplary embodiments, the NaCl concentration of a refolded TAT-MYC formulation is about 150 mM, 200 mM, 250 mM, 300 mM, 350 mM, 400 mM, 450 mM, 500 mM or 550 mM NaCl. In exemplary embodiments, the NaCl concentration of a refolded TAT-MYC formulation is about 500 mM +/−50 mM NaCl.

In some embodiments, refolded TAT-MYC can be stored up to a concentration of about 1.2 mg/mL. As used herein, "stability" with reference to a storage condition refers the ability of the refolded TAT-MYC to retain at least 20%, 30%, 40%, 50%, 60%, 70%, 80%, 90% or more of its MYC biological activity following storage, compared to the MYC biological activity of the refolded TAT-MYC prior to storage. In some embodiments, refolded TAT-MYC is stable at −80° C. for up to 2 years. In some embodiments, once thawed, refolded TAT-MYC is stable when stored at 4° C. for up to 1 month. In exemplary embodiments, once thawed, refolded TAT-MYC is stable when stored at 4° C. for up to 2 months. In exemplary embodiments, once thawed, refolded TAT-MYC is stable when stored at 4° C. for up to 3 months. In exemplary embodiments, once thawed, refolded TAT-MYC is stable when stored at 4° C. for up to 4 months. In exemplary embodiments, once thawed, refolded TAT-MYC is stable when stored at 4° C. for up to 5 months. In exemplary embodiments, once thawed, refolded TAT-MYC is stable when stored at 4° C. for up to 6 months or longer. In exemplary embodiments, once thawed, refolded TAT-MYC is stable when stored at 4° C. for up to 100 days or longer. Accordingly, the stability of the refolded TAT-MYC provided herein is significantly increased compared to the stability of a wild-type MYC polypeptide, which has a half-life of approximately 34 minutes (Kaptein et al. (1996) *JBC* 271, 18875-18884).

C. Nanoparticle Size

The size and mass of the nanoparticles of the present technology can be determined by methods well known in the art. By way of example, but not by way of limitation, such methods include size exclusion chromatography, high performance liquid chromatography, dynamic light scattering, nanoparticle tracking analysis, and electron microscopy.

In some embodiments, the average particle size of the nanoparticles in the formulation is between about 70 nm and about 140 nm, such as between 70 nm and 140 nm. In some embodiments, the average particle size of the nanoparticles in the formulation is between about 80 nm and about 120 nm, such as between 80 nm and 120 nm. In some embodiments, the average particle size of the nanoparticles in the formulation is between about 80 nm and about 110 nm, such as between 80 nm and 110 nm. In some embodiments, the average particle size of the nanoparticles in the formulation is between about 80 nm and about 90 nm, such as between 80 nm and 90 nm. In some embodiments, the average particle size of the nanoparticles in the formulation is about 84 nm or 84 nm. In some embodiments, the average particle size of the nanoparticles in the formulation is between about 100 nm and about 120 nm, such as between 100 nm and 120 nm. In some embodiments, the average particle size of the nanoparticles in the formulation is about 111 nm or 111 nm.

In some embodiments, the average molecular weight of the particles in the formulation is between about $10^3$-$10^7$ daltons, such as between $10^3$-$10^7$ daltons. In some embodiments, the average molecular weight of the particles in the formulation is between about $10^4$-$10^7$ daltons, such as between $10^4$-$10^7$ daltons. In some embodiments, the average molecular weight of the particles in the formulation is between about $10^5$-$10^7$ daltons, such as between $10^5$-$10^7$ daltons. In some embodiments, the average molecular weight of the particles in the formulation is between about $10^6$-$10^7$ daltons, such as between $10^6$-$10^7$ daltons. In some embodiments, the average molecular weight of the particles in the formulation is about $2\times10^6$ or $2\times10^6$ daltons.

In some embodiments, less than about 0.01% or less than 0.01% of the nanoparticles within the composition have a particle size greater than 200 nm, greater than 300 nm, greater than 400 nm, greater than 500 nm, greater than 600 nm, greater than 700 nm, or greater than 800 nm. In some embodiments, less than about 0.001% of the nanoparticles within the composition have a particle size greater than 200 nm, greater than 300 nm, greater than 400 nm, greater than 500 nm, greater than 600 nm, greater than 700 nm, or greater than 800 nm. In some embodiments, less than about 0.01% or less than 0.01% of the nanoparticles within the composition have a particle size greater than 800 nm. In some embodiments, less than about 0.001% or less than 0.001% of the nanoparticles within the composition have a particle size greater than 800 nm.

In some embodiments, less than about 0.01% or less than 0.01% of the nanoparticles within a formulation have a particle size less than 80 nm, less than 70 nm, less than 60 nm, less than 50 nm, less than 40 nm, less than 30 nm, less than 20 nm, or less than 10 nm. In some embodiments, less than about 0.001% or less than 0.001% of the nanoparticles within the composition have a particle size less than 80 nm, less than 70 nm, less than 60 nm, less than 50 nm, less than 40 nm, less than 30 nm, less than 20 nm, or less than 10 nm. In some embodiments, less than about 0.01% or less than 0.01% of the nanoparticles within the composition have a particle size less than 50 nm. In some embodiments, less than about 0.001% or less than 0.001% of the nanoparticles within the composition have a particle size less than 50 nm.

D. MYC Fusion Proteins

In some embodiments, the biologically active nanoparticulate compositions of MYC-containing polypeptide comprise a MYC fusion protein. In some embodiments, the MYC fusion protein comprises a protein transduction domain, a MYC polypeptide that promotes one or more of cell survival or proliferation, and optionally a protein tag domain, e.g., one or more amino acid sequences that facilitate purification of the fusion protein. In some embodiments, a cell contacted with MYC polypeptide (e.g., a nanoparticulate formulation of the present technology) exhibits increased survival time (e.g., as compared to an identical or similar cell of the same type that was not contacted with MYC), and/or increased proliferation (e.g., as compared to an identical or similar cell of the same type that was not contacted with MYC).

In some embodiments, the fusion protein comprises (a) a protein transduction domain; and (b) a MYC polypeptide sequence. In some embodiments, the fusion peptide is a peptide of Formula (I):

protein transduction domain-MYC polypeptide
        sequence.

In some embodiments, a fusion peptide disclosed herein comprises (a) a protein transduction domain; (b) a MYC polypeptide sequence; and (c) one or more molecules that link the protein transduction domain and the MYC polypeptide sequence. In some embodiments, the fusion peptide is a peptide of Formula (II):

protein transduction domain-X-MYC polypeptide
        sequence, wherein -X- is molecule that links the protein transduction domain and the MYC polypeptide sequence. In some embodiments, -X- is at least one amino acid.

In some embodiments, a fusion peptide disclosed herein comprises (a) a protein transduction domain; (b) a MYC polypeptide sequence; (c) at least two protein tags; and (d) optionally linker(s). In some embodiments, the fusion peptide is a peptide of Formula (III-VI):

protein transduction domain-X-MYC polypeptide
        sequence-X-protein tag 1-X-protein tag 2    (Formula (III)), or protein transduction domain-MYC polypeptide
        sequence-X-protein tag 1-X-protein tag 2    (Formula (IV)), or protein transduction domain-MYC polypeptide
        sequence-protein tag 1-X-protein tag 2    (Formula (V)), or protein transduction domain-MYC polypeptide
        sequence-protein tag 1-protein tag 2    (Formula (VI)), wherein -X- is a linker. In some embodiments, -X- is one or more amino acids.

In some embodiments, a fusion peptide disclosed herein comprises (a) a protein transduction domain; (b) a MYC polypeptide sequence; (c) a 6-histidine tag; (d) a V5 epitope tag: and (e) optionally linker(s). In some embodiments, the fusion peptide is a peptide of Formula (VII-XIV):

protein transduction domain-X-MYC polypeptide
        sequence-X-6-histidine tag-X-V5
        epitope tag    (Formula (VII)), or protein transduction domain-MYC polypeptide
        sequence-X-6-histidine tag-X-V5
        epitope tag    (Formula (VIII)), or protein transduction domain-MYC polypeptide
        sequence-6-histidine tag-X-V5 epitope tag    (Formula (IX)), or protein transduction domain-MYC polypeptide
        sequence-6-histidine tag-V5 epitope tag    (Formula (X)), protein transduction domain-X-MYC polypeptide
        sequence-X-V5 epitope tag-X-6-
        histidine tag    (Formula (XI)), or protein transduction domain-MYC polypeptide
        sequence-X-V5 epitope tag-X-6-
        histidine tag    (Formula (XII)), or protein transduction domain-MYC polypeptide
        sequence-V5 epitope tag-X-6-
        histidine tag    (Formula (XIII)), or protein transduction domain-MYC polypeptide
        sequence-V5 epitope tag-6-histidine tag    (Formula (XIV)), wherein -X- is a linker. In some embodiments, -X- is one or more amino acids.

As noted above, in some embodiments, the MYC fusion protein comprises one or more linker sequences. The linker sequences can be employed to link the protein transduction domain, MYC polypeptide sequence, V5 epitope tag and/or 6-histidine tag of the fusion protein. In some embodiments, the linker comprises one or more amino acids. In some embodiments, the amino acid sequence of the linker comprises KGELNSKLE (SEQ ID NO: 11). In some embodiments, the linker comprises the amino acid sequence of RTG.

1. Protein Transduction Domain (PTD)

In some embodiments, the MYC fusion protein includes a protein transduction domain. Peptide transport provides an alternative for delivery of small molecules, proteins, or nucleic acids across the cell membrane to an intracellular compartment of a cell. One non-limiting example and well-characterized protein transduction domain (PTD) is a TAT-derived peptide. Frankel et al., (see, e.g., U.S. Pat. Nos. 5,804,604, 5,747,641, 5,674,980, 5,670,617, and U.S. Pat. No. 5,652,122) demonstrated transport of a cargo protein (β-galactosidase or horseradish peroxidase) into a cell by conjugating a peptide containing amino acids 48-57 of TAT to the cargo protein. In some embodiments, TAT protein transduction domain comprises an amino acid sequence of MRKKRRQRRR (SEQ ID NO: 7).

Another non-limiting example of a PTD is penetratin. Penetratin can transport hydrophilic macromolecules across the cell membrane (Derossi et al., *Trends Cell Biol.*, 8:84-87 (1998) incorporated herein by reference in its entirety). Penetratin is a 16 amino acid peptide that corresponds to amino acids 43-58 of the homeodomain of Antennapedia, a *Drosophila* transcription factor which is internalized by cells in culture.

Yet another non-limiting example of a PTD is VP22. VP22, a tegument protein from Herpes simplex virus type 1 (HSV-1), has the ability to transport proteins and nucleic acids across a cell membrane (Elliot et al., *Cell* 88:223-233, 1997, incorporated herein by reference in its entirety). Residues 267-300 of VP22 are necessary but may not be sufficient for transport. Because the region responsible for transport function has not been identified, the entire VP22 protein is commonly used to transport cargo proteins and nucleic acids across the cell membrane (Schwarze et al., *Trends Pharmacol Sci*, 21:45-48, 2000).

In some embodiments, the MYC fusion polypeptide includes a protein transduction domain. By way of example, but not by way of limitation, in some embodiments, the protein transduction domain comprises the protein transduction domain of one or more of TAT, penetratin, VP22, vpr, EPTD, R9, R15, VP16, and Antennapedia. In some embodiments, the protein transduction domain comprises the protein transduction domain of one or more of TAT, penetratin, VP22, vpr, and EPTD. In some embodiments, the protein transduction domain comprises the protein transduction domain of at least one of TAT, penetratin, VP22, vpr, EPTD, R9, R15, VP16, and Antennapedia. In some embodiments, the protein transduction domain comprises a synthetic protein transduction domain (e.g., polyarginine or PTD-5). In particular embodiments, the protein transduction domain comprises a TAT protein transduction domain. In some embodiments, the protein transduction domain is covalently linked to the MYC polypeptide. In some embodiments, the protein transduction domain is linked to the MYC polypeptide via a peptide bond. In some embodiments, the protein transduction domain is linked to the MYC polypeptide via a linker sequence. In some embodiments, the linker comprises a short amino acid sequence. By way of example, but not by way of limitation, in some embodiments, the linker sequences is 1, 2, 3, 4, 5, 6, 7, 8, 9, or 10 amino acids in length.

The MYC fusion protein of the present technology can be arranged in any desired order. For example, in some embodiments, the MYC fusion protein can be arranged in order of a) the protein transduction domain linked in frame to the MYC polypeptide, b) the MYC polypeptide linked in frame to the V5 domain, and c) the V5 domain linked in frame to the 6-histidine epitope tag. In some embodiments, the MYC fusion protein has an order of components of a) the MYC polypeptide linked in frame to the protein transduction domain, b) the protein transduction domain linked in frame to the V5 domain, and c) the V5 domain linked in frame to the 6-histidine epitope tag. In some embodiments, additional amino acid sequences can be included between each of the sequences. In some embodiments, additional amino acids can be included at the start and/or end of the polypeptide sequences.

In some embodiments, the protein transduction domain is a TAT protein transduction domain. In some embodiments, the protein transduction domain is $TAT_{[48-57]}$. In some embodiments, the protein transduction domain is $TAT_{[57-48]}$.

2. Protein Tag Domains

In some embodiments, the MYC fusion protein comprises a protein tag domain that comprises one or more amino acid sequences that facilitate purification of the fusion protein. In some embodiments, the protein tag domain comprises one or more of a polyhistidine tag, and an epitope tag. By way of example, but not by way of limitation, exemplary tags include one or more of a V5, a histidine-tag (e.g., a 6-histidine tag), HA (hemagglutinin) tags, FLAG tag, CBP (calmodulin binding peptide), CYD (covalent yet dissociable NorpD peptide), StrepII, or HPC (heavy chain of protein C). In some embodiments, the protein tag domain comprise about 10 to 20 amino acids in length. In some embodiments, the protein tag domain comprises 2 to 40 amino acids in length, for example 6-20 amino acids in length. In some embodiments, two of the above listed tags (for example, V5 and the his-tag) are used together to form the protein tag domain.

In some embodiments, the histidine tag is a 6-histidine tag. In some embodiments, the histidine tag comprises the sequence HHHHHH. In some embodiments, the fusion peptide disclosed herein comprises a V5 epitope tag. In some embodiments, the V5 tag comprises the amino acid sequence of: GKPIPNPLLGLDST. In some embodiments, the V5 tag comprises the amino acid sequence of IPNPLLGLD.

The protein tags may be added to the fusion protein disclosed herein by any suitable method. By way of example, but not by way of limitation, in some embodiments, a TAT-MYC polypeptide sequence is cloned into an expression vector encoding one or more protein tags, e.g., a polyHis-tag and/or a V5 tag. In some embodiments, a polyhistidine tag and/or a V5 tag is added by PCR (i.e., the PCR primers comprise a polyhistidine sequence and/or V5 sequence).

C. Construction of MYC Fusion Peptides

MYC fusion peptides (e.g., TAT-MYC fusion peptide) disclosed herein may be constructed by methods well known in the art. By way of example, but not by way of limitation, a nucleotide sequence encoding a TAT-MYC fusion peptide may be generated by PCR. In some embodiments, a forward primer for a human MYC sequence comprises an in frame N-terminal 9-amino-acid sequence of the TAT protein transduction domain (e.g., RKKRRQRRR). In some embodiments, a reverse primer for a human MYC sequence is designed to remove the stop codon. In some embodiments, the PCR product is cloned into any suitable expression vector. In some embodiments, the expression vector comprises a polyhistidine tag and a V5 tag.

In some embodiments, a fusion peptide disclosed herein comprises (a) TAT, and (b) c-MYC. In some embodiments, a fusion peptide disclosed herein comprises (a) $TAT_{[48-57]}$, and (b) c-MYC. In some embodiments, a fusion peptide disclosed herein comprises (a) $TAT_{[57-48]}$, and (b) c-MYC.

In some embodiments, a fusion peptide disclosed herein comprises (a) TAT, (b) c-MYC, (c) linker(s), (d) V5 tag, and (e) 6-histidine tag. In some embodiments, a fusion peptide disclosed herein comprises (a) $TAT_{[48-57]}$, (b) c-MYC, (c) linker(s), (d) V5 tag, and (e) 6-histidine tag. In some embodiments, a fusion peptide disclosed herein comprises (a) $TAT_{[57-48]}$, (b) c-MYC, (c) linker(s), (d) V5 tag, and (e) 6-histidine tag.

In some embodiments, the MYC portion of the MYC fusion peptide comprises any MYC polypeptide as described herein. In some embodiments, the MYC portion of the MYC fusion peptide comprises a MYC polypeptide sequence comprising the sequence shown below:

(SEQ ID NO: 4)
PLNVSETNRNYDLDYDSVQPYFYCDEEENFYQQQQQSELQPPAPSEDIWK

KFELLPTPPLSPSRRSGLCSPSYVAVTPFSLRGDNDGGGGSFSTADQLEM

VTELLGGDMVNQSFICDPDDETFIKNIIQDCMWSGESAAAKLVSEKLAS

YQAARKDSGSPNPARGHSVCSTSSLYLQDLSAAASECIDPSVVEPYPLND

SSSPKSCASQDSSAFSPSSDSLLSSTESSPQGSPEPLVLHEETPPTTSSD

SEEEQEDEEEIDVVSVEKRQAPGKRSESGSPSAGGHSKPPHSPLVLKRCH

-continued
VSTHQHNYAAPPSTRKDYPAAKRVKLDSVRVLRQISNNRKCTSPRSSDTE

ENVKRRTHNVLERQRRNELKRSFFALRDQIPELENNEKAPKVVILKKATA

YILSVQAEEQKLISEEDLLRKRREQLKHKLEQLR.

In some embodiments, the MYC fusion peptide comprises SEQ ID NO: 1. In some embodiments, the MYC-fusion peptide is SEQ ID NO: 1.

(SEQ ID NO: 1)
MRKKRRQRRRPLNVSFTNRNYDLDYDSVQPYFYCDEEENFYQQQQQSELQ

PPAPSEDIWKKFELLPTPPLSPSRRSGLCSPSYVAVTPFSLRGDNDGGGG

SFSTADQLEMVTELLGGDMVNQSFICDPDDETFIKNIIQDCMWSGFSAA

AKLVSEKLASYQAARKDSGSPNPARGHSVCSTSSLYLQDLSAAASECIDP

SVVFPYPLNDSSSPKSCASQDSSAFSPSSDSLLSSTESSPQGSPEPLVLH

EETPPTTSSDSEEEQEDEEEIDVVSVEKRQAPGKRSESGSPSAGGHSKPP

HSPLVLKRCHVSTHQHNYAAPPSTRKDYPAAKRVKLDSVRVLRQISNNRK

CTSPRSSDTEENVKRRTHNVLERQRRNELKRSFFALRDQIPELENNEKAP

KVVILKKATAYILSVQAEEQKLISEEDLLRKRREQLKHKLEQLRKGELNS

KLEGKPIPNPLLGLDSTRTGHHHHHH.

In some embodiments, the MYC portion of the MYC fusion peptide comprises a MYC polypeptide sequence comprising the sequence shown below:

(SEQ ID NO: 9)
PLNVSFTNRNYDLDYDSVQPYFYCDEEENFYQQQQQSELQPPAPSEDIWK

KFELLPTPPLSPSRRSGLCSPSYVAVTPFSLRGDNDGGGGSFSTADQLEM

VTELLGGDMVNQSFICDPDDETFIKNIIQDCMWSGFSAAAKLVSEKLAS

YQAARKDSGSPNPARGHSVCSTSSLYLQDLSAAASECIDPSVVFPYPLND

SSSPKSCASQDSSAFSPSSDSLLSSTESSPQASPEPLVLHEETPPTTSSD

SEEEQEDEEEIDVVSVEKRQAPGKRSESGSPSAGGHSKPPHSPLVLKRCH

VSTHQHNYAAPPSTRKDYPAAKRVKLDSVRVLRQISNNRKCTSPRSSDTE

ENVKRRTHNVLERQRRNELKRSFFALRDQIPELENNEKAPKVVILKKATA

YILSVQAEEQKLISEKDLLRKRREQLKHKLEQLR.

In some embodiments, the MYC fusion peptide comprises SEQ ID NO: 10; in some embodiments, the MYC-fusion peptide is SEQ ID NO: 10.

(SEQ ID NO: 10)
MRKKRRQRRRPLNVSFTNRNYDLDYDSVQPYFYCDEEENFYQQQQQSELQ

PPAPSEDIWKKFELLPTPPLSPSRRSGLCSPSYVAVTPFSLRGDNDGGGG

SFSTADQLEMVTELLGGDMVNQSFICDPDDETFIKNIIQDCMWSGFSAA

AKLVSEKLASYQAARKDSGSPNPARGHSVCSTSSLYLQDLSAAASECIDP

SVVFPYPLNDSSSPKSCASQDSSAFSPSSDSLLSSTESSPQASPEPLVLH

EETPPTTSSDSEEEQEDEEEIDVVSVEKRQAPGKRSESGSPSAGGHSKPP

HSPLVLKRCHVSTHQHNYAAPPSTRKDYPAAKRVKLDSVRVLRQISNNRK

CTSPRSSDTEENVKRRTHNVLERQRRNELKRSFFALRDQIPELENNEKAP

KVVILKKATAYILSVQAEEQKLISEKDLLRKRREQLKHKLEQLRKGELNS

KLEGKPIPNPLLGLDSTRTGHHHHHH.

The fusion protein may be modified during or after synthesis to include one or more functional groups. By way of example but not by way of limitation, the protein may be modified to include one or more of an acetyl, phosphate, acetate, amide, alkyl, and/or methyl group. This list is not intended to be exhaustive, and is exemplary only. In some embodiments, the protein includes at least one acetyl group.

III. Methods of Using Formulations of The Present Technology

Compositions of the present technology (e.g., compositions comprising a MYC-containing polypeptide formulated as biologically active, stable nanoparticles) provide MYC activity, and are thus useful in vivo (e.g., as an adjuvant, immune system enhancer, etc.) and in vitro (e.g., to stimulate growth and proliferation of stem cells, such as hematopoietic stem cells (HSCs), to condition HSCs for enhanced engraftment following hematopoietic stem cell transplantation, induce or enhance activation, growth, proliferation, viability, or survival of an immune cell and/or enhance antibody production by an immune cell in culture, etc.).

By way of example only and not by way of limitation, MYC-containing nanoparticulate compositions of the present technology can be used to prime donor HSCs (e.g., the patient's isolated HSCs or third party donor's HSC) for transplantation, e.g., to patients with immune-related diseases or disorders such as, but not limited to severe combined immunodeficiency.

Severe combined immunodeficiency (SCID) is a life-threatening primary immunodeficiency disease caused by defects compromising the quantity and function of T-cells and B-cells. Infants with SCID suffer from repeated life-threatening infections that usually lead to a diagnosis by the age of three to six months. Left untreated, children continue to experience severe, life-threatening infections and death by 2 years of age. Children with SCID are currently treated using HSCT designed to reconstitute a normal immune system. Outcomes of these transplants are best for the youngest infants, who are transplanted before they have suffered from a severe infection (most of these infants are either siblings of a proband or are identified by neonatal screening programs) and for patients with human leukocyte antigen (HLA)-matched family donors. In contrast, the results of transplants performed on older infants and those performed with cells from alternative donors are less favorable.

In some embodiments, T-cell and B-cell depleted donor hematopoietic cells, including hematopoietic stem and progenitor cells (HSPCs), are incubated ex vivo for one with the MYC-containing nanoparticulate compositions of the present technology ("primed"). Following incubation, the primed cells are washed and transplanted into the patient. Incubation of the donor cells with the compositions of the present technology increased proliferation of long-term self-renewing hematopoietic stem cells following transplantation.

In some embodiments, the donor hematopoietic cells are isolated from the patient. In some embodiments, the donor hematopoietic cells are incubated for 30 minutes, 60 minutes, 90 minutes or 120 minutes with the nanoparticulate MYC-containing compositions of the present technology. In some embodiments, the donor hematopoietic cells are incubated with 10 µg/ml, 20 µg/ml, 30 µg/ml, 40 µg/ml, 50

µg/ml, 60 µg/ml, 70 µg/ml, 80 µg/ml, 90 µg/ml, or 100 µg/ml of the nanoparticulate MYC-containing composition of the present technology. In some embodiments, cells are incubated with 50 µg/ml of a nanoparticulate MYC-containing compositions for 60 minutes. In some embodiments, the nanoparticles of the composition have an average particle size of between about 80 and 150 nm, between about 90 and 140 nm, between about 100 and 120 nm, or between about 100 and 110 nm, and comprise SEQ ID NO: 1. In some embodiments, the nanoparticles of the composition have an average particle size of between about 80 and 150 nm, between about 90 and 140 nm, between about 100 and 120 nm, or between about 100 and 110 nm, and comprise SEQ ID NO: 10.

For in vivo use, in some embodiments, pharmaceutical formulations including the nanoparticulate MYC-containing proteins described herein and optionally one or more additional therapeutic compounds and optionally, one or more pharmaceutically acceptable excipients, are administered to an individual in any manner, including one or more of multiple administration routes, such as, by way of non-limiting example, oral, parenteral (e.g., intravenous, intraperitoneal, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations. A summary of pharmaceutical formulations is found, for example, in *Remington: The Science and Practice of Pharmacy*, Nineteenth Ed (Easton, Pa.: Mack Publishing Company, 1995); Hoover, John E., *Remington is Pharmaceutical Sciences*, Mack Publishing Co., Easton, Pa. 1975; Liberman, H. A. and Lachman, L., Eds., Pharmaceutical Dosage Forms, Marcel Decker, New York, N.Y., 1980; and *Pharmaceutical Dosage Forms and Drug Delivery Systems*, Seventh Ed. (Lippincott Williams & Wilkins 1999).

In some embodiments, the nanoparticle formulations provided herein comprise a suitable buffer. Exemplary buffers include, but are not limited to Tris, sodium phosphate, potassium phosphate, histidine or citrate based buffers. In some embodiments, the formulations provided herein contain magnesium. In some embodiments, the formulations provided herein contain one or more surfactants. As used herein, the term "surfactant" can include a pharmaceutically acceptable excipient which is used to protect protein formulations against mechanical stresses like agitation and shearing. Examples of pharmaceutically acceptable surfactants include polyoxyethylensorbitan fatty acid esters (Tween), polyoxyethylene alkyl ethers (Brij), alkylphenyl-polyoxyethylene ethers (Triton-X), polyoxyethylene-polyoxypropylene copolymer (Poloxamer, Pluronic), and sodium dodecyl sulphate (SDS). Suitable surfactants include polyoxyethylenesorbitan-fatty acid esters such as polysorbate 20, (sold under the trademark Tween 20®) and polysorbate 80 (sold under the trademark Tween 80®). Suitable polyethylene-polypropylene copolymers are those sold under the names Pluronic® F68 or Poloxamer 188®. Suitable Polyoxyethylene alkyl ethers are those sold under the trademark Brij®. Suitable alkylphenolpolyoxyethylene esthers are sold under the tradename Triton-X. When polysorbate 20 (Tween 20®) and polysorbate 80 (Tween 80®) are used they are generally used in a concentration range of about 0.001 to about 1%, of about 0.005 to about 0.2% and of about 0.01% to about 0.1% w/v (weight/volume).

In some embodiments, the nanoparticle formulations provided herein comprise a stabilizer. As used herein, the term "stabilizer" can include a pharmaceutical acceptable excipient, which protects the active pharmaceutical ingredient and/or the formulation from chemical and/or physical degradation during manufacturing, storage and application. Chemical and physical degradation pathways of protein pharmaceuticals are reviewed by Cleland et al., Crit. Rev. Ther. Drug Carrier Syst., 70(4):307-77 (1993); Wang, *Int. J. Pharm.*, 7S5(2): 129-88 (1999); Wang, *Int. J. Pharm.*, 203(1-2): 1-60 (2000); and Chi et al, *Pharm. Res.*, 20(9): 1325-36 (2003). Stabilizers include but are not limited to sugars, amino acids, polyols, cyclodextrines, e.g., hydroxypropyl-beta-cyclodextrine, sulfobutylethyl-beta-cyclodextrin, beta-cyclodextrin, polyethylenglycols, e.g., PEG 3000, PEG 3350, PEG 4000, PEG 6000, albumin, human serum albumin (HSA), bovine serum albumin (BSA), salts, e.g., sodium chloride, magnesium chloride, calcium chloride, chelators, e.g., EDTA as hereafter defined. As mentioned hereinabove, stabilizers can be present in the formulation in an amount of about 10 to about 500 mM, an amount of about 10 to about 300 mM, or in an amount of about 100 mM to about 300 mM.

In some embodiments, the daily dosages for a composition including fusion peptide nanoparticles described herein are from about 0.001 to 1000.0 mg/kg per body weight, such as about 0.01 to 100.0 mg/kg per body weight, such as about 0.1 to 10.0 mg/kg per body weight. The foregoing range is merely suggestive, as the number of variables in regard to an individual treatment regime is large, and considerable excursions from these recommended values are not uncommon. In some embodiments, such dosages are optionally altered depending on a number of variables, not limited to the activity of the agent or composition described herein used, the disorder or condition to be treated, the mode of administration, the requirements of the individual subject, the severity of the disorder or condition being treated, and the judgment of the practitioner.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. An agent or compositions described herein exhibiting high therapeutic indices is preferred. The data obtained from cell culture assays and animal studies are optionally used in formulating a range of dosage for use in human. The dosage of such an agent or composition described herein lies preferably within a range of circulating concentrations that include the $ED_{50}$ with minimal toxicity. The dosage optionally varies within this range depending upon the dosage form employed and the route of administration utilized.

VII. Examples

The following examples are for illustrative purposes only and are non-limiting embodiments. Many modifications, equivalents, and variations of the present disclosure are possible in light of the above teaching, therefore, it is to be understood that within the scope of the appended claims, the disclosure may be practiced other than as specifically described.

EXAMPLE 1

Construction of a TAT-MYC Fusion Peptide of the Present Technology

Plasmid pTAT-MYC-V5-6xHis was made by PCR amplification of the coding regions for human MYC using a forward primer that contains an in-frame N-terminal 10-amino-acid sequence of the TAT protein transduction domain of HIV-1 (MRKKRRQRRR (SEQ ID NO: 7), and a reverse primer that removes the stop codon. The PCR product was cloned into pET101/D-Topo (Invitrogen) vector, which includes a C-terminal V5 epitope tag and 6-histidine protein tags.

A. Bacterial Strain used for Protein Expression

BL-21 RARE cells were created by transforming BL-21 Star™ E. coli strain (Invitrogen) with pRARE (CamR), isolated from BL21 Rosetta cells (Novagen), that express tRNAs for AGG, AGA, AUA, CUA, CCC, GGA codons.

B. Protein Induction and Purification

To prepare the fermenter inoculum, vials of the TAT-MYC Master Cell Bank (MCB) were thawed and used to inoculate shaker flasks containing LB media and supplemented with antibiotics (40 μg/mL kanamycin) for selection. Cells were expanded in an orbital shaker/incubator for fourteen to sixteen hours. The expanded culture was then used to inoculate the fermenter culture. The fermentations were induced at 37° C. by adding IPTG (~0.5-1 mM) to the culture when the cells were in logarithmic growth phase (OD of about 4.0). The cells were induced until the DO (dissolved oxygen) spike was observed, approx. 3-6 hours. After induction, the cell paste was harvested by centrifugation and stored at −70° C. or below until further processing. The bulk of the protein contained in the inclusion bodies is TAT-MYC.

The cell paste was resuspended in 8M Urea, 50 mM Phosphate pH 7.5. The suspension was mixed at room temperature until homogenous. The suspension was then passed through a homogenizer. The homogenized suspension was then adjusted to include 200 mM Sodium Sulfite and 10 mM Sodium Tetrathionate. The solution was mixed at room temperature until homogeneous. The sulfonylated lysate was mixed at 2-8° C. for ≥12 hours. The sulfonylated lysate was then centrifuged for an hour. The supernatant was collected and the pellet discarded. The supernatant was passed through a 0.22 μm membrane filter.

The sulfonylated TAT-MYC solution was purified by Ni affinity chromatography using Ni— resin. The column was equilibrated in 6M Urea, 50 mM Phosphate, 500 mM NaCl, and 10% Glycerol solution. The sulfonylated and clarified TAT-MYC was then loaded onto the column. The column was washed with 6M Urea, 50 mM Phosphate, 10% Glycerol, 500 mM NaCl, pH 7.5. The column was then washed with 6M Urea, 50 mM Phosphate, 10% Glycerol, and 2M NaCl, pH 7.5, followed another wash of 6M Urea, 50 mM Phosphate, 10% Glycerol, 50 mM NaCl, and 30 mM Imidazole, pH 7.5. The product was eluted from the column by running elution buffer containing 6M Urea, 50 mM Phosphate, 10% Glycerol, and 50 mM NaCl, pH 7.5 with a gradient from 100 to 300 mM Imidazole and collecting fractions. The protein containing fractions to be pooled was filtered through a 0.22 μm membrane and protein concentrations were measured using UV280.

The pooled fractions from the Ni-Sepharose chromatography step were further purified by anion exchange chromatography using Q-Sepharose resin. The pool was prepared for loading onto the column by diluting to the conductivity of the Q sepharose buffer (17.52 +/−1 mS/cm) with the second wash buffer (6M Urea, 50 mM Phosphate, 10% Glycerol, 2M NaCl, pH 7.5) from the Ni Sepharose chromatography step. The diluted pool was then loaded onto the column, followed by two chase steps using 6M Urea, 50 mM Phosphate, 300 mM NaCl, and 10% Glycerol, and further chase until the UV trace reached baseline.

EXAMPLE 2

Preparation of Nanoparticulate TAT-MYC Compositions

Refolding of the TAT-MYC proteins in the Q-Sepharose flow-through pool from Example 1 was accomplished using tangential flow filtration-based refolding method using a UFDF (ultrafiltration/diafiltration) membrane. The refolding process included a series of three refolding steps. The first refolding step involved the exchange of refold buffer 1 (3M Urea, 50 mM Phosphate, 500 mM NaCl, 10% Glycerol, 5 mM GSH, (Reduced Glutathione) 1 mM GSSG (Oxidized Glutathione)) over the course of about 120 minutes. The second refold step involved the exchange of refold buffer 2 (1.5M Urea, 50 mM Phosphate, 500 mM NaCl, 10% Glycerol, 5 mM GSH, (Reduced Glutathione) 1 mM GSSG (Oxidized Glutathione)) over the course of approximately 120 minutes, followed by ~120 minutes of recirculation. The third refold step consisted of the exchange of refold buffer 3 (50 mM Phosphate, 500 mM NaCl, 10% Glycerol, 5 mM GSH, (Reduced Glutathione) 1 mM GSSG (Oxidized Glutathione)) over the course of approximately 120 minutes, followed by 12 hours of recirculation. After the third refolding step was complete, the refold 3 solution was filtered through a 0.2 μm membrane and protein concentration was adjusted.

The protein concentration of the TAT-MYC fusion of SEQ ID NO: 1 was measured by Bradford protein assay (Sigma) compared to a standard curve of bovine serum albumin.

Several lots of refolded TAT-MYC were prepared according to the described method. For the purposes of these Examples, the lots presented are termed "F01," "C2A," C2B," "C6" "C7" "C12", "C13" and "C14." Each tested lot contained 50 mM Phosphate, 500 mM NaCl, 10% Glycerol, 5 mM GSH, (Reduced Glutathione) 1 mM GSSG (Oxidized Glutathione) as obtained following the third refold step with refold buffer 3, with the exception of C2A formulation, which additionally contained arginine.

Refolded TAT-MYC is sensitive to pH and was stable in a formulation of pH 7.5 +/−pH 0.3. Refolded TAT-MYC is also sensitive to NaCl concentrations and was stable at about 500 mM +/−50 mM NaCl. Refolded TAT-MYC was also stable up to a concentration of 1.2 mg/mL. Refolded TAT-MYC is stable at −80° C. for up to or about 2 years. Once thawed, it remains active when stored at 4° C. for up to or about a month.

EXAMPLE 3

Functional Analysis of Nanoparticulate TAT-MYC Compositions

TAT-MYC compositions were tested for activity as follows.

A spleen was harvested from a C57BL/6j (Jackson) mouse, and mechanically dissociated through wire mesh. The red blood cells were removed, CD4 positive T cells were isolated using commercially available isolation process (Dynabead), and the T cells were activated with 1 µg/ml anti-CD3 and anti-CD28 antibody. The cells were plated into a 48 well cluster dish at $1.5 \times 10^6$ cells per well in 1 ml of media. 24 hours later, the TAT-MYC formulation was added to the cells (a total of 12 µg per well) and incubated for 24 hours. 24 hours after adding the protein, the media was replaced and the cells were incubated for 48 hr. Cells were assessed for viability at 96 hours after the initial activation via flow cytometry (forward x side scatter). Results for C2A (prepared according to Example 2) are shown in FIG. 1.

Figure 1A:
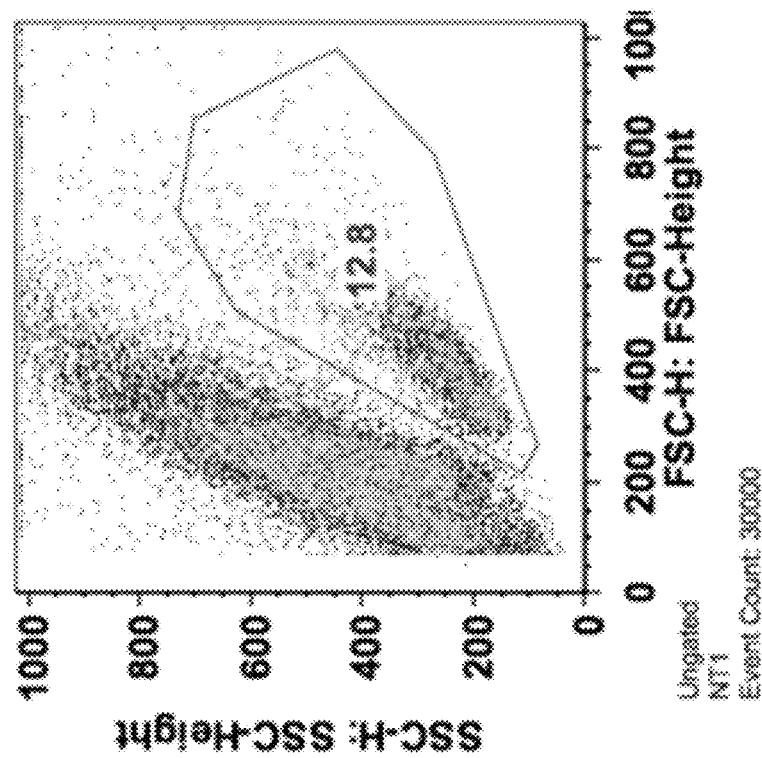

FIG. 1A (the plot on the left) shows the proliferation of untreated, activated T-cells (12.8). FIG. 1B (the plot on the right) shows the proliferation of activated T-cells treated with 6 µg of TAT-MYC formulation C2A for 24 hours. As shown, proliferation of T-cells more than doubles with C2A treatment.

For purposes of these examples, an active preparation, composition, formulation, or fraction of TAT-MYC is one that provides at least a 2-fold increase in T-cell proliferation as compared to control T-cells.

TABLE 1

| TAT-MYC Sample | Ratio of Treated:Nontreated |
|---|---|
| Positive Control | 2.0 |
| R147 | 1.1 |
| R149 | 1.5 |
| C12 | 2.0 |
| C13 | 2.7 |

EXAMPLE 4

Characterization of Nanoparticle Formulations

Compositions of nanoparticulate TAT-MYC protein, prepared as described in Example 2 and tested for biological activity as described in Example 3, were characterized using several diverse techniques to demonstrate that (a) TAT-MYC protein prepared by the methods of the present technology surprisingly and unexpectedly forms nanoparticles having a discreet size range; (b) only a sub-fraction of the nanoparticles within this range are biologically active, e.g., have MYC activity; and (c) activity is linked to both particle size and one or more post-translational modifications.

A. Stability of Functional Formulations

Two different preparations of TAT-MYC protein, termed F01 and F02, were evaluated by Asymmetrical Flow Field-flow Fractionation (AF4) and Multi-Angle Laser Light Scattering (MALLS) at two different temperatures to provide information on mass and size distribution of all components in the sample. F01 was refolded according to Example 2. F02 was prepared as discussed below. The AF4-MALLS analysis illustrated that F01 includes primarily a single population of particles having a discreet size range, and that particle size is stable over time and at varying temperature.

As noted above, F01 was prepared according to the methods of Example 2. F02 was prepared as described in Example 1B. After the refold, F02 was moved for the F01 formulation, 50 mM Phosphate, 500 mM NaCl, 10% Glycerol, 5 mM GSH, (Reduced Glutathione) 1 mM GSSG (Oxidized Glutathione), pH 7.5, to the final formulation of 50 mM Phosphate, 250 mM NaCl, 10% Glycerol, pH 7.0.

Figure 2A:
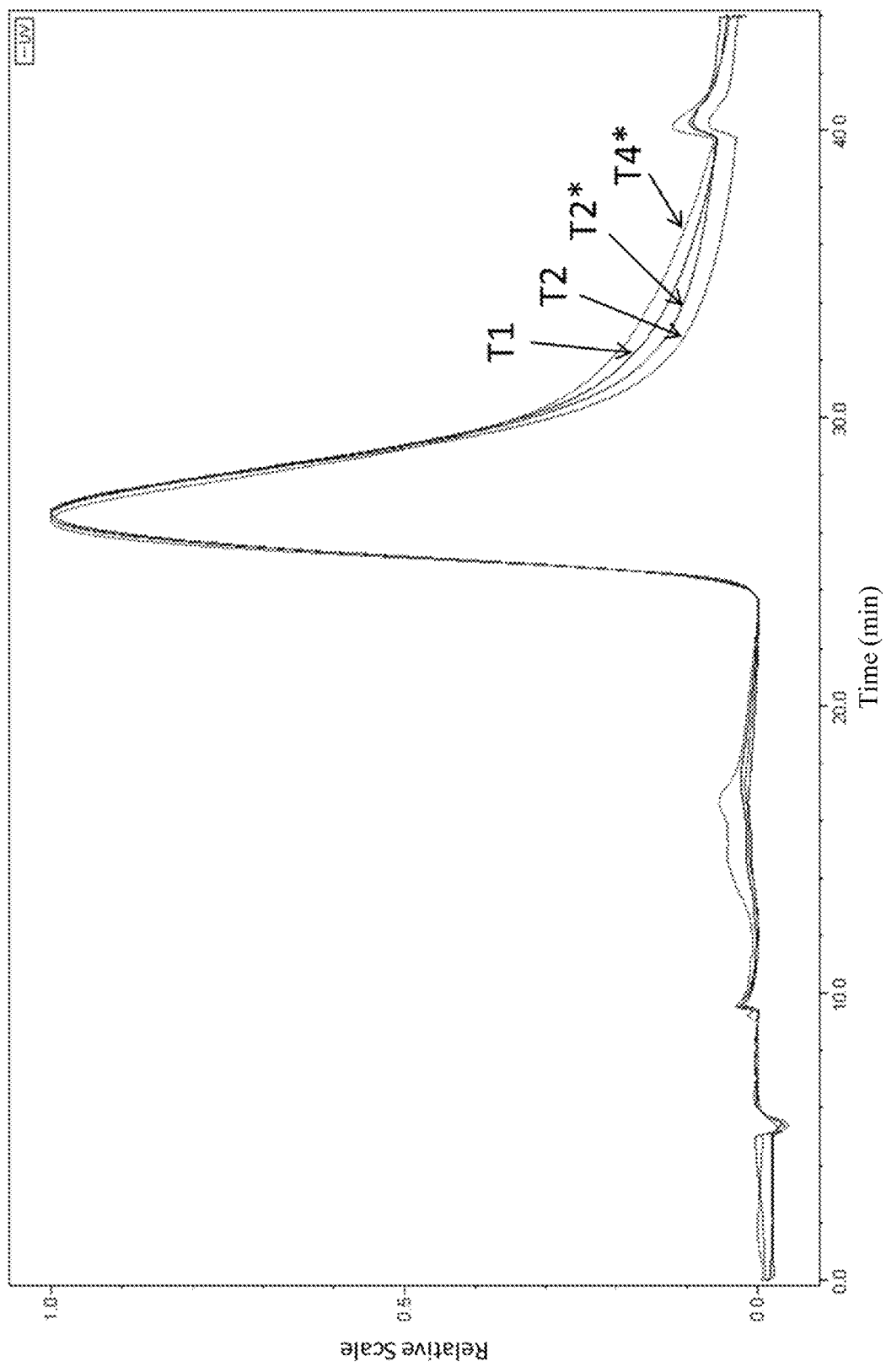
FIG. 2A and FIG. 2B show chromatograms of select MYC-containing nanoparticle formulations analyzed by Asymmetrical Flow Field-flow Fractionation (AF4) and Multiangle Laser Light Scattering (MALLS).

FIG. 2A shows the results for F01. Four different samples are shown in FIG. 2A: 2 F01 samples that were run at 25° C. and 2 F01 samples that were run at 5° C. are presented.

As shown in FIG. 2A, a single primary peak of nearly identical relative scale is seen at about 24 to about 32 minutes for all samples at both temperatures. This is indicative of a composition comprising a stable population of particles of discreet size.

Figure 2B:
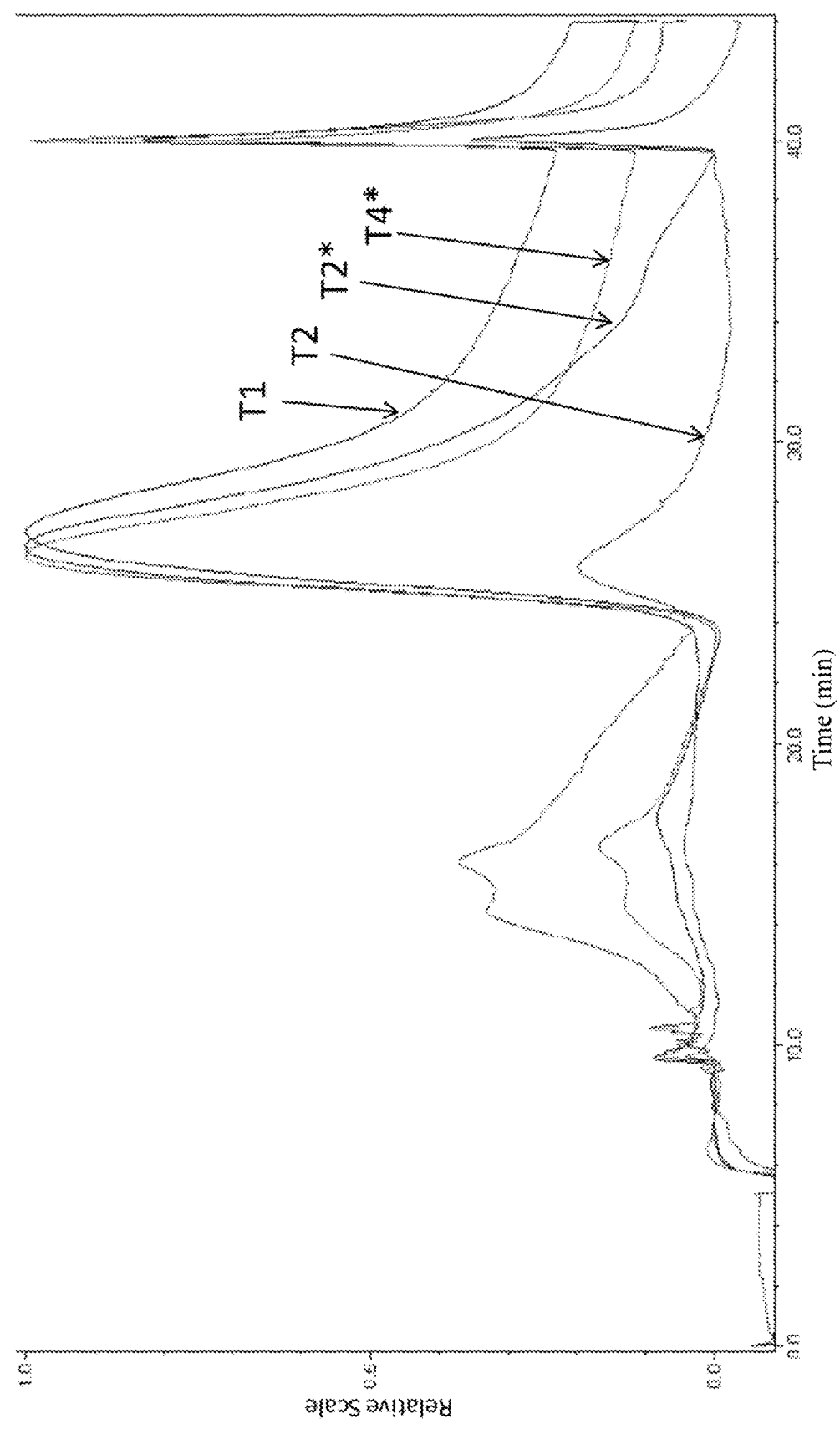

FIG. 2B provides results for F02. Again, four different samples are shown: 2 F02 samples run at 25° C. and 2 F02 samples run at 5° C. In contrast to the F01 results, several peaks were identified at various time points, all differing in relative scale. For peaks appearing between 10 and 20 minutes, the top trace and the third trace represent results from the samples run at 25° C.; the second and fourth trace represent the samples run at 5° C. For peaks appearing between 24 minutes and 32 minutes, the top three traces include both 5° C. samples and one of the 25° C. samples, while the lowest trace in this time frame represents the second sample run at 25° C. The peaks at the 40-minute time point show one of the 5° C. samples as the lowest trace, with the remaining three sample traces above.

While F01 showed function in the T-cell assay as described in Example 3, F02 did not.

Accordingly, formulations of the present technology comprise stable, TAT-MYC particles of discreet size, and have biological function.

B. Biological Activity of the Formulations of the Present Technology is Linked to Particle Size 1. Size Exclusion Chromatography and High Performance Liquid Chromatography Verify Discreet Particle Sizes are Present in Biologically Active TAT-MYC Preparation To verify that the function of TAT-MYC protein is linked to nanoparticles of discreet size, three different preparations of TAT-MYC were evaluated. Two functional preparations (termed "C12" and "C13"), and one non-functional preparation ("R147"), were characterized via size exclusion chromatography followed by high performance liquid chromatography as follows.

Functional C12 and C13 were made according to the procedures outline in Example 2. R147 was generated during a run where the TFF refold steps were accelerated to investigate the necessity to have the refold steps take 120 min, 120 min and 14 hours as detailed under Example 1B. Instead, the entire refold was achieved in 60 min.

SEC-HPLC procedure to analyze TAT-MYC was carried out on an Agilent 1100 Series. 3 columns were configured in tandem. Setup was as follows: Guard column-2000 A-500 A-300 A. The mobile phase was 50 mM Sodium Phosphate, 500 mM NaCl pH 7.0 with a Flow rate of 1.0 ml/min, length of each run was 40 min, and the protein was introduced onto the column in a 100 µL injection volume.

Figure 3:
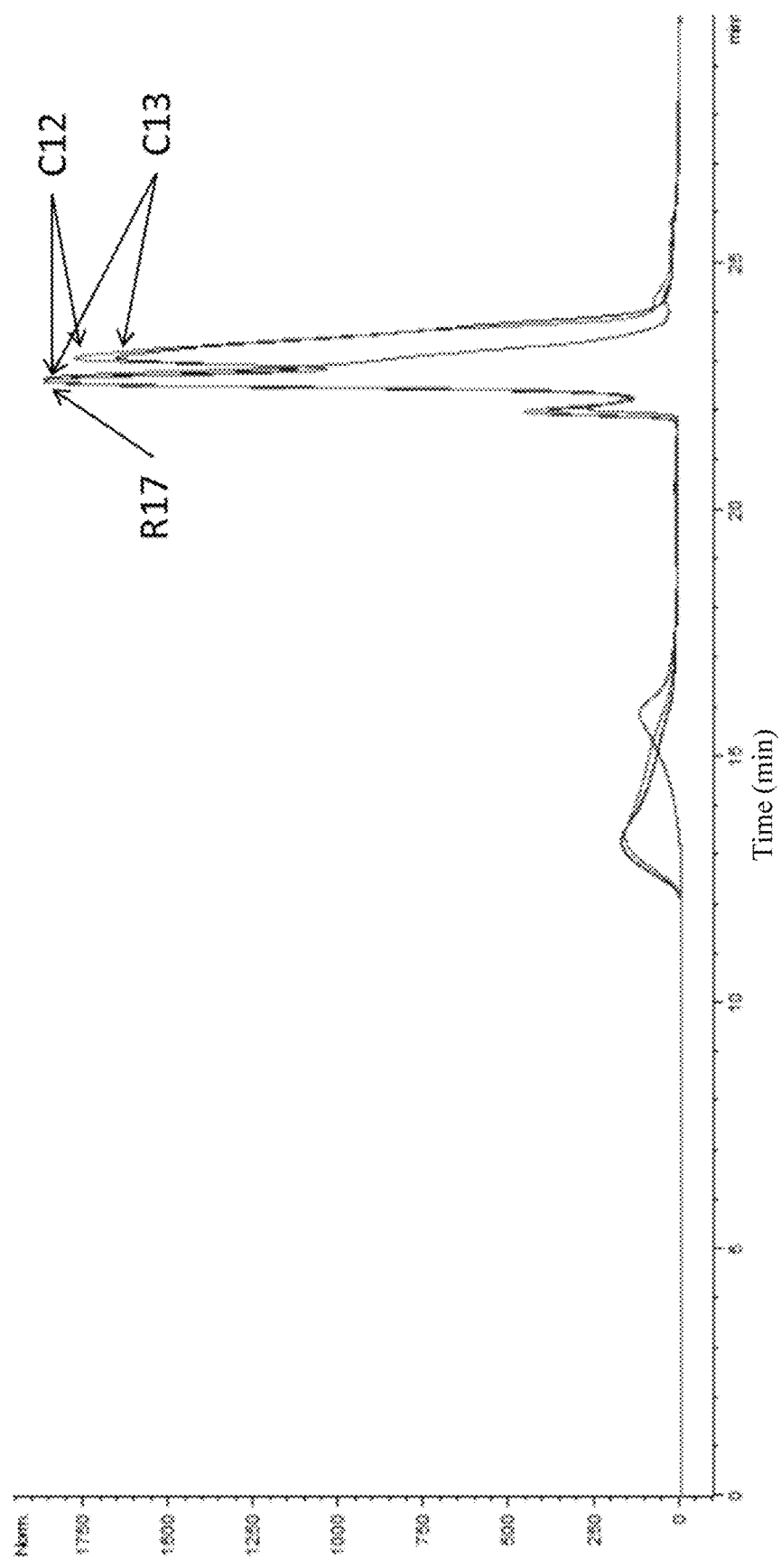
FIG. 3 shows a comparison of chromatograms derived by fractionating biologically active and inactive MYC-containing nanoparticle formulations by size exclusion chromatography (SEC) using Sepax SRT-C 2000 and 300 columns in tandem. Traces showing fractionation of biologically active nanoparticle formulations C12 and C13 and the biologically inactive formulation R147 are indicated.

The traces of the three samples are shown in FIG. 3. SEC-HPLC allows for high resolution of particle size distribution and shows two distinct peaks at about 13 and 16 minutes. While the peak at 13 minutes had active particles, the peak at 24 minutes includes active particles. Note that the peaks observed at 22-24 min are a result of excipients in the refold buffer.

2. Size Exclusion Chromatography and Multi-Angle Static Light Scattering Analysis to Determine Particle Size SEC-multi-angle static light scattering (MALS) was also used to analyze the same three samples, to confirm particle size (molecular weight) to control for and eliminate any unexpected molecular interactions with columns.

Figure 4A:
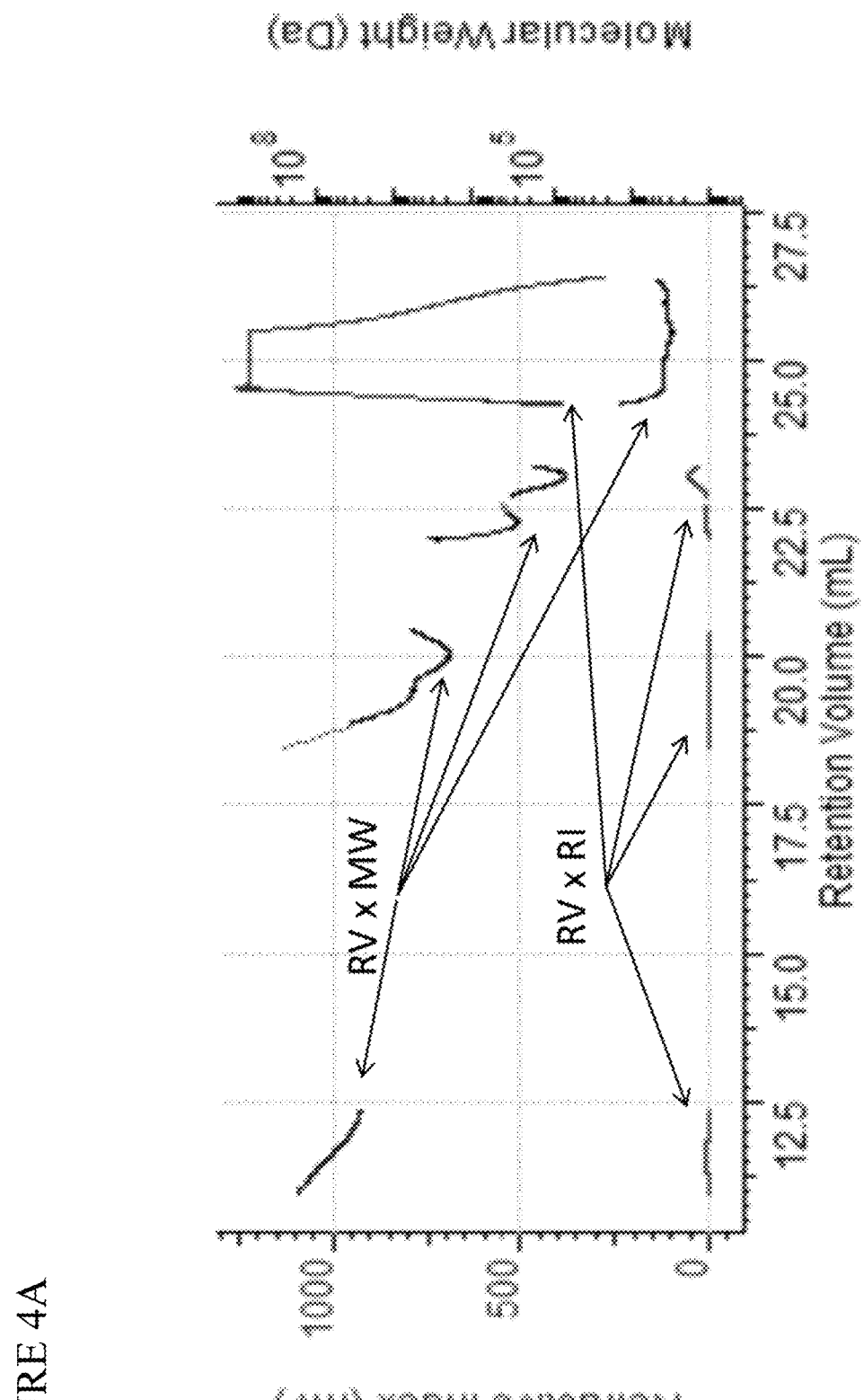
FIG. 4A and FIG. 4B show analysis of MYC-containing nanoparticle formulation C2A using Size Exclusion Chromatography with Multi-Angle Light Scattering analysis (SEC-MALS).
Figure 4B:
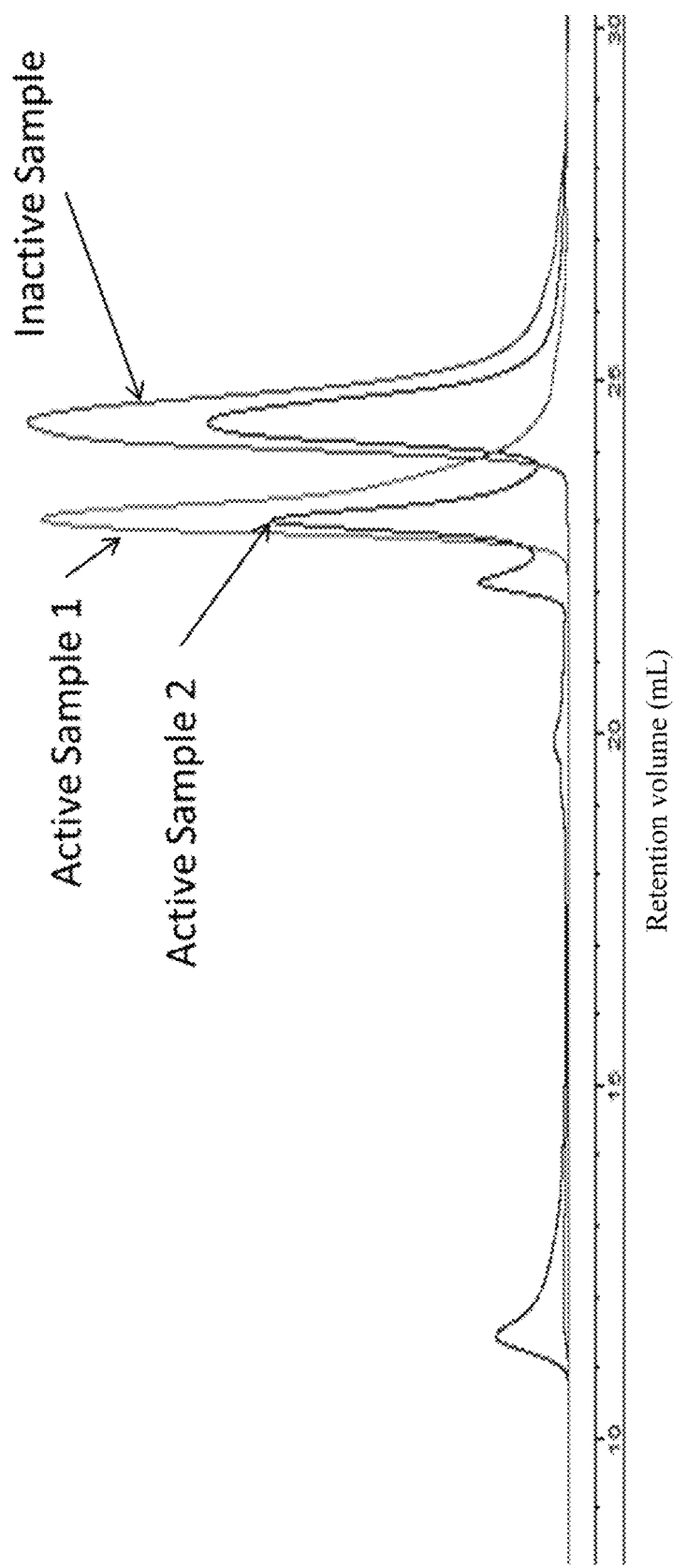

Results are shown in FIGS. 4A and 4B. FIG. 4A is a graph showing refractive index (hatched lines) and molecular weight (solid lines) of sample C2A formulated in 50 mM Phosphate, 500 mM NaCl, 10% Glycerol, 5 mM GSH, (Reduced Glutathione) 1 mM GSSG (Oxidized Glutathione), 250 mM Arg, pH 7.5. FIG. 4B is the SEC trace of C2A showing relative signal of C2A refold buffer with glutathione, but no Arg (Active Sample 1), and refold buffer with Arg, but no glutathione (Active Sample 2).

Results shown in FIG. 4A and 4B confirm that the majority of active particles have a molecular mass of about $10^7$-$10^9$ daltons (see fraction at retention volume of about 12.5 mL).

3. Dynamic Light Scattering Analysis to Verify Particle Size

Biologically active formulation C2A and three additional preparations, C12, C13 (both active), and R149 (inactive) assayed to determine particle size. Functional C12 and C13 were made according to the procedures outline in Example 2. R149 was generated during a run similar to C12 and C13, but the TFF refold steps were replaced by dialysis that was conducted over a period of 6 hours. Functional C2A was made according to the procedures outline in 0080-0082, but the final formulation buffer included 250 mM Arg.

The sample were evaluated using Dynamic Light Scattering (DLS), a technique that can be used to determine the size distribution profile of small particles in suspension or polymers in solution. DLS measures the diffusion of particles moving under Brownian motion and converts the diffusion coefficient to hydrodynamic diameter using the Stokes-Einstein relationship:

$$D_h = \frac{k_B T}{3\pi \eta D}$$

where $D_h$=hydrodynamic diameter, $k_B$=Boltzmann's constant, $\eta$=dynamic viscosity, D=translational diffusion coefficient, and T=thermodynamic temperature.

Samples and standards were analyzed on a Malvern Zetasizer Nano (s). Test samples and controls were diluted in formulation buffer to a concentration of 0.5 mg/mL prior to analysis. Samples were analyzed and sizing evaluated by intensity, number counts, and volume distribution. The reported value for the analysis was obtained from the intensity Z-Ave (d.nm) value.

Figure 5A:
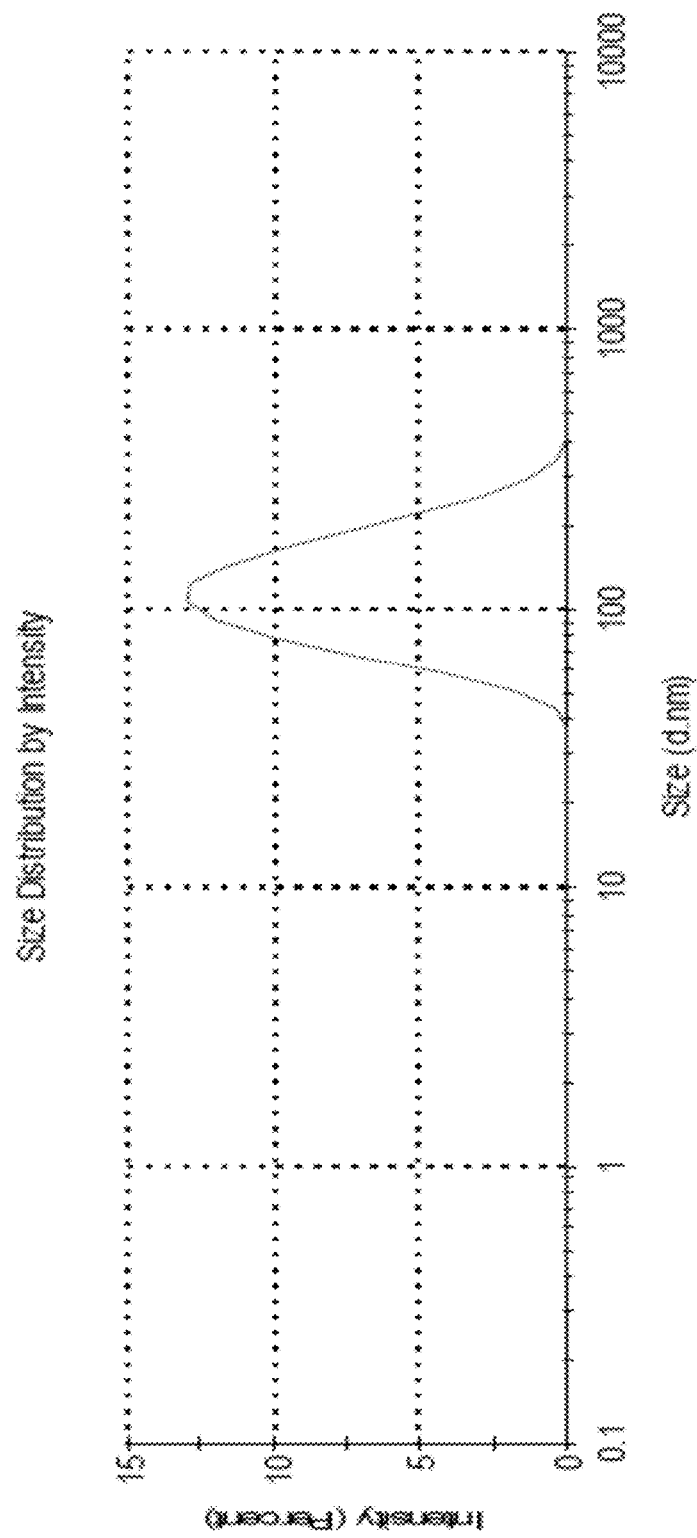
FIG. 5A-D depicts size distribution of MYC-containing nanoparticles in select formulations analyzed by Dynamic Light Scattering (DLS) technique.

Results are shown in FIGS. 5A-5D. FIG. 5A shows the DLS trace for C2A; the average particle size (diameter) was 106.2 nm.

Figure 5B:
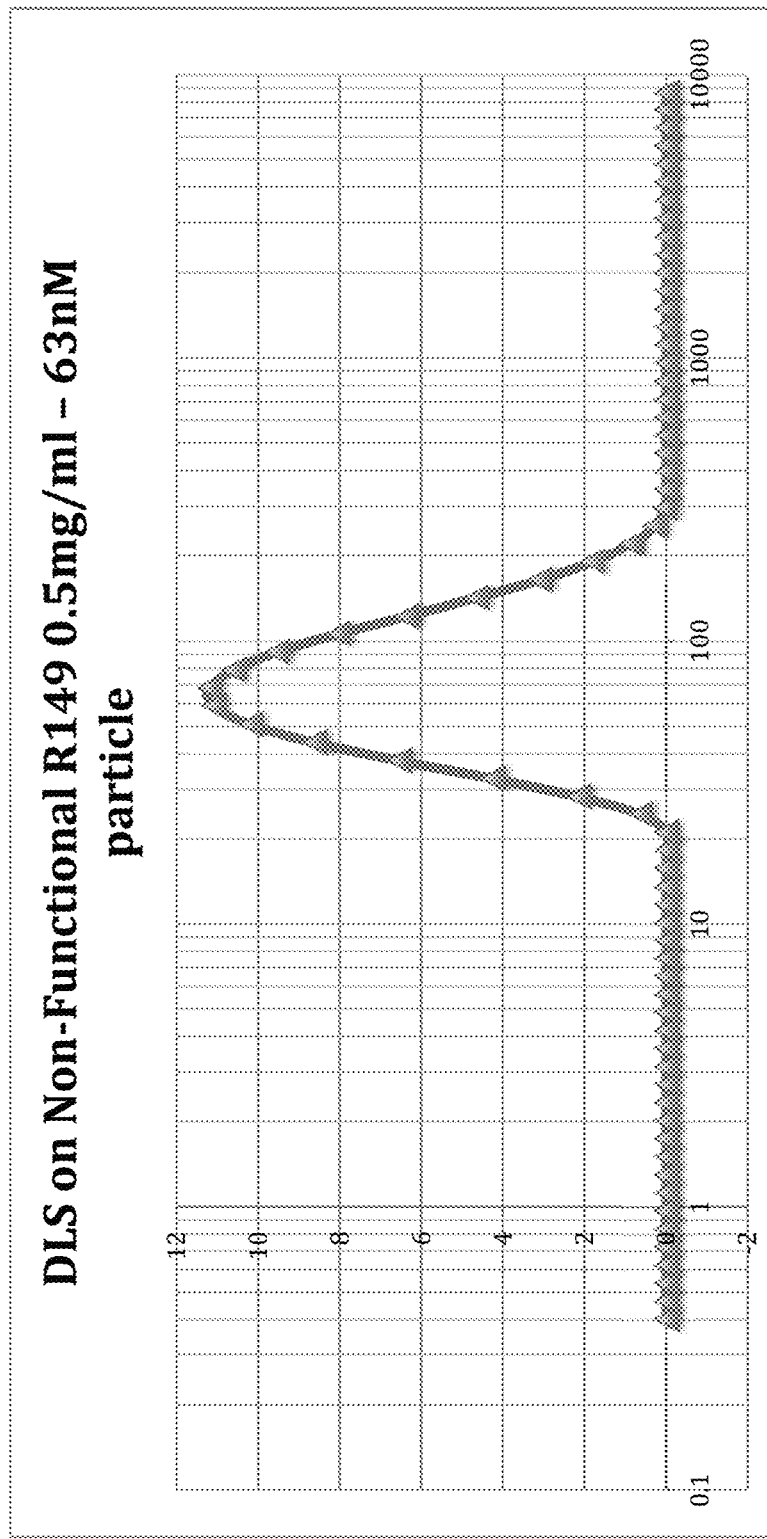
Figure 5C:
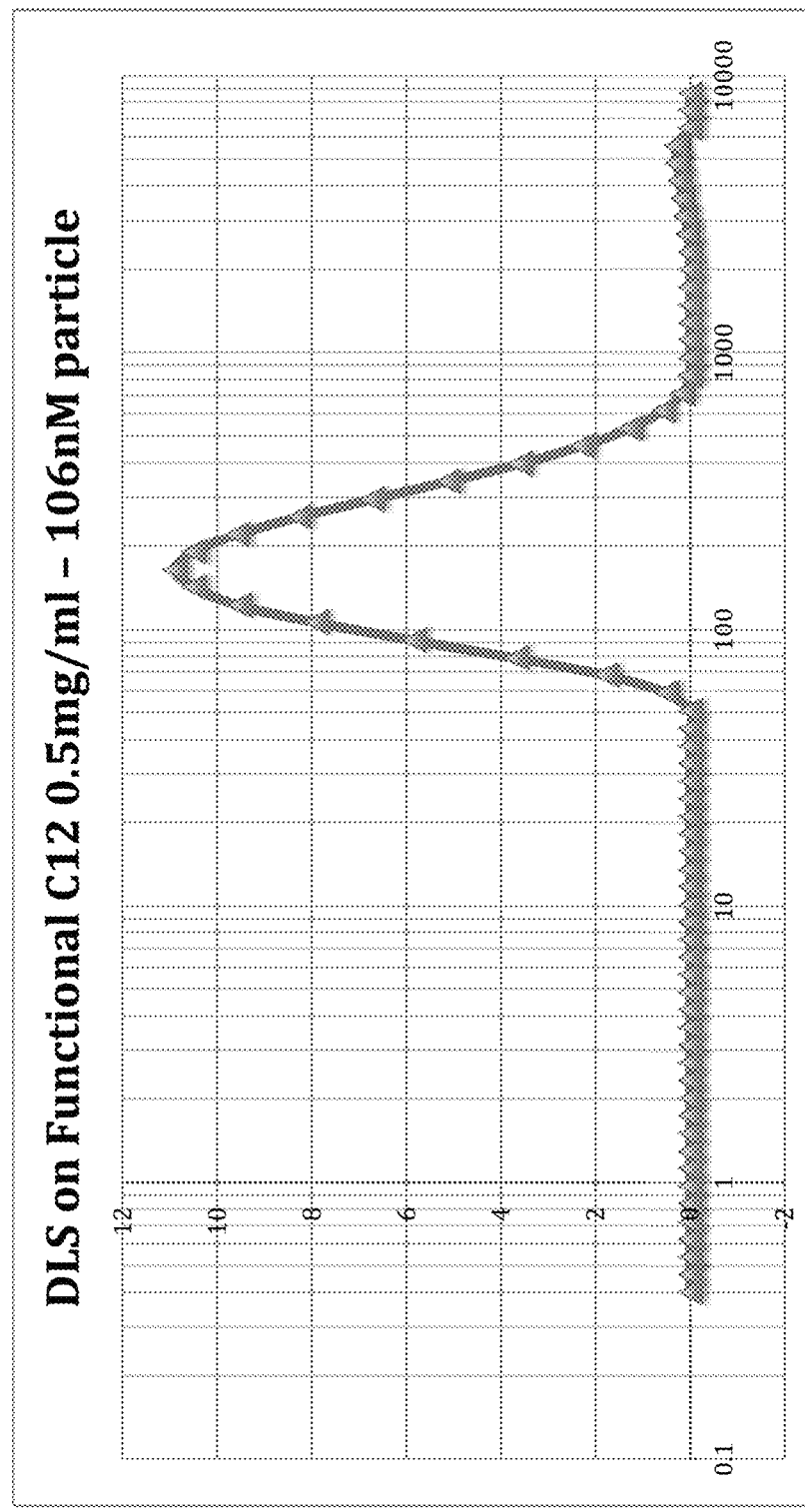
Figure 5D:
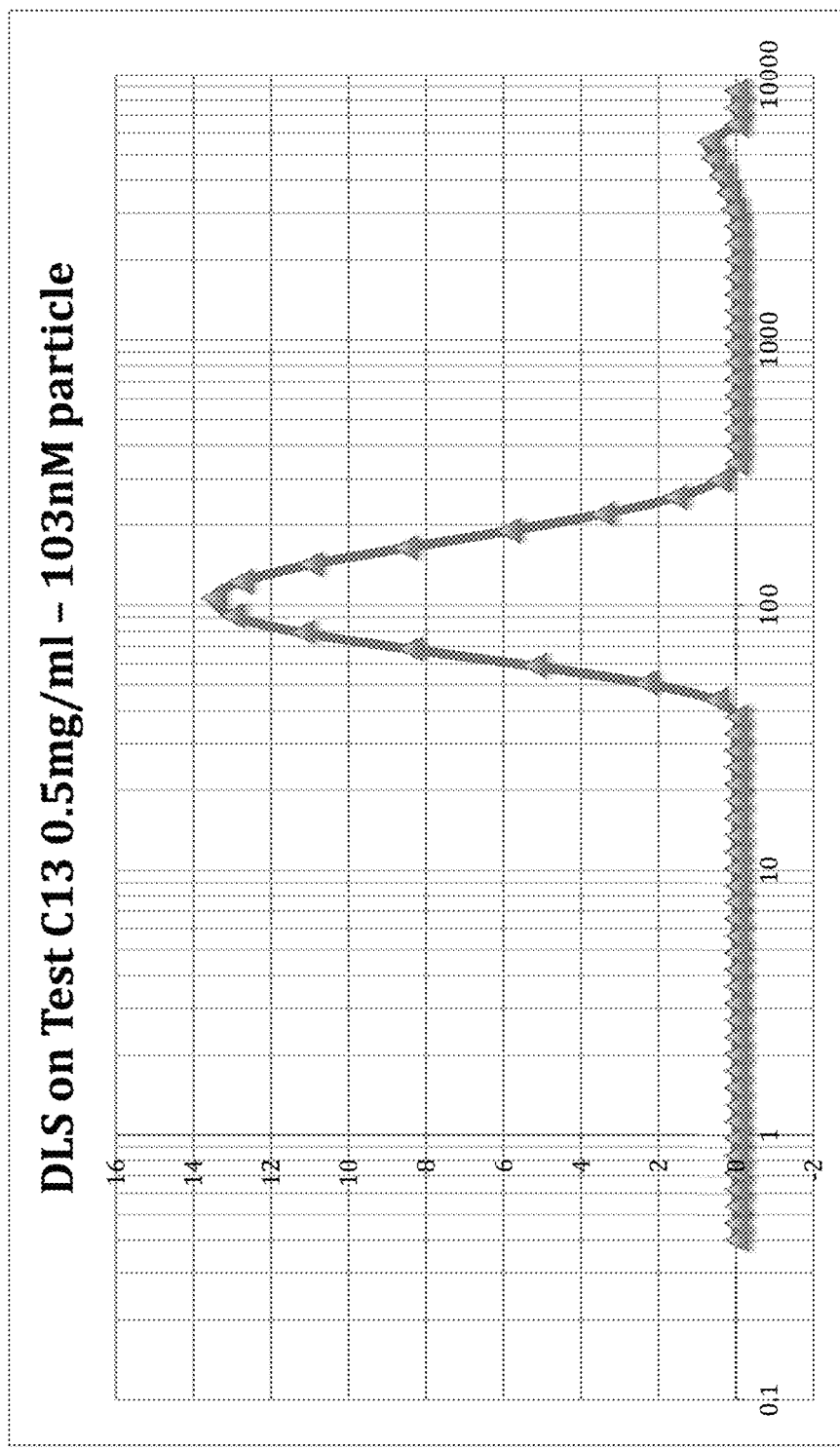

FIGS. 5B-5D show DLS trace data for preparations R149 (inactive), C12 (active) and C13 (active) respectively. The inactive preparation has an average particle size of 63 nm, while preparations C12 and C13 have average particle sizes of 106 and 103 nm, respectively.

4. Nanoparticle Tracking Analysis to Verify Size Distribution of Biologically Active TAT-MYC Particles in Solution Nanoparticle Tracking Analysis (NTA) is a method for visualizing and analyzing particles in liquids that relates the rate of Brownian motion to particle size. The rate of movement is related only to the viscosity and temperature of the liquid; it is not influenced by particle density or refractive index. NTA allows the determination of a size distribution profile of small particles with a diameter of approximately 10-1000 nanometers (nm) in liquid suspension.

Nanoparticle size and concentrations were measured by nanoparticle tracking analysis (NTA) with a NS300 instrument (Malvern, Worchester, UK) equipped with a 488-nm laser and NTA 2.3 software. Before data acquisition, the sample was diluted 1:200-1:400 in a final volume of 400 μL and was loaded into the flow cell. Video was captured at room temperature for 60 s. The lower size detection limit was automatically set by the software.

Figure 6A:
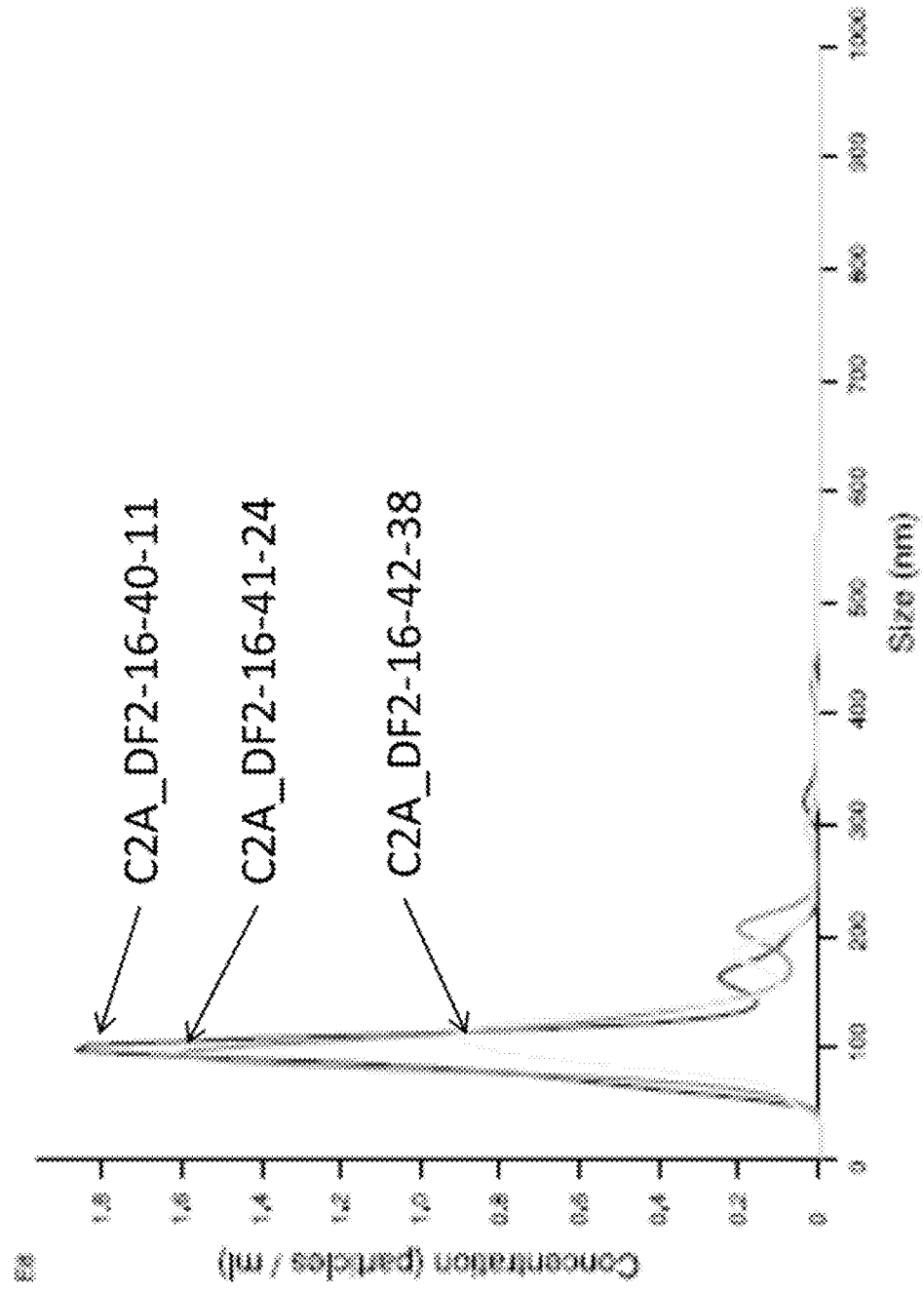
FIG. 6A and FIG. 6B shows analysis of MYC-containing nanoparticle formulation C2A using Nanoparticle Tracking Analysis (NTA) technique.
Figure 6B:
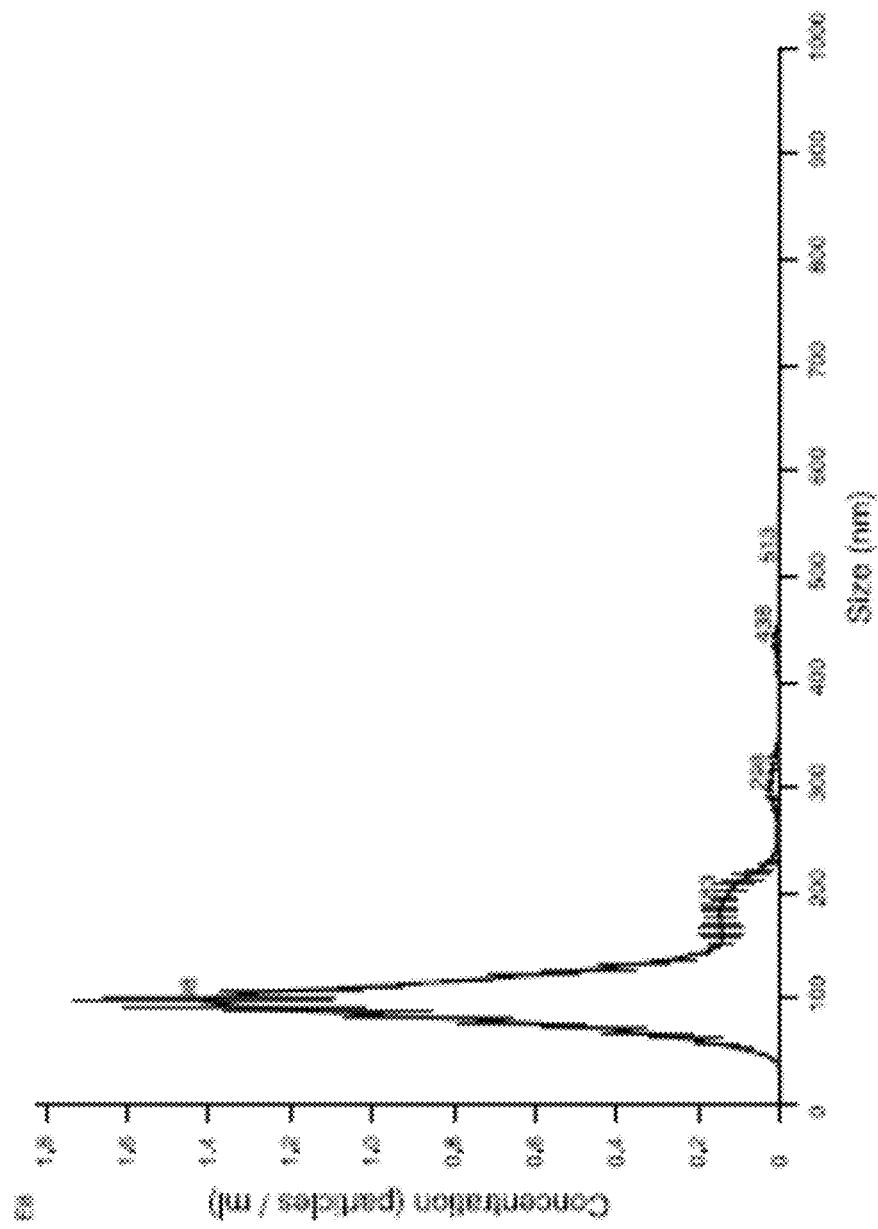

Results are shown in FIGS. 6A and 6B. NTA analysis was performed in triplicate with the active C2A preparation. FIG. 6A indicates that the majority of particles in the sample are about 100 nm in size. FIG. 6B shows the averaged concentration and size. A statistical breakdown of particle size in the sample is provided in the table below.

| Merged Data | Particle Size | Mean +/− standard error | Particle Size |
|---|---|---|---|
| Mean | 116.0 nm | Mean | 116.9 +/− 4.7 nm |
| Mode | 98.5 nm | Mode | 101.5 +/− 4.9 nm |
| SD | 48.7 nm | SD | 48.5 +/− 3.5 nm |
| D10 | 71.7 nm | D10 | 72.4 +/− 2.7 nm |
| D50 | 98.6 nm | D50 | 100.1 +/− 4.1 nm |
| D90 | 171.2 nm | D90 | 174.4 +/− 9.0 nm |

5. Electron Microscopy to Visually Verify Uniformity and Size of Biologically Active Nanoparticulate TAT-MYC The above biochemical results were further confirmed by electron microscopy. A TAT-MYC formulation prepared as described in Example 2 and termed "C2B" was tested in the T-cell assay of Example 3 to verify biological activity. C2B was visualized via electron microscopy as follows.

Fifty-microliter drops of TAT-MYC nanoparticle formulation were spotted onto parafilm and then absorbed to glow-discharged, carbon- and formvar-coated copper transmission electron microscopy (TEM) grids (G400 copper; EM Science). Grids were blotted dry on Kimwipe (Kimberly-Clark), followed by staining with uranyl acetate (2% [wt/vol]) and TEM (Philips CM10) at 80 kV. The particles were observed at ×4,800 magnification.

Figure 7:
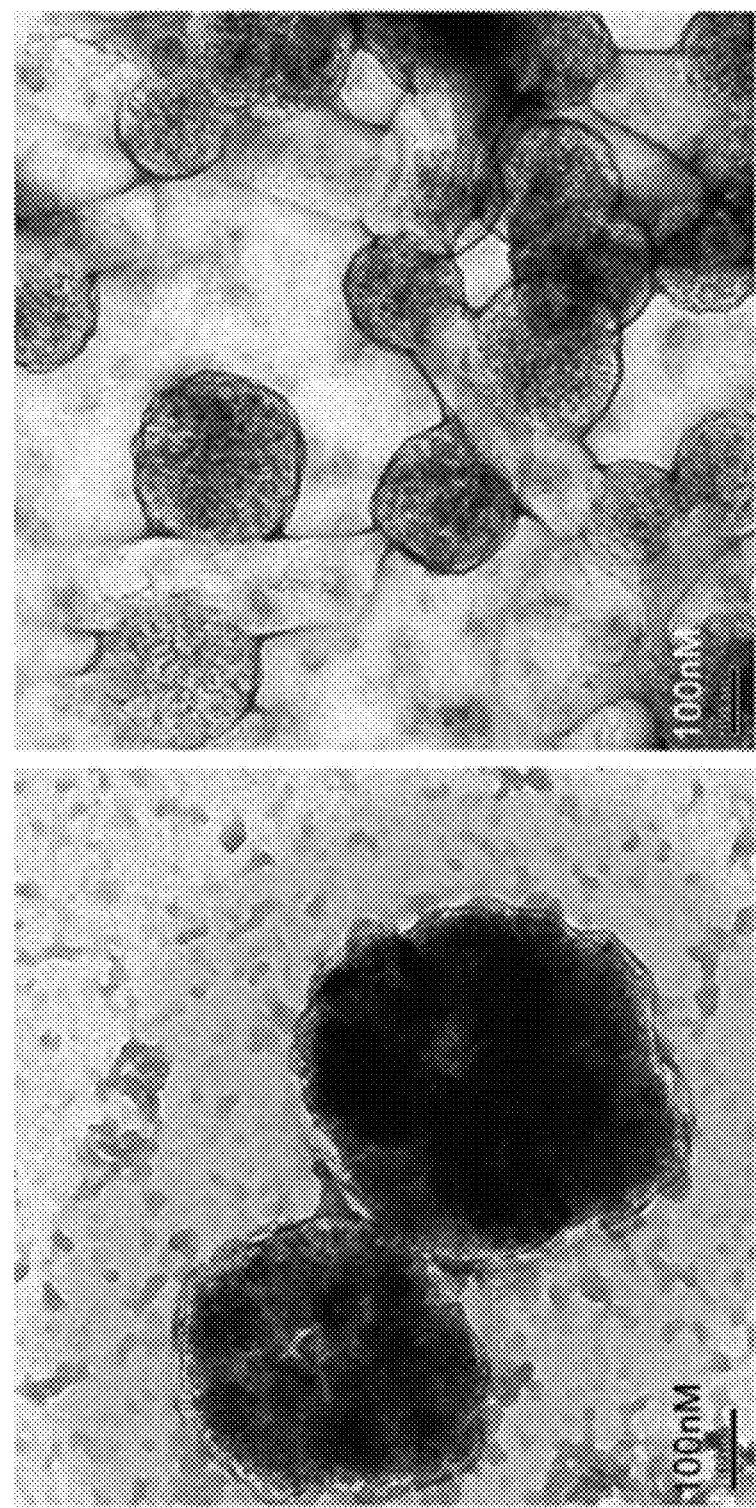
FIG. 7 shows analysis of MYC-containing nanoparticle formulation C2B using electron microscopy technique.

Results are shown in FIG. 7. FIG. 7 shows discreet particles in the 100 nm size range (dark balls). The particles are uniform in shape, and while some variation in size was noted in the micrograph, the data in sections B-E confirm that the size range of active particles is in agreement with those shown in the micrograph.

C. Biological Function of the TAT-MYC Formulations of the Present Technology

To further distinguish active versus inactive TAT-MYC preparations, peptide mapping was performed. Peptide mapping, also known as peptide fingerprinting, is a technique of forming two-dimensional patterns of peptides (on paper or gel) by partial hydrolysis of a protein followed by electrophoresis and chromatography. The peptide pattern (or fingerprint) produced is characteristic for a particular protein and the technique can be used to separate a mixture of peptides.

Six different TAT-MYC formulations were digested with endoprotease AspN. Three of the samples C2B, C6, and C7, were prepared according to Example 2 and showed biological activity in the T-cell assay of Example 3. Three of the samples, C4, 147, and 149, were prepared as follows. R149 was generated during a run similar to C12 and C13, but the TFF refold steps were replaced by dialysis that was conducted over a period of 6 hours. R147 was generated during a run were the TFF refold steps were accelerated to investigate the necessity to have the refold steps take 120 min, 120 min and 14 hours as detailed under Example 2. Instead, the entire refold was achieved in 60 min. C4 was made according to the procedures outlined in Example 1B, but rather then adjusting the salt and conductivity of the Q load for a flow through, this Q column was run as a bind and then eluted over a salt gradient. None of these samples showed biological activity in the Example 3 T-cell assay.

Protein digests were performed as follows. TAT-MYC was denatured by guanidine hydrochloride, reduced by TCEP (Tris 2-carboxyethyl phosphine), alkylated by iodoacetamide, and digested by endoproteinase Asp-N, which cleaves at the N-terminal of the aspartic acid residues. The resulting peptides were separated by reversed phase HPLC and monitored with 215 nm absorbance. Peptide identity in the peak elution profile was established by mass spectrometry. For routine protein analysis, identity may be established by visual comparison of the peak profiles in the UV-chromatogram of the sample to a reference sample.

Figure 8:
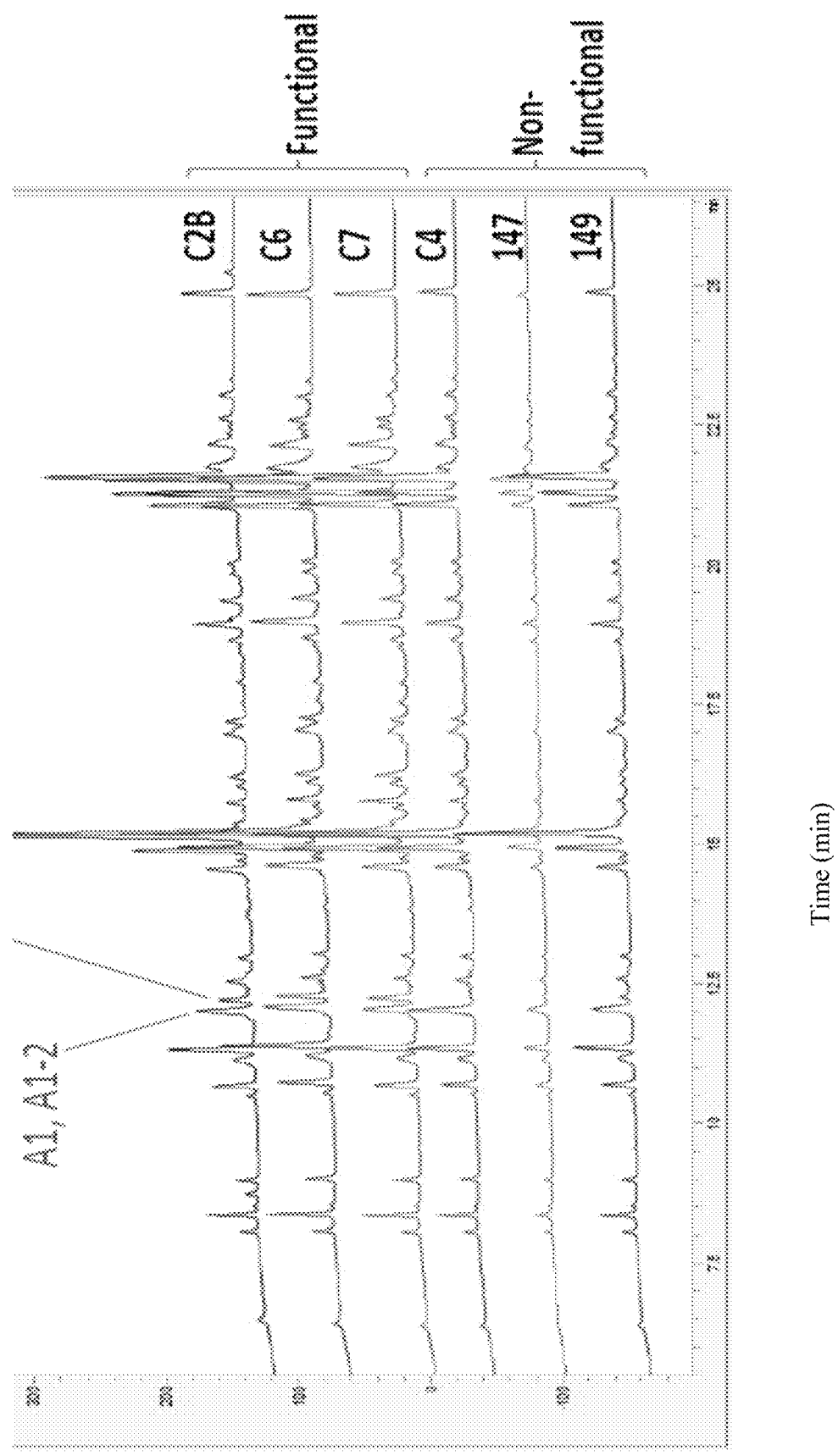
FIG. 8 shows a comparison of Asp-N endoproteinase digests of biologically active and inactive MYC-containing nanoparticle formulations by peptide mapping analysis technique. Biologically active MYC-containing nanoparticle formulations C2B, C6 and C7 ("functional") were compared to biologically inactive MYC-containing nanoparticle formulations C4, 147 and 149 ("non-functional").
Figure 12:
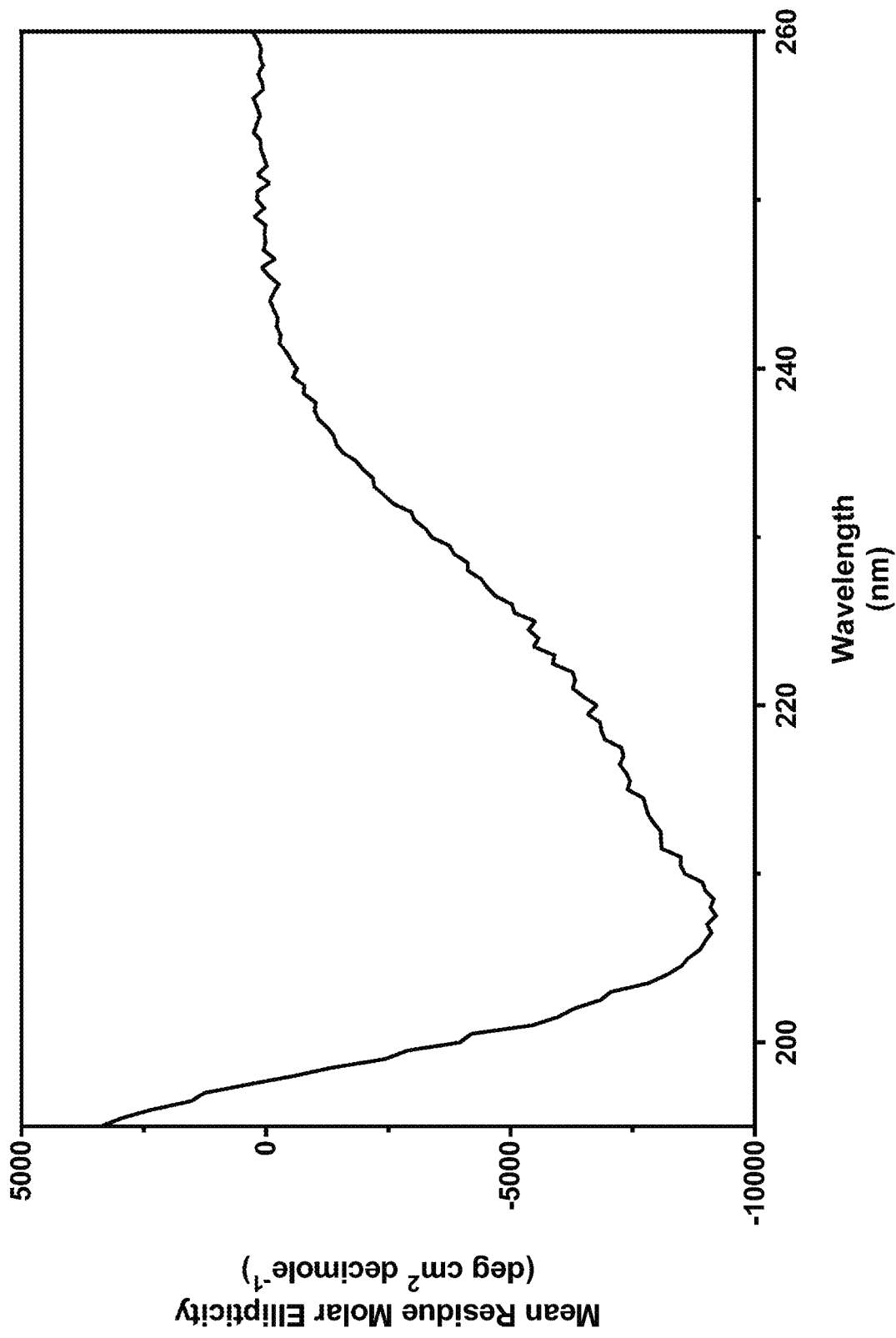
FIG. 12 shows the results for Near UV CD Spectroscopy analysis of nanoparticle formulation C13 depicted as mean residues molar ellipticity (deg cm$^2$ per decimole) as a function of wavelength (nm).
Figure 13:
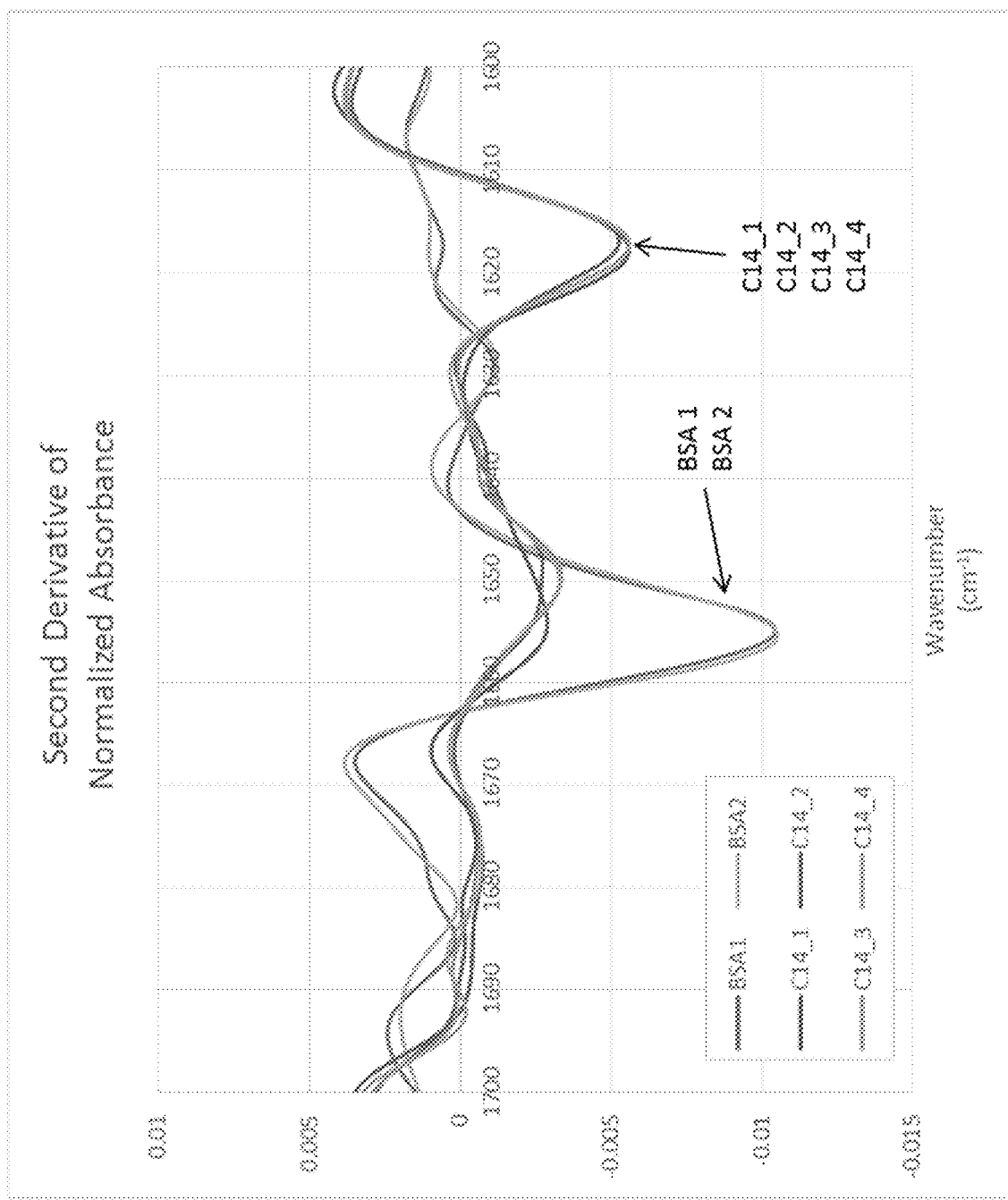
FIG. 13 shows the Normalized Second Derivative Fourier transform infrared spectra (FTIR) for four separate samples of nanoparticle formulation C14 in comparison with two control samples of bovine serum albumin (BSA).

Protein fragments were analyzed by HPLC. Results are shown in FIG. 8. The top three traces of FIG. 8 represent the biologically active samples. The bottom three traces represent the inactive samples. As shown in FIG. 12, a peak between the 12 and 12.5 minute time points, immediately to the right of the peak labeled A1, A1-2, was present in all three active samples, but was absent or minimally visible in the inactive samples. Without wishing to be bound by theory, it is likely that one or more aspartic acid residues is acetylated in the active sample.

EXAMPLE 5

Structural Characterization of MYC-Containing Nanoparticle Formulations

The primary, secondary, tertiary and quaternary structures of MYC-containing nanoparticle formulations were evaluated using an array of biochemical, biophysical and functional characterization techniques as outlined in the table below using standard techniques.

Summary of MYC-Containing Nanoparticle Structure and Function Elucidation Strategy

| Structure | Quality Attribute | Assay |
|---|---|---|
| Primary Structure | Post translational modifications | Peptide Mapping RP-HPLC |
| Secondary/Tertiary Structure | Folding Patterns | Far-UV CD Spectroscopy Near-UV CD Spectroscopy FTIR Spectroscopy |
| Quaternary Structure | High Molecular Weight Species | Analytical Ultracentrifugation DLS dSEC-HPLC |
| | Higher Order Structure | Electron Microscopy |

Nanoparticle formulation C13 was used for the majority of characterization analyses presented in this example. In some cases, data from an alternate nanoparticle formulation (either C2B or C14) is presented herein. Nanoparticle formulation C14 was also produced at a similar manufacturing scale according to essentially the same process as was utilized for nanoparticle formulation C13.

A. Peptide Mapping by Liquid Chromatography-Mass Spectrometry (LC/MS)

The myc-containing nanoparticle formulations were analyzed as described in the chart above with the addition of mass spectrometry with Electrospray Ionization (ESI) with a Time of Flight (TOF) analyzer. Because there was no UV detection during the MS run, a visual alignment of the MS Total Ion Chromatogram (TIC) and the UV chromatogram was performed to assign the observed mass to the respective UV peaks.

Figure 9:
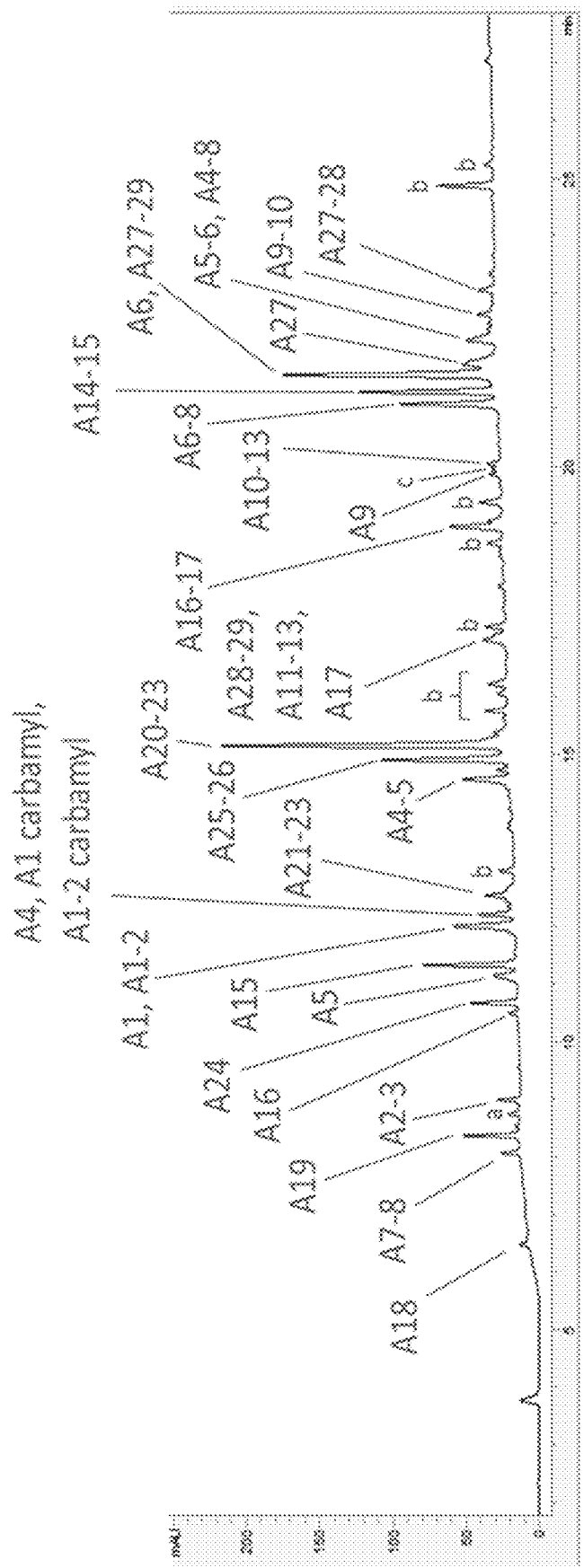
FIG. 9 shows a representative peptide map for MYC-containing nanoparticle formulation C13 with the individual peptide peaks identified.

The mass spectrometry analysis confirmed 100% coverage of peptides based on the expected peptide sequence. FIG. 9 shows a representative peptide map for MYC peptides with peptide peaks identified. The assignment of peptides for each peak is provided in the table below.

Theoretical TAT-MYC Asp-N Peptides

| Peptide # | Amino Acid Position | Sequence |
|---|---|---|
| 1 | 1 - 21 | (—)MRKKRRQRRRPLNVSFTNRNY(D) (SEQ ID NO: 12) |
| 2 | 22 - 23 | (Y)DL(D) (SEQ ID NO: 13) |
| 3 | 24 - 25 | (L)DY(D) (SEQ ID NO: 14) |
| 4 | 26 - 34 | (Y)DSVQPYFYC(D) (SEQ ID NO: 15) |
| 5 | 35 - 56 | (C)DEEENFYQQQQQSELQPPAPSE(D) (SEQ ID NO: 16) |
| 6 | 57 - 93 | (E)DIWKKFELLPTPPLSPSRRSGLCSPSYVAVTPFSLRG(D) (SEQ ID NO: 17) |
| 7 | 94 - 95 | (G)DN(D) (SEQ ID NO: 18) |
| 8 | 96 - 105 | (N)DGGGGSFSTA(D) (SEQ ID NO: 19) |
| 9 | 106 - 117 | (A)DQLEMVTELLGG(D) (SEQ ID NO: 20) |
| 10 | 118 - 126 | (G)DMVNQSFIC(D) (SEQ ID NO: 21) |
| 11 | 127 - 128 | (C)DP(D) (SEQ ID NO: 22) |
| 12 | 129 - 129 | (P)D(D) (SEQ ID NO: 23) |
| 13 | 130 - 140 | (D)DETFIKNIIIQ(D) (SEQ ID NO: 24) |
| 14 | 141 - 166 | (Q)DCMWSGFSAAAKLVSEKLASYQAARK(D) (SEQ ID NO: 25) |
| 15 | 167 - 188 | (K)DSGSPNPARGHSVCSTSSLYLQ(D) (SEQ ID NO: 26) |

| Theoretical TAT-MYC Asp-N Peptides | | |
|---|---|---|
| Peptide # | Amino Acid Position | Sequence |
| 16 | 189 - 198 | (Q)DLSAAASECI(D) (SEQ ID NO: 27) |
| 17 | 199 - 209 | (I)DPSVVFPYPLN(D) (SEQ ID NO: 28) |
| 18 | 210 - 220 | (N)DSSSPKSCASQ(D) (SEQ ID NO: 29) |
| 19 | 221 - 229 | (Q)DSSAFSPSS(D) (SEQ ID NO: 30) |
| 20 | 230 - 259 | (S)DSLLSSTESSPQGSPEPLVLHEETPPTTSS(D) (SEQ ID NO: 31) |
| 21 | 260 - 266 | (S)DSEEEQE(D) (SEQ ID NO: 32) |
| 22 | 267 - 271 | (E)DEEEI(D) (SEQ ID NO: 33) |
| 23 | 272 - 326 | (I)DVVSVEKRQAPGKRSESGSPSAGGHSKPPHSPLVLKRCHVSTHQHNYAAPPSTRK(D) (SEQ ID NO: 34) |
| 24 | 327 - 336 | (K)DYPAAKRVKL(D) (SEQ ID NO: 35) |
| 25 | 337 - 357 | (L)DSVRVLRQISNNRKCTSPRSS(D) (SEQ ID NO: 36) |
| 26 | 358 - 387 | (S)DTEENVKRRTHNVLERQRRNELKRSFFALR(D) (SEQ ID NO: 37) |
| 27 | 388 - 426 | (R)DQIPELENNEKAPKVVILKKATAYILSVQAEEQKLISEE(D) (SEQ ID NO: 38) |
| 28 | 427 - 464 | (E)DLLRKRREQLKHKLEQLRKGELNSKLEGKPIPNPLLGL(D) (SEQ ID NO: 39) |
| 29 | 465 - 476 | (L)DSTRTGHHHHHH(-) (SEQ ID NO: 40) |

B. Reversed Phase High Performance Liquid Chromatography (RP-HPLC)

A reversed phase HPLC (RP-HPLC) method was employed for the quantitation of post translational modifications and product related impurities. The test sample was diluted in denaturing buffer (7.5 M Guanidine HCl, 0.0625M TrisHCl pH 7.3) and separated using an Agilent AdvanceBio RP-mAb C4 column (2.1×150 mm, Solid core beads 3.5 μm, 450 Å). The column was equilibrated at a temperature of 50° C. Elution was achieved by applying a flow rate of 0.5 mL/min and a linear gradient of 0.1% TFA (w/v) in 100% $H_2O$ (Eluent A) and 0.1% (w/v) TFA in 100% ACN (Eluent B) as shown in the table below. Detection was performed at 280 nm.

RP-HPLC Gradient Profile

| Time (min) | % Eluent B |
|---|---|
| 0.00 | 23.0 |
| 15.00 | 37.0 |
| 35.00 | 45.0 |
| 36.00 | 70.0 |
| 37.00 | 70.0 |
| 38.00 | 23.0 |
| 45.00 | 23.0 |

Figure 10B:
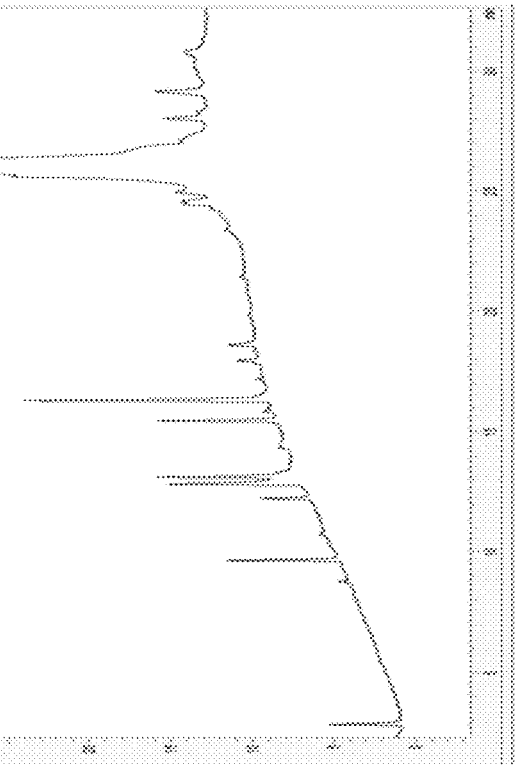
FIG. 10A-C shows RP-HPLC Chromatograms for nanoparticle formulation C13.
Figure 10A:
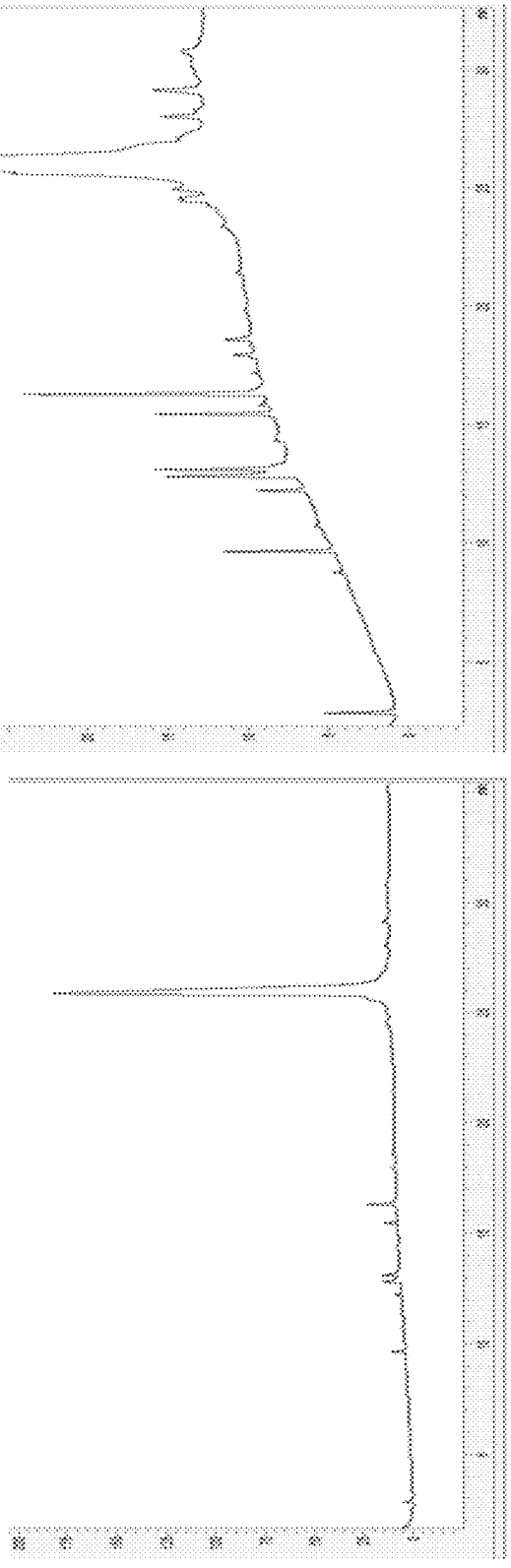
Figure 10C:
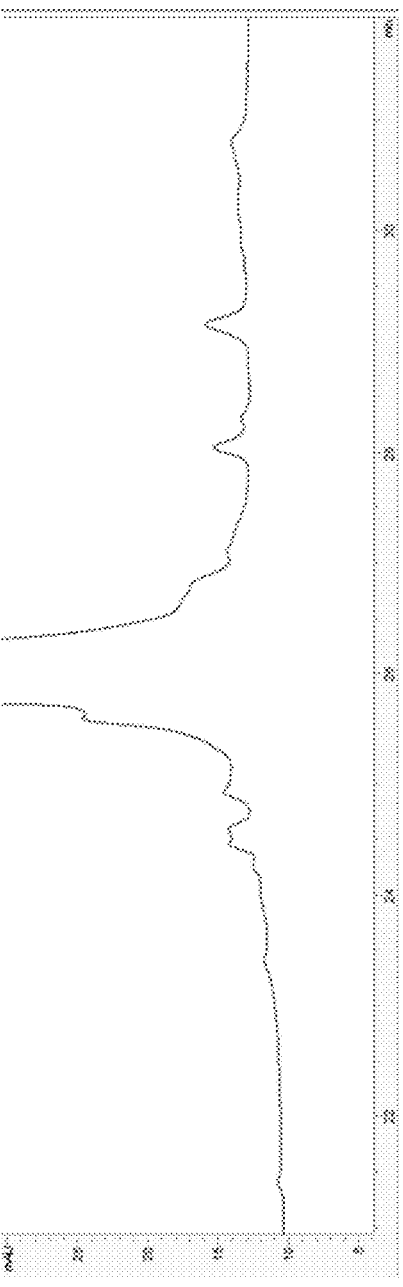

Analysis of nanoparticle formulation C13 indicated the presence of the main peak and a few minor peaks, as illustrated in FIG. 10. The identification of impurity peaks was not performed in this particular example.

C. Circular Dichroism Spectroscopy

The structure of nanoparticle formulation C13 was evaluated using Circular Dichroism spectroscopy (CD) in both the "far-UV" spectral region (190-250 nm) and the "near-UV" spectral region (250-350 nm). In the far UV region, the chromophore is the peptide bond and the signal arises when it is located in a regular, folded environment. The near UV region can be sensitive to certain aspects of tertiary structure. At these wavelengths, the chromophores are the aromatic amino acids and disulfide bonds, and the CD signals they produce are sensitive to the overall tertiary structure of the protein.

Nanoparticle formulation C13 was diluted to an absorbance of 0.75 AU at 280 nm for near UV, and 1.1 AU at 195 nm for far UV. Glutathione has a significant impact of sample absorbance in the UV. Thus, to increase the signal contribution from the protein, samples were buffer exchanged into reduced glutathione and glutathione free buffers. Testing parameters for the samples are shown in table below.

Testing Parameters for Characterization of Nanoparticle Formulations by CD Spectroscopy

| Parameter | Value |
|---|---|
| Temperature | Ambient |
| Concentration | Various concentration tested |
| Wavelength Range | 340-240 nm for NUV |
| | 250-195 nm for FUV |
| Bandwidth | 1 nm |
| Step size | 0.5 nm |
| Collection Interval | 1 second |
| Readings[1] | 3 for NUV |
| | 5 for FUV |

[1]All readings were averaged to produce the reported spectrum for each sample

Figure 11:
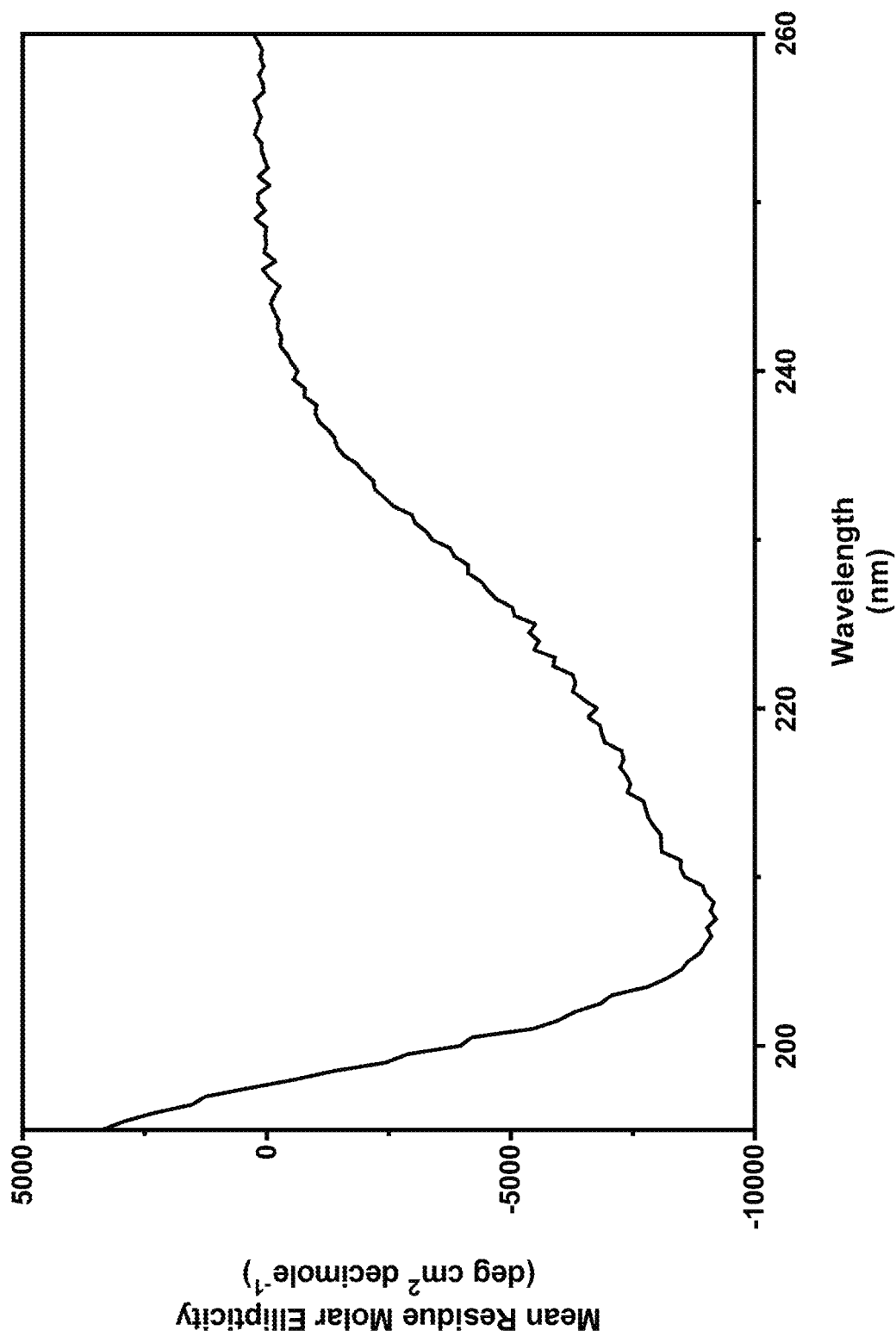
FIG. 11 shows the results for Far UV CD Spectroscopy analysis of nanoparticle formulation C13 depicted as mean residues molar ellipticity (deg cm$^2$ per decimole) as a function of wavelength (nm).

For both far and near UV CD spectroscopy, the averaged spectrum was buffer subtracted and normalized to the mean residue molar ellipticity (MRME). A quantitative analysis of spectral similarity was performed using the weighted spectral difference (WSD) algorithm. The resulting far UV spectra, provided in FIG. 11, suggest that protein secondary structure consists primarily of β-sheets. There was little evidence of α-helical structure present. The near UV spectra, provided in FIG. 12, indicated weak tryptophan, high tyrosine, and very high disulfide features, This result is consistent with the number of tryptophan, tyrosine and disulfides residues in the molecule, as shown in the table below.

Tryptophan, Tyrosine and Disulfides in the MYC-containing Nanoparticle Formulations

| Amino Acid Residue | Number per Molecule |
| --- | --- |
| Tryptophan | 2 |
| Tyrosine | 12 |
| Disulfides | 4 (9 cysteines) |

D. Fourier Transform Infrared Spectroscopy (FTIR)

Fourier transform infrared spectroscopy (FTIR) spectra from wavenumbers 1700-1500 $cm^{-1}$ can be used to determine structural properties of proteins. Analysis in this spectral region results in two absorption bands, conventionally called Amide I and Amide II and lying between wavenumbers 1700-1600 $cm^{-1}$ and 1600-1500 $cm^{-1}$, respectively. The Amide 1 band is due to C=O stretching vibrations of the peptide bonds, which are modulated by the secondary structure (α-helix, β-sheet, etc.). Secondary structural content can be obtained by comparing the measured spectra to the spectra obtained for proteins with known secondary structures. FTIR spectroscopy for nanoparticle formulation C14 was performed using a Bruker Optics Vertex 70, with MCT detector and BioATR Cell II. The samples required no preparation prior to analysis. Testing parameters for the analysis are shown in the table below.

FTIR Testing Parameters

| Parameter | Value |
| --- | --- |
| Temperature | 25° C. |
| Concentration | Neat |
| Detector | MCT |
| Aperture Setting | 6 mm |
| Resolution | 4 $cm^{-1}$ |
| Beamsplitter Setting | KBr |
| High Pass Filter | Open |
| Low Pass Filter | 10 kHz |
| Wavenumber Range* | 6000-950 $cm^{-1}$ |
| Scanner Velocity | 20 kHz |
| Number of scans | 128 |

*Wave number range was suggested. Buffer subtraction is typically done between 2800-1000 $cm^{-1}$ and secondary structure spectral analysis performed between 1700-1600 $cm^{-1}$.

The resulting FTIR spectrum was buffer subtracted and min-max normalized across 1600 to 1700 $cm^{-1}$. Nine-point smoothing was applied to minimize white noise for the determination of the second derivative. A quantitative analysis of spectral similarity was performed using the weighted spectral difference (WSD) algorithm.

Nanoparticle formulation C14 showed a significant beta structure, both sheet and turn. The peak around 1649-1655 is random coil. These spectral features are consistent with the qualitative analysis of the far UV CD data: i.e. primarily beta structures and random coil, and very little to no α-helix is present.

E. Analytical Ultracentrifugation

The higher order structure of nanoparticle formulation C13 was investigated based on the sedimentation behavior of the protein in solution by sedimentation velocity analytical ultracentrifugation (SV-AUC). SV-AUC measures the rate at which molecules sediment in response to a centrifugal force. This sedimentation rate provides information on the molecular weight of molecules present in the sample.

Figure 14:
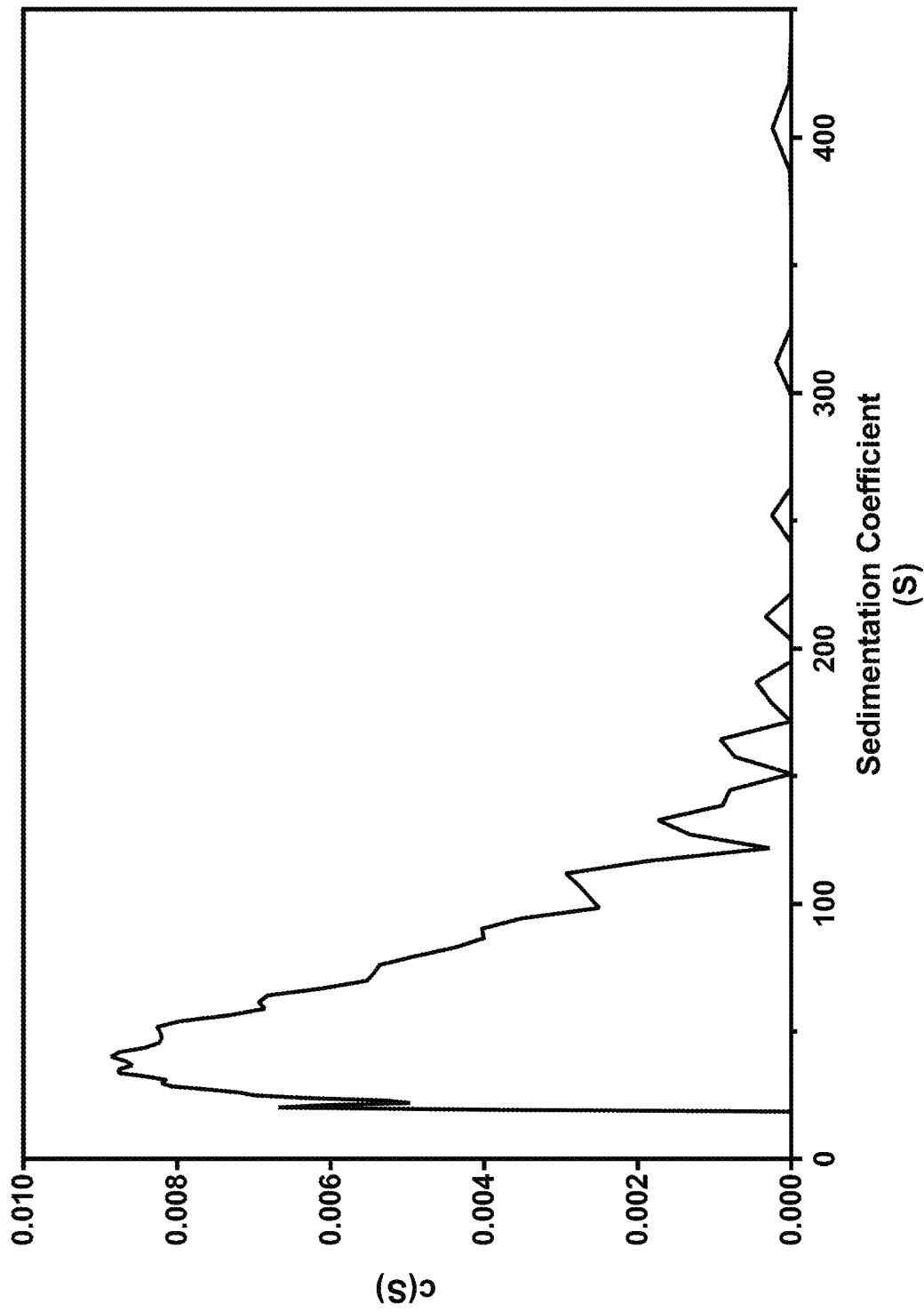
FIG. 14 shows Analytical Ultracentrifugation (AUC) data for nanoparticle formulation C13.

SV-AUC was performed using a Beckman-Coulter XLI, using absorbance optics. The samples required no additional preparation prior to analysis. The testing parameters are shown in the table below. Data analysis was performed using SEDFIT 15.01b using parameters as shown in the table below. AUC data are illustrated in FIG. 14.

AUC Testing Parameters

| Parameter | Value |
| --- | --- |
| Temperature | 20° C. |
| Concentration | Neat |
| Detection | Absorbance at 280 nm |
| Angular Velocity | 20,000 rpm |
| Radial scan increment | 0.003 cm |
| Centerpiece | Epon 12 mm, 2 sector |

AUC Data Analysis Parameters

| Parameter | Value |
| --- | --- |
| Meniscus | Float from max of sample side spike |
| Bottom | 7.2 cm |
| Bottom fitting limit | 6.7 cm |
| Frictional ratio | Float from 2.2 |
| Buffer density | 1.05507 g/L |
| Buffer Viscosity | 0.01628 Poise |
| Partial specific volume | 0.73 |
| Sedimentation coefficient range | 0.1[1]-500 S |
| Regularization Method | Tikhonov-Phillips |
| Time independent noise | Enabled |
| Radial independent noise | Disabled |

[1]Log spaced s grid was used thus all values must be greater than zero

Nanoparticle formulation C13 demonstrated a large molecular weight distribution. Approximate molecular weights were determined using known buffer properties. The distribution began sharply at ~4 MDa (20.6 S) and had an apex at ~10MDa (40 S). The main population distribution extended out to ~120MDa (185 S). Low quantities of larger species extended beyond 400 S, however these species are below the limit of quantitation of the method and cannot be accurately quantified.

F. Denaturing Size Exclusion Chromatography-HPLC

Nanoparticle formulation C13 was analyzed by denaturing size exclusion chromatography-HPLC (dSEC-HPLC). The samples were run under denaturing conditions, both reducing and non-reducing conditions utilizing a TSKgel G3000SWx1; 5 μm; A Stainless Steel 7.8 mm×30 cm column was used to achieve size-based separation of monomer from larger molecular weight species within the sample.

For the analysis of samples under non-reducing conditions, elution was achieved using 7.5M Gdn HCl, 0.01M Sodium Acetate pH 4.7 as mobile phase in an isocratic configuration. Samples were diluted 1/10 in mobile phase and vortexed for 10 seconds to mix. The samples were then incubated at 37° C. for 30 minutes before placing into the autosampler at 4° C.

For the analysis of samples under reducing conditions, elution was achieved using 7.5M Gdn HCl, 0.0625M TrisHCl pH 7.3 as mobile phase in an isocratic configuration. Samples were diluted 1/10 in mobile phase, and 1 mL of TCEP was added prior to vortexing for 10 seconds to mix.

The samples were then incubated at 37° C. for 15 minutes before placing into the autosampler at 4° C.

Detection for both reducing and non-reducing conditions was performed using fluorescence for quantitation of peaks. An evaluation of size distribution across peaks was achieved using multi-angle laser light scattering (MALLS).

Figure 15A:
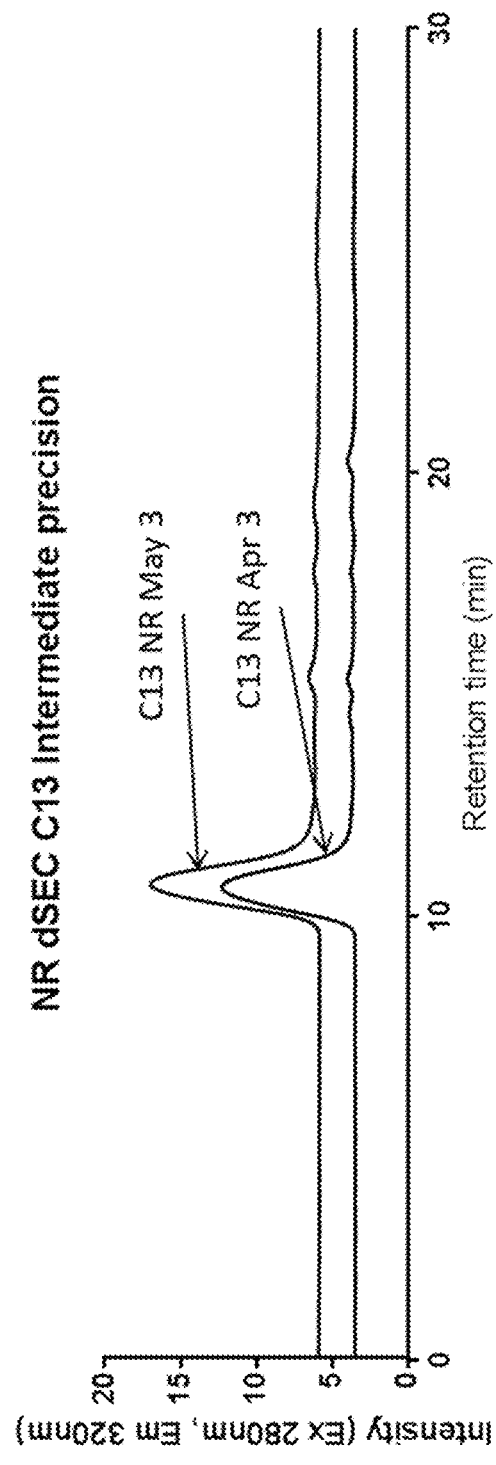
FIG. 15A and FIG. 15B show Non-reduced (NR) and Reduced (R) Denaturing SEC chromatograms, respectively, for nanoparticle formulation C13. The overlaid traces on each chromatogram represent testing that was performed approximately 1 month apart for samples stored at 2° C.-8° C.
Figure 15B:
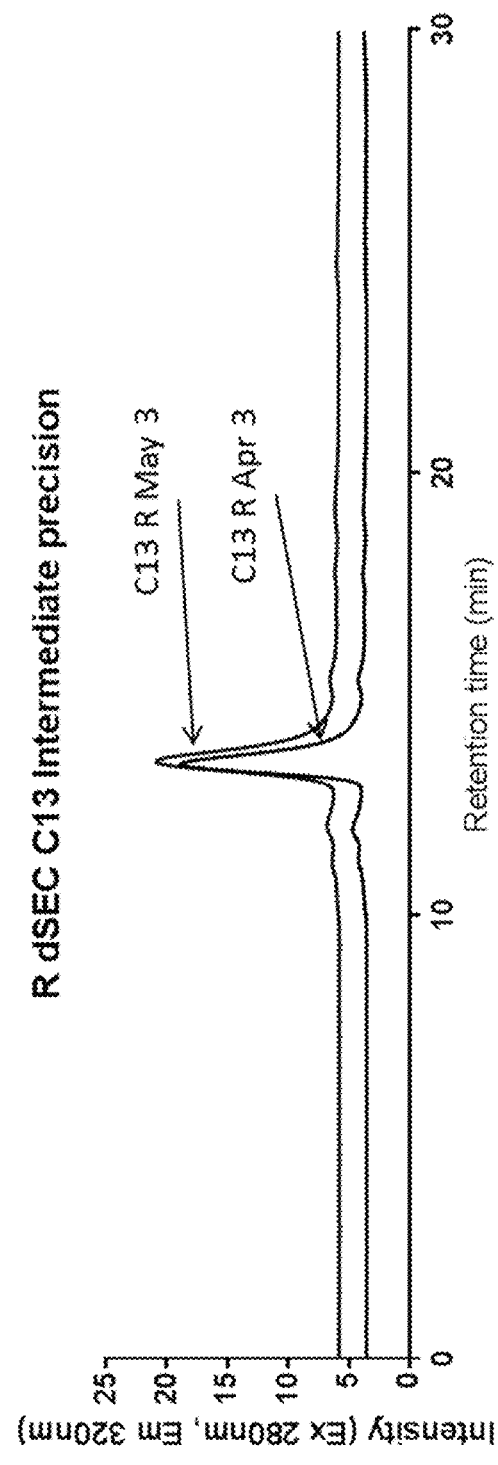

The resulting chromatograms for SEC-HPLC analysis of nanoparticle formulation C13 are shown in FIG. 15. The overlaid traces on each chromatogram represent testing that was performed approximately 1 month apart for samples stored at 2-8° C., demonstrating the ability of the method to pick up changes upon storage at accelerated temperature.

G. Electron Microscopy

Electron microscopy was performed for the collection of images of the three dimensional structure of nanoparticle formulation C2B. A fifty-microliter drop of the nanoparticle formulation (100 ug/mL) was spotted onto parafilm and then absorbed to glow-discharged, carbon- and formvar-coated copper transmission electron microscopy (TEM) grids (G400 copper; EM Science). Grids were blotted dry on Kimwipe (Kimberly-Clark), followed by staining with uranyl acetate (2% [wt/vol]) and TEM (Philips CM10) at 80 kV. The number 100-nm particles were imaged at ×4,800 magnification. The resulting images confirm a highly ordered complex of self-assembling spheres, as shown in FIG. 7.

EXAMPLE 6

Characterization of Mutant TAT-MYC Peptide Formulations

In this Example, point mutations in MYC at sites that play a role in MYC function, were examined to determine whether the mutations affect the stability of a TAT-MYC nanoparticle formulation. As described above, a TAT-MYC fusion protein having the sequence set forth in SEQ ID NO: 1 is a fusion protein that combines the protein transduction domain (PTD) of HIV-1 TAT fused in frame to the wild-type human MYC protein (c-MYC), followed by two tags: V5 and 6xHis. TAT-3AMYC is identical to TAT-MYC, except that it contains 3 amino acid substitutions: T358A, S373A, and T400A. These three amino acids were initially selected for mutation because phosphorylation at all three residues has been shown to reduce MYC function by inhibiting the association of MYC with DNA, either by blocking Max binding or by interfering directly with binding to DNA (Huang et al. *Mol Cell Biol.* 24(4): 1582-1594 (2004)). As detailed below, the point mutations of TAT-3AMYC appear to destabilize the complex formed render the fusion protein preparation non-functional.

Preparation of TAT-MYC and TAT-3AMYC Fusion Proteins

TAT-MYC and TAT-3AMYC proteins were prepared as described above in Examples 1 and 2. The fusion proteins were solubilized under denaturing conditions and then refolded into a final formulation containing salts, glycerol and reducing agent (i.e.50 mM Phosphate, 500 mM NaCl, 10% Glycerol, 5 mM GSH, (Reduced Glutathione) 1 mM GSSG (Oxidized Glutathione).

Size Exclusion Chromatography HPLC (SEC-HPLC)

The nanoparticle formulations comprising TAT-MYC and TAT-3AMYC were then analyzed for their molecular weight profiles using size exclusion chromatography HPLC (SEC-HPLC). Size variants were separated with an isocratic mobile phase (4M GdnHCl, 10 mM NaOAc, pH 4.65) over a size exclusion column and were monitored on a Diode Array Detector with ultraviolet (UV) detection at 280 nM. The parameters used were as follows: Flow rate: 0.75 mL/min; Maximum pressure limit: 70.0 bar; Run time: 30 minutes; Injection Volume: 20 µL).

Figure 16A:
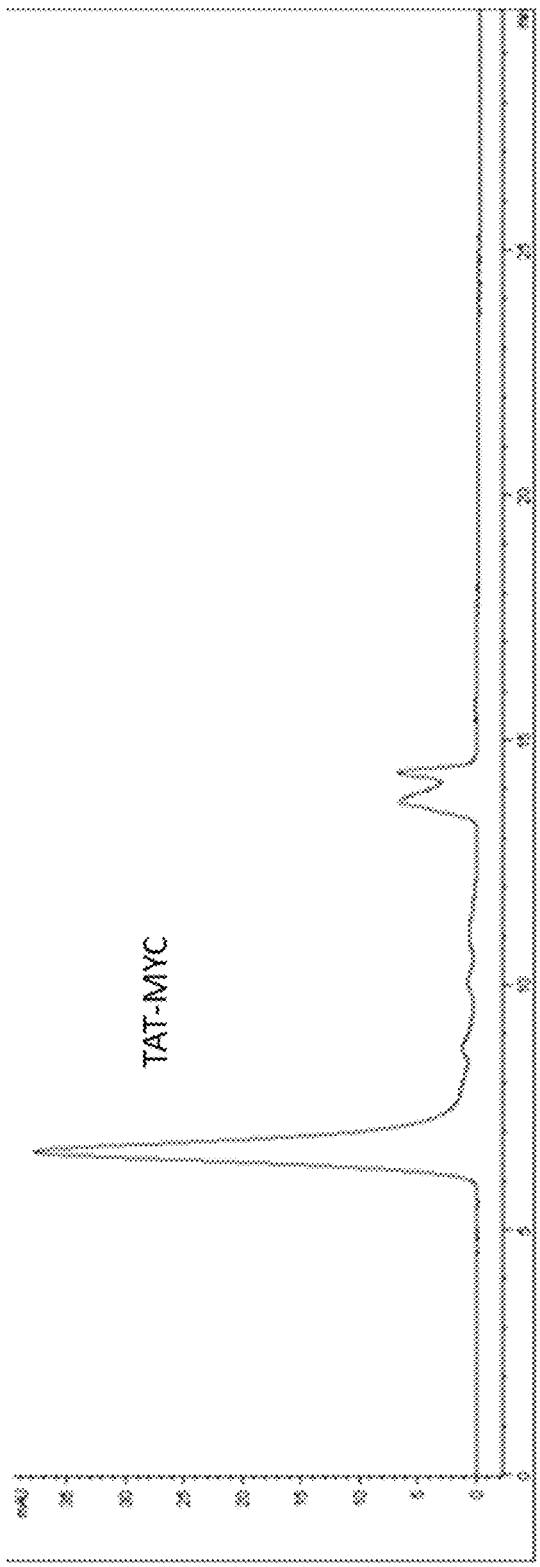
FIG. 16A and FIG. 16B show denaturing SEC chromatograms for TAT-MYC and TAT-3AMYC nanoparticle formulations.
Figure 16B:
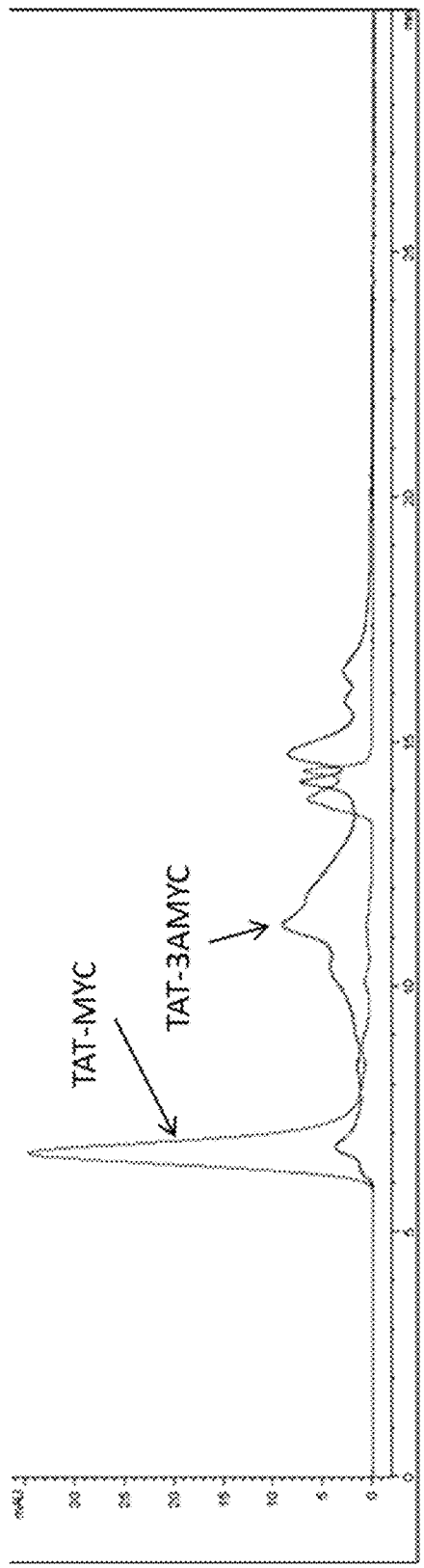

FIG. 16A shows the chromatogram of the TAT-MYC protein preparation. The protein complex elutes between minutes 6 and 7. Smaller protein multimers and excipient peaks can be seen eluting between minutes 8 and 15. FIG. 16B shows the chromatogram of TAT-3AMYC compared to the TAT-MYC protein preparation. The TAT-3AMYC has significantly less protein complex that elutes between minutes 6 and 7. The bulk of the protein preparation was comprised of smaller protein multimers and excipient peaks can be seen eluting between minute 8 and 17. This indicates that mutation of T358, S373, and T400 to alanine are sufficient to disrupt the formation of the nanoparticle complex that elutes between minute 6 and 7 on an SEC column.

Potency Assay

The TAT-MYC and TAT-3AMYC fusion proteins were also assessed for potency by testing their ability to rescue activated CD4+ T-cells from apoptosis, retain a blasting phenotype, and continue to proliferate after the antigenic stimulation. T cells were for the assay were obtained by harvesting Spleen and Lymph Nodes from mice. The spleen and lymph nodes were ground through the mesh screen to generate a single cell suspension in C10 culture media. The cells were transferred to a conical tube and pelleted by centrifugation at 1200 RPM for 5 min. The cells were resuspended in 5 ml sterile TAC buffer (135 mM NH$_4$Cl, 17 mM Tris pH 7.65) and allowed to sit in TAC buffer for 1-2 min to lyse the red blood cells. The cells were centrifuged at 1200 RPM for 5 min, washed with 10 mls of C10 media, and resuspended in 4 ml C10 medium.

T cells were isolated from the resuspended RBC-depleted cell mixture using anti-CD4 Dynabeads according to the manufacturer's instructions (Invitrogen Cat #11445D). Briefly, 4 ml of the resuspended cell pellet was added to a snap cap tube with 50 µl washed CD4 Dynabeads (×4) and incubated for 1 hour at 4° C. on a 360° Nutator. After incubating, the tubes were placed on a Dynal magnet, allowing two minutes for beads and cells to collect on the side of the tube. The supernatants (CD4 negative cells) were removed. The beads and bound cells were resuspended in 4 ml C10 media, and placed back on magnet to allow for separation. This wash was repeated. After washing, the beads and bound cells were resuspended in 4 ml C10, and 50 µl CD4 detachabead (Invitrogen Cat #12406D) was added to each tube and incubated for 1 hour at 22° C. on a 360° Nutator. After incubating, the tubes were placed on the Dynal magnet, allowing two minutes for beads to collect on the side of the tube. The supernatants containing the CD4+ cells were collected in a 50 ml conical tube. The remaining beads were resuspended in 10 ml C10 media, separated on the Dynal magnet and collected. This step was then repeated and the supernatants pooled. The pooled isolated CD4+ cells were centrifuged at 1200 rpms for 5 minutes. The supernatant was removed and the cells were resuspended in 20 ml (5 ml/mouse) at approximately 1.5×10$^6$ cells/ml. 20 ul commercial anti-CD3 (eBiosciences Cat #16-0031-86) and 20 ul anti-CD28 antibody (clone 37N1) at 1 ul/ml were added to the tube to activate the T cells and the cells were seeded in 20 wells of 24 well dish, 1 ml of media per well and incubated 72 hr at 36° C.

At 72 hours post activation with anti-CD3 and anti-CD28, the media and the cells were removed from each well from 24 well dish using media to wash cells from the bottom of each well. The cells were pelleted at 1200 rpms for five minutes, resuspended in 5 ml C10 medium and transferred to 15 ml conical tube. The cells were underlayed with 5 ml Ficoll-Paque and spun at 1200 rpms, five minutes. The buffy coat was removed using a 4 ml glass pipette and transferred to a new 15 ml conical tube. 10 ml of C10 media was added to wash cells. The cells were pelleted at 1200 rpms for five minutes, resuspended at $1 \times 10^6$ cells/ml and seeded 1 ml per well of a 24-well plate. The cells were then treated with the TAT-MYC or TAT-3AMYC fusion proteins. Viability was determined by 48 hr after treating with fusion proteins using flow cytometry.

Figure 17:
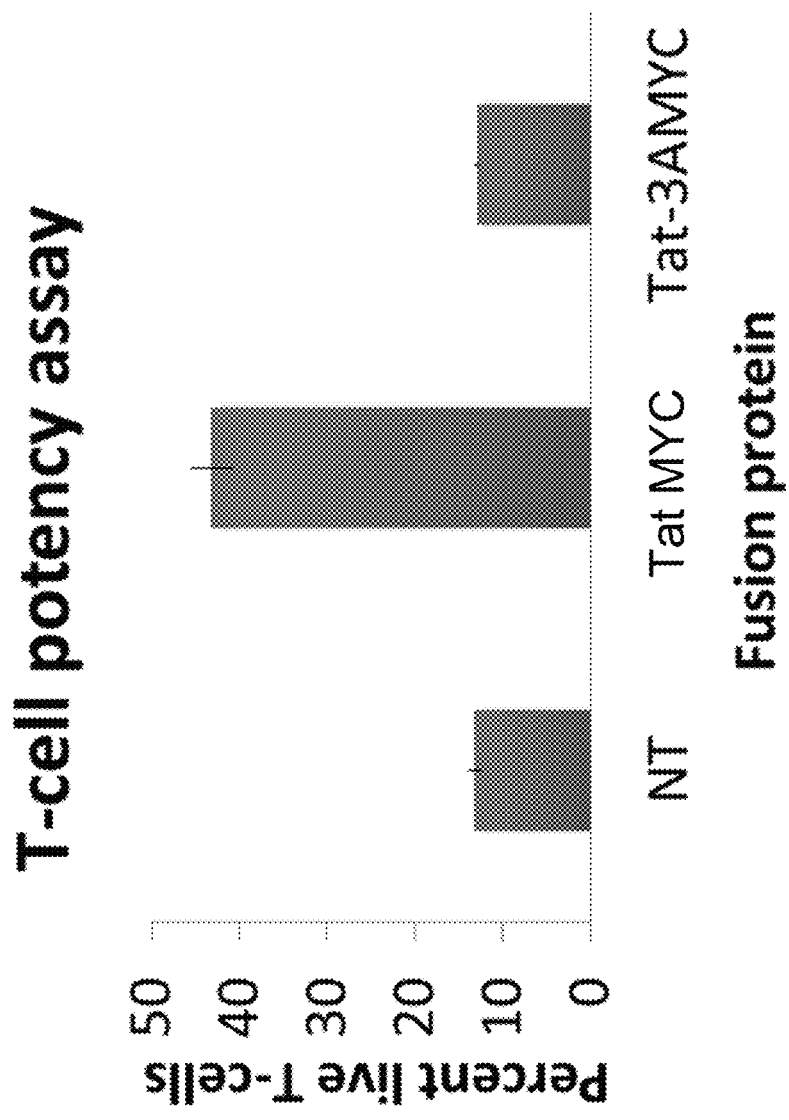
FIG. 17 shows the results of a T cell potency assay. TAT-MYC showed a 3 fold increase the live population T-cell population compared to no treatment (NT). TAT-3AMYC showed no increase the live T-cell population compared to no treatment (NT).

FIG. 17 shows a graphical representation of an activated T-cell potency assay evaluating the ability of TAT-MYC and TAT-3AMYC to rescue activated T-cell from apoptosis that follows cytokine withdrawal. TAT-MYC showed a 3 fold increase in the live T-cell population after cytokine withdrawal compared to no treatment (NT). TAT-3AMYC, however, showed no increase the live population T-cell population compared to no treatment (NT). This result was in line with the chromatography data, which showed that the majority of the TAT-3AMYC does not form a complex like TAT-MYC as shown in FIG. 16B.

In summary, TAT-MYC forms a nanoparticle complex that can be measured by SEC-HPLC and elutes between minute 6 and 7. TAT-3AMYC does not form the same nanoparticle complex as TAT-MYC. Mutation of T358, S373, and T400 to alanine was sufficient to disrupt the formation of the complex that elutes between minutes 6 and 7 on an SEC column. Further, the function of TAT-MYC observed in a T-cell potency assay appears to correlate with formation of this complex.

EXAMPLE 7

Construction and Characterization of a TAT-MYC Fusion Peptide Derived from *Chlorocebus sabaeus* (Green Monkey) MYC Protein Construction and Purification of Green monkey TAT-MYC Plasmid pTAT-MYC (Green Monkey)-V5-6xHis was made by PCR amplification of the coding regions for *C. sabaeus* (green monkey) MYC and replacing the nucleic acid encoding human MYC sequence in the human TAT-MYC vector of Example 1 with a portion of the green monkey MYC sequence encoding SEQ ID NO: 8, which differs from the human MYC sequence by two amino acids. Protein production and purification were performed as described in Example 1. Preparation of nanoparticulate TAT-MYC composition was performed as described in Example 2.

Dynamic Light Scattering (DLS) to Verify Particle Size

Figure 18:
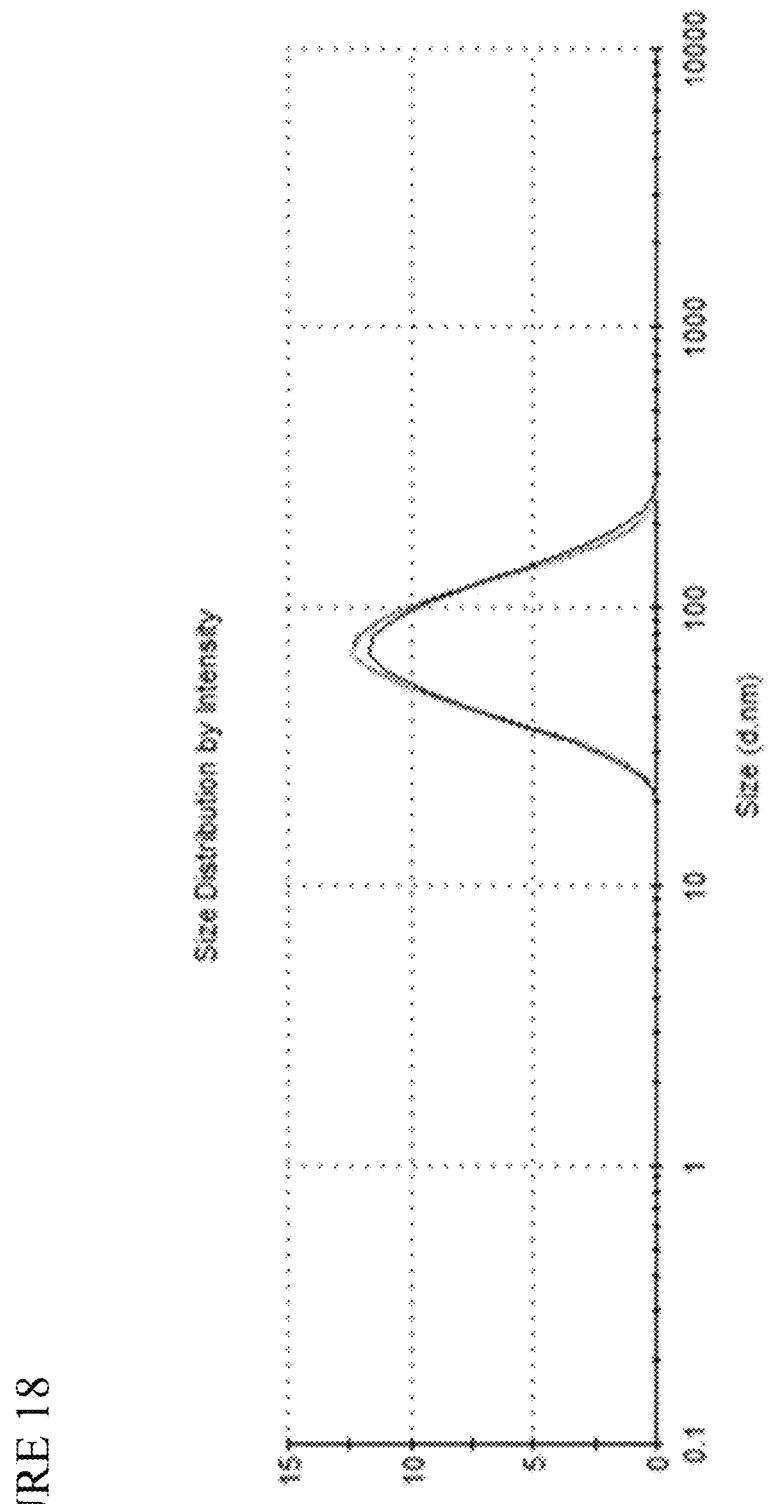
FIG. 18 depicts size distribution of MYC-containing nanoparticles in selected formulations of Green Monkey TAT-MYC analyzed by Dynamic Light Scattering (DLS) technique.

The refolded nanoparticulate compositions were assessed for nanoparticle size distribution by Dynamic Light Scattering (DLS) technique as described in Example 4(B)(3). Results are shown in FIG. 18, which shows the DLS traces for the Green Monkey TAT-MYC nanoparticulate compositions. The average particle size (diameter) for the Green Monkey TAT-MYC was about 80 nm.

Reversed Phase High Performance Liquid Chromatography (RP-HPLC)

Figure 19:
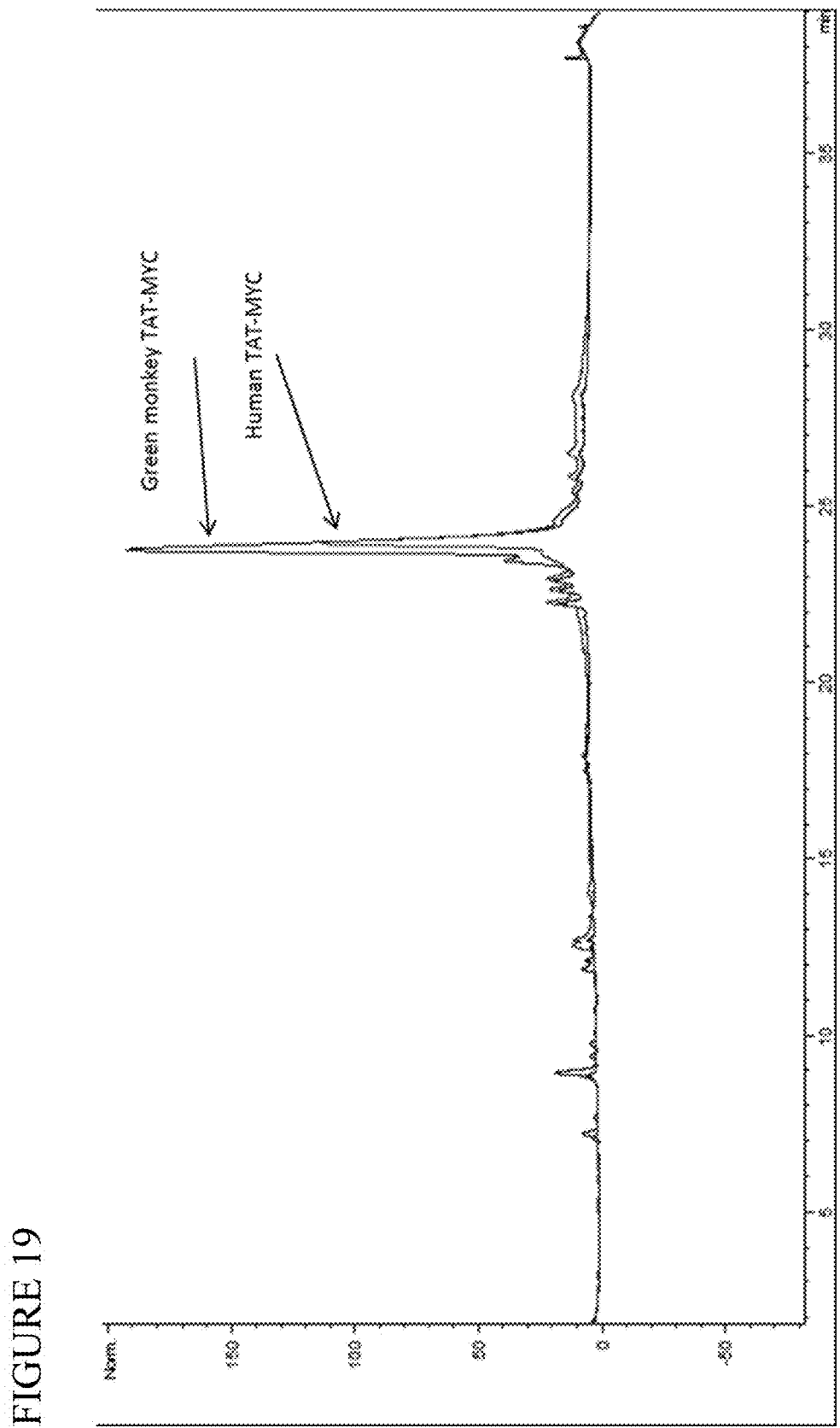
FIG. 19 shows RP-HPLC Chromatograms for Green Monkey TAT-MYC compared to human TAT-MYC.

A reversed phase HPLC (RP-HPLC) method was employed for the quantitation of post translational modifications and product related impurities in the Green Monkey TAT-MYC nanoparticulate composition. The test sample was diluted in denaturing buffer (7.5 M Guanidine HCl, 0.0625M TrisHCl pH 7.3) to 1 mg/ml. 2 µl of 0.5M TCEP ((tris(2-carboxyethyl)phosphine) was added to the sample, incubated at 37° C. for 30 minutes, then cooled to 2-8° C. The sample was stored at 2-8° C. for up to 5 days prior to analysis. The sample (50 µl (~5 µg) was separated using an Agilent AdvanceBio RP-mAb C4 column (2.1×150 mm, Solid core beads 3.5 µm, 450 Å). The column was equilibrated at a temperature of 50° C. Elution was achieved by applying a flow rate of 0.5 mL/min and a linear gradient of 0.1% TFA (w/v) in 100% $H_2O$ (Eluent A) and 0.1% (w/v) TFA in 100% ACN (Eluent B) as shown in the table below. Detection was performed at 215 nm. Results for the Green Monkey TAT-MYC nanoparticulate composition compared to a reference human TAT-MYC nanoparticulate composition are shown in FIG. 19.

Size Exclusion Chromatography and High Performance Liquid Chromatography (SEC-HPLC)

The Green Monkey TAT-MYC nanoparticulate compositions were also characterized via size exclusion chromatography followed by high performance liquid chromatography. The samples were run under denaturing, non-reducing conditions utilizing a TSKgel G3000SWx1; 5 µm; A Stainless Steel 7.8 mm×30 cm column to achieve size-based separation of monomer from larger molecular weight species within the sample. Elution was achieved using 4M Gdn HCl, 0.1M Sodium Acetate pH 4.65 as the mobile phase in an isocratic configuration. Samples were diluted 1/10 in mobile phase and vortexed for 10 seconds to mix. The samples were then incubated at 37° C. for 30 minutes before placing into the autosampler at 4° C.

Figure 20:
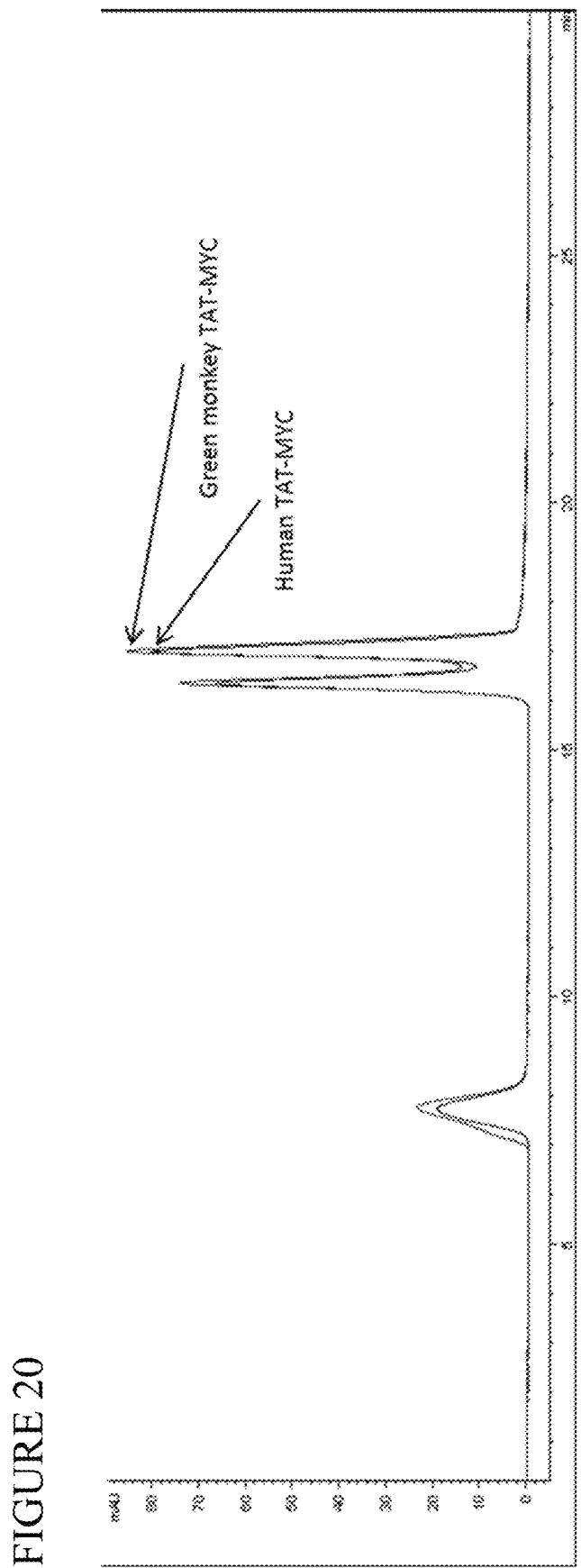
FIG. 20 shows SEC-HPLC Chromatograms for Green Monkey TAT-MYC compared to human TAT-MYC.

The resulting chromatograms for SEC-HPLC analysis of Green Monkey TAT-MYC nanoparticulate compositions compared to a reference human TAT-MYC nanoparticulate composition are shown in FIG. 20.

Potency Assay

The Green Monkey TAT-MYC nanoparticulate compositions and reference human TAT-MYC nanoparticulate compositions were also assessed for potency by testing their ability to rescue activated CD4+ T-cells from apoptosis, retain a blasting phenotype, and continue to proliferate after the antigenic stimulation. The compositions were assayed for biological activity according to the potency assay described in Example 6.

Figure 21:
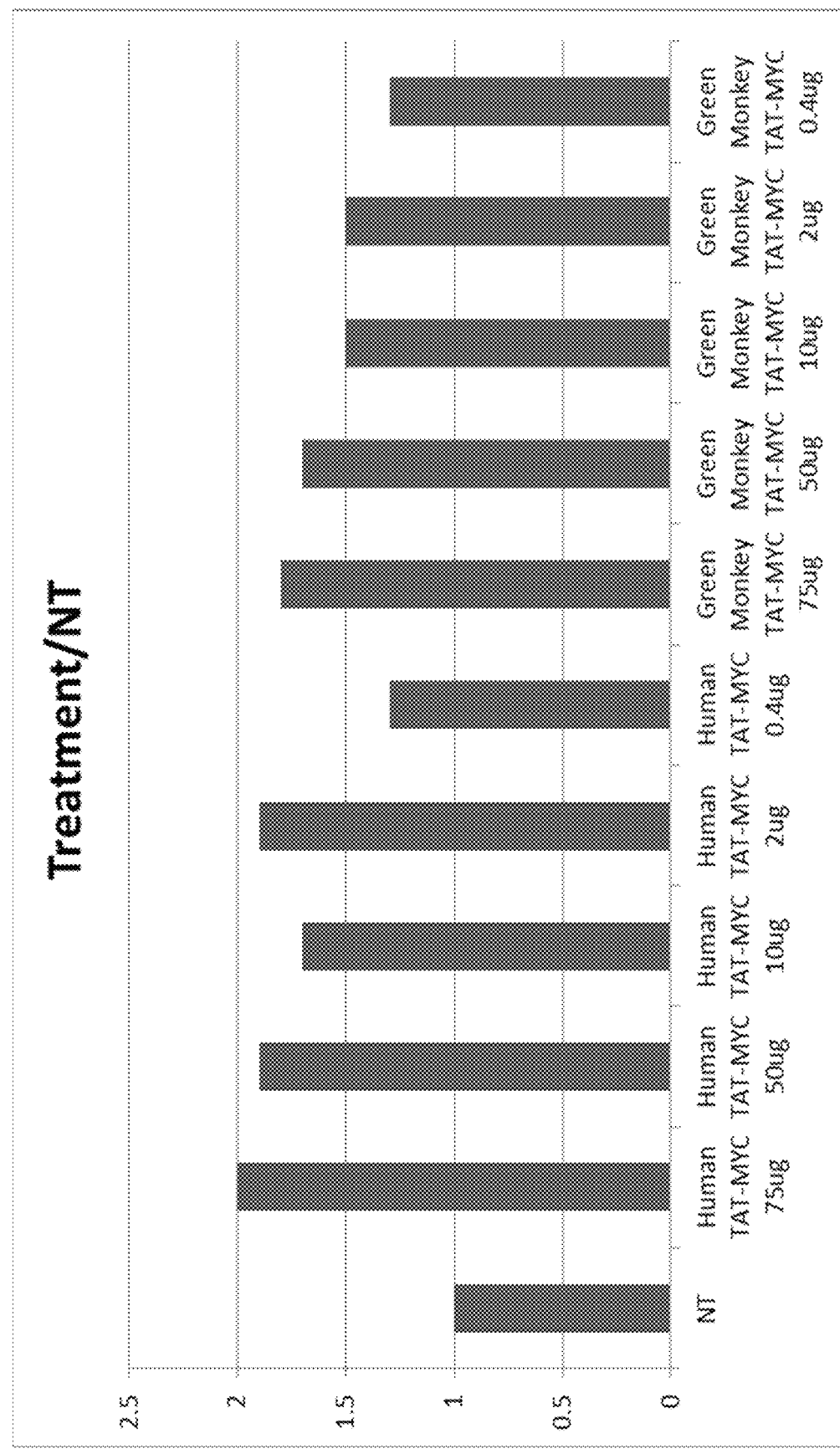
FIG. 21 shows the results of a T cell potency assay for Green Monkey TAT-MYC compared to human TAT-MYC.

FIG. 21 shows a graphical representation of an activated T-cell potency assay evaluating the ability of Green Monkey TAT-MYC and human TAT-MYC at various doses to increase the amount of activated T-cells having a blasting phenotype relative no treatment control.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

All patents, patent applications, provisional applications, and publications referred to or cited herein are incorporated by reference in their entirety, including all figures and tables, to the extent they are not inconsistent with the explicit teachings of this specification.

Other embodiments are set forth within the following claims.

What is claimed is:

1. A composition comprising a population of biologically active nanoparticles comprising one or more MYC-containing polypeptides wherein:

a) the average diameter of the biologically active nanoparticles is between about 80 nm and about 150 nm;

b) the pH of the formulation is at least about pH 6.0, and no greater than about pH 8; and c) contacting an anti-CD3 or anti-CD28 activated T-cell with the MYC-containing polypeptide nanoparticle composition under conditions suitable for T-cell proliferation, augments one or more of the activation, survival, or proliferation of the T-cell compared with an anti-CD3 or anti-CD28 activated T-cell that is not contacted with the MYC polypeptide-containing composition; and wherein the MYC-containing polypeptide comprises a MYC fusion protein, comprising a protein transduction domain linked to a MYC polypeptide.

2. The composition of claim 1, wherein the nanoparticles have an average diameter of about 90-140 nm.

3. The composition of claim 1, wherein the nanoparticles have an average diameter of between about 100 nm and about 110 nm.

4. The composition of claim 1, wherein the nanoparticles have a molecular mass of about $10^4$-$10^6$ daltons.

5. The composition of claim 1, wherein the nanoparticles comprise about 200 molecules of the MYC-containing polypeptide.

6. The composition of claim 1, wherein the MYC polypeptide is acetylated.

7. The composition of claim 1, wherein the MYC fusion peptide further comprises one or more linkers that link the protein transduction domain and the MYC polypeptide.

8. The composition of claim 1, wherein the MYC-containing polypeptide comprises a MYC fusion peptide with the following general structure:
   protein transduction domain-X-MYC sequence,
   wherein -X- is a linker that links the protein transduction domain and the MYC sequence.

9. The composition of claim 1, wherein the protein transduction domain sequence is a TAT protein transduction domain sequence.

10. The composition of claim 9, wherein the TAT protein transduction domain sequence is selected from the group consisting of TAT[48-57] and TAT[57-48].

11. The composition of claim 1, wherein the MYC polypeptide is a MYC fusion peptide comprising SEQ ID NO: 1 or 10.

12. The composition of claim 1, further comprising a pharmaceutically acceptable excipient.

13. The composition of claim 1, formulated for topical administration, oral administration, parenteral administration, intranasal administration, buccal administration, rectal administration, or transdermal administration.

* * * * *

UNITED STATES PATENT AND TRADEMARK OFFICE
CERTIFICATE OF CORRECTION

PATENT NO. : 10,583,156 B2
APPLICATION NO. : 15/828971
DATED : March 10, 2020
INVENTOR(S) : Turner et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 68 days.

Signed and Sealed this
Twenty-fifth Day of February, 2025

Coke Morgan Stewart
*Acting Director of the United States Patent and Trademark Office*